US011007063B2

(12) United States Patent
Goldberg et al.

(10) Patent No.: US 11,007,063 B2
(45) Date of Patent: May 18, 2021

(54) OFFSET REAMERS

(71) Applicant: CATALYST ORTHOSCIENCE INC., Naples, FL (US)

(72) Inventors: Steven S. Goldberg, Naples, FL (US); Stephen M. Herrington, Naples, FL (US); Ephraim Akyuz, Salt Lake City, UT (US)

(73) Assignee: CATALYST ORTHOSCIENCE INC., Naples, FL (US)

( * ) Notice: Subject to any disclaimer, the term of this patent is extended or adjusted under 35 U.S.C. 154(b) by 267 days.

(21) Appl. No.: 15/918,088

(22) Filed: Mar. 12, 2018

(65) Prior Publication Data

US 2018/0200068 A1 Jul. 19, 2018

Related U.S. Application Data

(63) Continuation-in-part of application No. 15/660,942, filed on Jul. 26, 2017, now Pat. No. 10,973,646.
(Continued)

(51) Int. Cl.
*A61B 17/16* (2006.01)
*A61B 17/17* (2006.01)
(Continued)

(52) U.S. Cl.
CPC ........ *A61F 2/4081* (2013.01); *A61B 17/1604* (2013.01); *A61B 17/1617* (2013.01); *A61B 17/1684* (2013.01); *A61B 17/1778* (2016.11); *A61F 2/30771* (2013.01); *A61B 17/1659* (2013.01); *A61F 2002/30156* (2013.01); *A61F 2002/30878* (2013.01); *A61F 2002/30881* (2013.01); *A61F 2002/30884* (2013.01);
(Continued)

(58) Field of Classification Search
CPC ............ A61B 17/1778; A61B 17/1746; A61B 17/1604; A61B 17/1684; A61B 17/1666
See application file for complete search history.

(56) References Cited

U.S. PATENT DOCUMENTS 4,106,130 A 8/1978 Scales
4,206,517 A 6/1980 Pappas
(Continued)

FOREIGN PATENT DOCUMENTS

AU 2013209336 2/2014
AU 2014249514 10/2015
(Continued)

OTHER PUBLICATIONS

Synthes Epoca Shoulder Technique Guide.

*Primary Examiner* — Matthew J Lawson
*Assistant Examiner* — Lisa Nguyen
(74) *Attorney, Agent, or Firm* — David Meibos; Maywood IP Law

(57) ABSTRACT

Low profile offset reamers include reamer heads with outer diameters that are substantially greater than the overall height of the working portion, which includes the reamer head, a reamer coupler, and a working tip that supports the reamer head and reamer coupler. The overall height is measured parallel to the rotational axis of the reamer head, and the outer diameter is measured perpendicular to the rotational axis.

25 Claims, 34 Drawing Sheets

Related U.S. Application Data which is a continuation-in-part of application No. 14/042,258, filed on Sep. 30, 2013, now Pat. No. 9,775,716, and a continuation-in-part of application No. 15/587,895, filed on May 5, 2017, now abandoned, and a continuation-in-part of application No. 14/592,837, filed on Jan. 8, 2015, now Pat. No. 9,814,471, and a continuation-in-part of application No. 15/228,443, filed on Aug. 4, 2016, now Pat. No. 9,814,588, and a continuation-in-part of application No. 15/653,305, filed on Jul. 18, 2017, now abandoned, said application No. 15/587,895 is a continuation of application No. 14/042,258, filed on Sep. 30, 2013, now Pat. No. 9,775,716, said application No. 14/592,837 is a continuation-in-part of application No. 14/042,258, filed on Sep. 30, 2013, now Pat. No. 9,775,718, said application No. 15/653,305 is a continuation-in-part of application No. 15/228,443, filed on Aug. 4, 2016, now Pat. No. 9,814,588.

(60) Provisional application No. 62/470,792, filed on Mar. 13, 2017, provisional application No. 62/367,533, filed on Jul. 27, 2016, provisional application No. 61/776,398, filed on Mar. 11, 2013, provisional application No. 61/925,893, filed on Jan. 10, 2014, provisional application No. 62/203,255, filed on Aug. 10, 2015, provisional application No. 62/363,607, filed on Jul. 18, 2016.

(51) Int. Cl.
  *A61F 2/30* (2006.01)
  *A61F 2/40* (2006.01)

(52) U.S. Cl.
  CPC ........... *A61F 2002/30892* (2013.01); *A61F 2002/30902* (2013.01); *A61F 2002/30904* (2013.01)

(56) References Cited

U.S. PATENT DOCUMENTS

| | | | |
|---|---|---|---|
| 4,550,450 A | 11/1985 | Kinnett | |
| 4,795,468 A | 1/1989 | Hodorek | |
| 4,865,605 A | 9/1989 | Dines | |
| 4,936,853 A | 6/1990 | Fabian | |
| 4,964,865 A | 10/1990 | Burkhead | |
| 4,986,833 A | 1/1991 | Worland | |
| 5,030,219 A * | 7/1991 | Matsen, III | A61F 2/4081 606/53 |
| 5,032,132 A | 7/1991 | Matsen, III | |
| 5,383,936 A | 1/1995 | Kubein-Meesenburg | |
| 5,489,309 A | 2/1996 | Lackey | |
| 5,489,310 A | 2/1996 | Mikhail | |
| 5,593,448 A | 1/1997 | Dong | |
| 5,702,447 A | 12/1997 | Walch | |
| 5,723,018 A | 3/1998 | Cyprien | |
| 5,769,856 A | 6/1998 | Dong | |
| 5,800,551 A | 9/1998 | Williamson | |
| 5,814,049 A | 9/1998 | Pratt | |
| 5,851,207 A | 12/1998 | Cesarone | |
| 5,919,195 A | 7/1999 | Wilson | |
| 5,928,285 A | 7/1999 | Bigliani | |
| 5,944,758 A | 8/1999 | Mansat | |
| 5,976,144 A | 11/1999 | Fishbein | |
| 6,129,732 A | 10/2000 | Lechot | |
| 6,245,074 B1 * | 6/2001 | Allard | A61B 17/1615 606/80 |
| 6,364,910 B1 | 4/2002 | Shultz | |
| 6,379,386 B1 | 4/2002 | Resch | |
| 6,406,495 B1 | 6/2002 | Schoch | |
| 6,475,221 B1 | 11/2002 | White | |
| 6,673,115 B2 | 1/2004 | Resch | |
| 6,679,916 B1 | 1/2004 | Frankle | |
| 6,699,289 B2 | 3/2004 | Iannotti | |
| 6,783,549 B1 | 8/2004 | Stone | |
| 6,875,234 B2 | 4/2005 | Lipman | |
| 6,911,047 B2 | 6/2005 | Rockwood, Jr. | |
| 7,008,430 B2 | 3/2006 | Dong | |
| 7,048,740 B2 | 5/2006 | White | |
| 7,160,328 B2 | 1/2007 | Rockwood, Jr. | |
| 7,204,854 B2 | 4/2007 | Guederian | |
| 7,217,272 B2 | 5/2007 | Salyer | |
| 7,294,149 B2 | 11/2007 | Hozack | |
| 7,329,284 B2 | 2/2008 | Maroney | |
| 7,588,572 B2 | 9/2009 | White | |
| 7,621,962 B2 | 11/2009 | Lakin | |
| 7,670,382 B2 | 3/2010 | Parrott | |
| 7,780,669 B2 | 8/2010 | Lechot | |
| 7,815,685 B2 | 10/2010 | Farrar | |
| 7,867,234 B2 | 1/2011 | Collazo | |
| 7,892,287 B2 | 2/2011 | Deffenbaugh | |
| 8,007,538 B2 | 8/2011 | Gunther | |
| 8,038,719 B2 | 10/2011 | Gunther | |
| 8,048,161 B2 | 11/2011 | Guederian | |
| 8,080,063 B2 | 12/2011 | Ferrand | |
| 8,157,866 B2 | 4/2012 | Winslow | |
| 8,308,809 B2 | 11/2012 | Bishop | |
| 8,425,614 B2 | 4/2013 | Winslow | |
| 8,444,646 B2 | 5/2013 | Long | |
| 8,465,548 B2 | 6/2013 | Long | |
| 8,475,460 B1 | 7/2013 | Roger | |
| 8,480,674 B1 | 7/2013 | Roger | |
| 8,540,778 B2 | 9/2013 | Rhodes | |
| 8,556,980 B2 | 10/2013 | Deffenbaugh | |
| 8,591,592 B2 | 11/2013 | Dreyfuss | |
| 8,673,015 B2 | 3/2014 | Maroney | |
| 8,764,836 B2 | 7/2014 | De Wilde | |
| 8,778,028 B2 | 7/2014 | Gunther | |
| 8,870,962 B2 | 10/2014 | Roche | |
| 8,876,907 B2 | 11/2014 | Baptista | |
| 8,974,537 B2 | 3/2015 | Dreyfuss | |
| 8,986,309 B1 | 3/2015 | Murphy | |
| D730,522 S | 5/2015 | Goldberg | |
| 9,119,643 B2 | 9/2015 | Winslow | |
| 9,180,016 B2 | 11/2015 | Maroney | |
| 9,233,003 B2 | 1/2016 | Roche | |
| 9,237,894 B2 | 1/2016 | Hernandez | |
| 9,283,076 B2 | 3/2016 | Sikora | |
| 9,289,306 B2 | 3/2016 | Goldberg | |
| 9,345,578 B2 | 5/2016 | Collazo | |
| 9,351,844 B2 | 5/2016 | Walch | |
| D759,819 S | 6/2016 | Goldberg | |
| 9,370,428 B2 | 6/2016 | Winslow | |
| 9,433,507 B2 | 9/2016 | Reubelt | |
| 9,474,619 B2 | 10/2016 | Reubelt | |
| 9,610,166 B2 | 4/2017 | Gunther | |
| 9,775,716 B2 | 10/2017 | Goldberg | |
| 9,814,471 B2 | 11/2017 | Goldberg | |
| 9,814,588 B2 | 11/2017 | Goldberg | |
| D810,940 S | 2/2018 | Goldberg | |
| D835,276 S | 12/2018 | Humphrey | |
| 10,524,922 B2 | 1/2020 | Courtney, Jr. | |
| 2002/0077702 A1 | 6/2002 | Castro | |
| 2003/0134252 A1 | 7/2003 | Sussman | |
| 2003/0187449 A1 | 10/2003 | McCleary | |
| 2003/0204263 A1 | 10/2003 | Justin | |
| 2004/0117027 A1 | 6/2004 | Reiley | |
| 2005/0015093 A1 | 1/2005 | Suh | |
| 2005/0038444 A1 | 2/2005 | Binder | |
| 2005/0049709 A1 | 3/2005 | Tornier | |
| 2005/0060039 A1 | 3/2005 | Cyprien | |
| 2005/0222572 A1 | 10/2005 | Chana | |
| 2005/0261775 A1 | 11/2005 | Baum | |
| 2006/0030946 A1 | 2/2006 | Ball | |
| 2006/0069443 A1 | 3/2006 | Deffenbaugh | |
| 2006/0074430 A1 | 4/2006 | Deffenbaugh | |
| 2006/0094958 A1 | 5/2006 | Marquart | |
| 2006/0100637 A1 | 5/2006 | Rathbun | |
| 2006/0111787 A1 | 5/2006 | Bailie | |
| 2007/0055380 A1 | 3/2007 | Berelsman | |

(56) References Cited

U.S. PATENT DOCUMENTS

| | | |
|---|---|---|
| 2007/0142917 A1 | 6/2007 | Roche |
| 2007/0219637 A1 | 9/2007 | Berelsman |
| 2007/0219638 A1 | 9/2007 | Jones |
| 2008/0058948 A1 | 3/2008 | Biegun |
| 2008/0109000 A1 | 5/2008 | Maroney |
| 2008/0147070 A1 | 6/2008 | Michel |
| 2008/0188855 A1 | 8/2008 | Brown |
| 2008/0287952 A1 | 11/2008 | Mcminn |
| 2008/0294266 A1* | 11/2008 | Steinberg ............ A61F 2/30756 623/22.21 |
| 2009/0005798 A1 | 1/2009 | Brunner |
| 2009/0018664 A1 | 1/2009 | Kropf |
| 2009/0138016 A1* | 5/2009 | Berthusen ........... A61B 17/1666 606/80 |
| 2009/0192621 A1 | 7/2009 | Winslow |
| 2009/0226068 A1 | 9/2009 | Fitz |
| 2009/0228114 A1 | 9/2009 | Clark |
| 2009/0240333 A1 | 9/2009 | Trudeau |
| 2009/0312839 A1 | 12/2009 | Scheker |
| 2010/0049327 A1 | 2/2010 | Isch |
| 2010/0087876 A1 | 4/2010 | Gunther |
| 2010/0087877 A1 | 4/2010 | Gunther |
| 2010/0094429 A1 | 4/2010 | Otto |
| 2010/0161065 A1 | 6/2010 | Williams, Jr. |
| 2010/0228352 A1 | 9/2010 | Courtney, Jr. |
| 2010/0241235 A1 | 9/2010 | Basamania |
| 2010/0268239 A1 | 10/2010 | Sikora |
| 2011/0098710 A1* | 4/2011 | Spratt ................ A61B 17/1671 606/80 |
| 2011/0106266 A1 | 5/2011 | Schwyzer |
| 2011/0144760 A1 | 6/2011 | Wong |
| 2011/0190898 A1 | 8/2011 | Lenz |
| 2011/0230972 A1 | 9/2011 | Katrana |
| 2011/0276144 A1 | 11/2011 | Wirth |
| 2012/0130500 A1 | 5/2012 | Maroney |
| 2012/0209392 A1 | 8/2012 | Angibaud |
| 2012/0221112 A1 | 8/2012 | Lappin |
| 2012/0239156 A1 | 9/2012 | De Wilde |
| 2012/0310360 A1 | 12/2012 | Parrott |
| 2012/0330429 A1 | 12/2012 | Axelson, Jr. |
| 2013/0024000 A1 | 1/2013 | Bojarski |
| 2013/0090737 A1 | 4/2013 | Flaherty |
| 2013/0144393 A1 | 6/2013 | Mutchler |
| 2013/0166033 A1 | 6/2013 | Gunther |
| 2013/0190827 A1 | 7/2013 | Butters |
| 2013/0204254 A1* | 8/2013 | Slone ................ A61B 17/1666 606/81 |
| 2013/0309030 A1 | 11/2013 | Winslow |
| 2014/0128983 A1 | 5/2014 | Flaherty |
| 2014/0163565 A1 | 6/2014 | Bollinger |
| 2015/0320567 A1 | 11/2015 | Terrill |
| 2015/0335440 A1 | 11/2015 | Linares |
| 2016/0089164 A1 | 3/2016 | Winslow |
| 2016/0095607 A1 | 4/2016 | Hernandez |
| 2016/0143637 A1 | 5/2016 | Nering |
| 2016/0242921 A1 | 8/2016 | Walch |
| 2016/0287266 A1 | 10/2016 | Sikora |
| 2017/0014238 A1 | 1/2017 | Reubelt |
| 2017/0151061 A1 | 6/2017 | Lavi |
| 2017/0231642 A1* | 8/2017 | Chaney .............. A61B 17/1764 606/80 |
| 2017/0239058 A1 | 8/2017 | Goldberg |
| 2017/0273795 A1 | 9/2017 | Neichel |
| 2017/0319348 A1 | 11/2017 | Goldberg |
| 2017/0348112 A1 | 12/2017 | Goldberg |
| 2018/0028323 A1 | 2/2018 | Servidio |
| 2018/0303619 A1 | 10/2018 | Kehres |
| 2019/0350717 A1 | 11/2019 | Tuttle |
| 2020/0038194 A1 | 2/2020 | Kester |

FOREIGN PATENT DOCUMENTS

| | | |
|---|---|---|
| AU | 2015204637 | 8/2016 |
| CA | 2821529 | 1/2014 |
| CA | 2941440 | 10/2014 |
| CA | 2972664 | 7/2015 |
| DE | 10130796 | 1/2003 |
| DE | 10134511 | 2/2003 |
| EP | 1518519 | 3/2005 |
| EP | 1159939 | 7/2005 |
| EP | 2238949 | 10/2010 |
| EP | 2446859 | 5/2012 |
| EP | 2559406 | 2/2013 |
| EP | 2689751 | 1/2014 |
| EP | 2967892 | 1/2016 |
| EP | 3091940 | 11/2016 |
| EP | 3284442 | 2/2018 |
| FR | 2825263 | 12/2002 |
| FR | 2836821 | 5/2004 |
| GB | 2308068 | 9/1999 |
| IN | 201508960 | 7/2016 |
| IN | 201617026041 | 8/2016 |
| WO | WO1998015241 | 4/1998 |
| WO | WO2000018335 | 4/2000 |
| WO | WO2002017822 | 3/2002 |
| WO | WO2006110896 | 10/2006 |
| WO | WO2007109800 | 9/2007 |
| WO | WO2009108591 | 9/2009 |
| WO | WO2011029911 | 3/2011 |
| WO | WO2012030794 | 3/2012 |
| WO | WO2013020026 | 2/2013 |
| WO | WO2014005644 | 1/2014 |
| WO | WO2014164265 | 10/2014 |
| WO | WO2015106136 | 7/2015 |
| WO | WO2018017615 | 1/2018 |

* cited by examiner

OFFSET REAMERS

CROSS-REFERENCE TO RELATED APPLICATIONS

The present application claims the benefit of:

U.S. Provisional Patent Application No. 62/470,792, entitled OFFSET REAMERS, which was filed on Mar. 13, 2017.

The present application is a continuation-in-part of:

U.S. patent application Ser. No. 15/660,942, entitled STABILIZED DRILL GUIDE, which was filed on Jul. 26, 2017.

U.S. patent application Ser. No. 15/660,942 claims the benefit of:

U.S. Provisional Patent Application No. 62/367,533, entitled STABILIZED DRILL GUIDE, which was filed on Jul. 27, 2016.

U.S. patent application Ser. No. 15/660,942 is a continuation-in-part of:

U.S. patent application Ser. No. 14/042,258, entitled GLENOID ARTHROPLASTY, which was filed on Sep. 30, 2013;

U.S. patent application Ser. No. 15/587,895, entitled GLENOID ARTHROPLASTY, which was filed on May 5, 2017;

U.S. patent application Ser. No. 14/592,837, entitled GLENOID ARTHROPLASTY AND OFFSET REAMERS, which was filed on Jan. 8, 2015;

U.S. patent application Ser. No. 15/228,443, entitled GLENOID ARTHROPLASTY WITH MULTI-DIRECTIONAL FIXATION, which was filed on Aug. 4, 2016; and U.S. patent application Ser. No. 15/653,305, entitled ARTHROPLASTY PROSTHESES WITH MULTI-AXIS FIXATION, which was filed on Jul. 18, 2017.

U.S. patent application Ser. No. 14/042,258 claims the benefit of:

U.S. Provisional Patent Application No. 61/776,398, entitled OBLIQUE-INSERTION ANCHORING MECHANISM FOR GLENOID PROSTHETIC COMPONENT, which was filed on Mar. 11, 2013.

U.S. patent application Ser. No. 15/587,895 is a continuation of U.S. patent application Ser. No. 14/042,258.

U.S. patent application Ser. No. 14/592,837 claims the benefit of:

U.S. Provisional Patent Application No. 61/925,893, entitled OFFSET REAMERS, which was filed on Jan. 10, 2014.

U.S. patent application Ser. No. 14/592,837 is a continuation-in-part of U.S. patent application Ser. No. 14/042,258.

U.S. patent application Ser. No. 15/228,443 claims the benefit of:

U.S. Provisional Patent Application No. 62/203,255, entitled GLENOID ARTHROPLASTY WITH MULTI-DIRECTIONAL FIXATION, which was filed on Aug. 10, 2015.

U.S. patent application Ser. No. 15/653,305 claims the benefit of:

U.S. Provisional Patent Application No. 62/363,607, entitled ARTHROPLASTY PROSTHESES WITH MULTI-AXIS FIXATION, which was filed on Jul. 18, 2016.

U.S. patent application Ser. No. 15/653,305 is a continuation-in-part of U.S. patent application Ser. No. 15/228,443.

The foregoing are incorporated by reference as though set forth herein in their entirety.

BACKGROUND

The present disclosure relates to reamers for human or veterinary implants. The disclosed reamers are useful in situations where exposure is difficult, the implantation trajectory is oblique to the implantation site, or the implantation site is tapered, conical, or wedge-shaped. For example, the disclosed anchoring elements are useful in the context of a glenoid implant for shoulder arthroplasty, so that the preparation of the glenoid and implantation of the glenoid component take place along an oblique surgical access and implantation trajectory. An oblique approach, or an anterolateral approach, to the glenoid is technically simpler and less invasive than a lateral trajectory to the glenoid. This disclosure is made in the context of a glenoid component for shoulder arthroplasty for the purpose of illustrating the relevant principles of the technology. However, the principles disclosed herein are applicable to other surgical sites throughout the body, such as the acetabulum of the hip joint.

In total shoulder arthroplasty, a glenoid implant is attached to a prepared glenoid or scapula, and a humeral implant is attached to a prepared humerus. The humeral implant usually includes a ball or convex articular surface at a proximal end thereof which engages and moves relative to a socket or concave articular surface formed in a lateral aspect of the glenoid implant, although this arrangement is sometimes reversed so that the humeral implant includes the convex articular surface and the glenoid implant includes the convex articular surface. The ligaments and muscles of the shoulder surround the implants and maintain the humeral implant against the glenoid implant, while at the same time allowing relative movement therebetween.

In shoulder arthroplasty, the humeral head is in close proximity to the glenoid. The humeral head can interfere with an axial reamer (a conventional straight shaft instrument whose cutting face is perpendicular to the shaft axis) for preparation of the glenoid socket. Similar conditions exist in other joints of the body, such as the elbow, wrist, hip, knee, ankle, or joints of the hand, foot, spine, jaw, or pelvis. Tight joint spaces or interfering bony or soft tissue structures may be dealt with by increasing the size of the surgical incision, performing more extensive dissection to increase exposure of the surgical site, or using retractors or other tools to move interfering structures out of the way, but these techniques increase surgical trauma to the joint, increase the risk of collateral damage beyond that essential to the arthroplasty procedure, and may destabilize the reconstructed joint.

Current instruments for standard glenoid arthroplasty, including drill bits, reamers, and trial implant components, and final implant components are frequently designed for the surgeon to approach the scapula along a direction perpendicular to the face of the glenoid portion of the scapula; this may be referred to as a direct lateral trajectory. However, the standard incisions and safest surgical approach for glenoid arthroplasty provide exposure for the surgeon which is more oblique, or antero-lateral. In order to facilitate the insertion of instruments perpendicular to the face of the glenoid, the surgeon may find it necessary to resect the articular portion of the humeral head and forcefully retract the patient's skin, muscle and remaining humerus out of the way posteriorly to obtain adequate exposure. In doing so, the surgeon may potentially injure nerves or blood vessels. Often the surgeon will purposely cut the biceps tendon or portions of the pectoralis major tendon to improve exposure to facilitate this step, as well as releasing the glenohumeral ligaments. All of this dissection, retraction, and removal of bone and soft tissue is done in order to allow the surgeon enough room to implant the glenoid prosthetic component.

Reamers are used in various medical procedures to prepare or shape bone surfaces. For example, reamers are used in various joint arthroplasty procedures. One example of an arthroplasty procedure is shoulder arthroplasty. Reamers may be used in shoulder arthroplasty procedures to prepare or shape bone surfaces on the glenoid or on the humeral head. Another example is hip arthroplasty. Reamers may be used in hip arthroplasty procedures to prepare or shape bone surfaces in the acetabulum or on the femoral head. Reamers may be used to prepare or shape bone surfaces which are planar, concave, convex, spherical, conical, or other surfaces of revolution.

There is a need for reamers adapted for use in tight joint spaces, which would need little to no joint distraction, dissection, retraction, or exposure. This disclosure presents four reamers, each adapted for use in tight joint spaces by having an offset shaft arrangement.

Other objectives and advantages of this technology will become apparent from the following description taken in conjunction with the accompanying drawings which illustrate examples of this technology. The drawings constitute a part of this specification and include examples of the present technology and illustrate various objects and features thereof.

BRIEF DESCRIPTION OF THE DRAWINGS

While examples of the present technology are shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is to be defined by the following claims, along with the full range of equivalents to which such claims are entitled.

Identical reference numerals do not necessarily indicate an identical structure. Rather, the same reference numeral may be used to indicate a similar feature or a feature with similar functionality. Not every feature of each example is labeled in every figure in which that example appears, in order to keep the figures clear. Similar reference numbers (e.g., those that are identical except for the first numeral) are used to indicate similar features in different examples.

DETAILED DESCRIPTION

Figure 1:
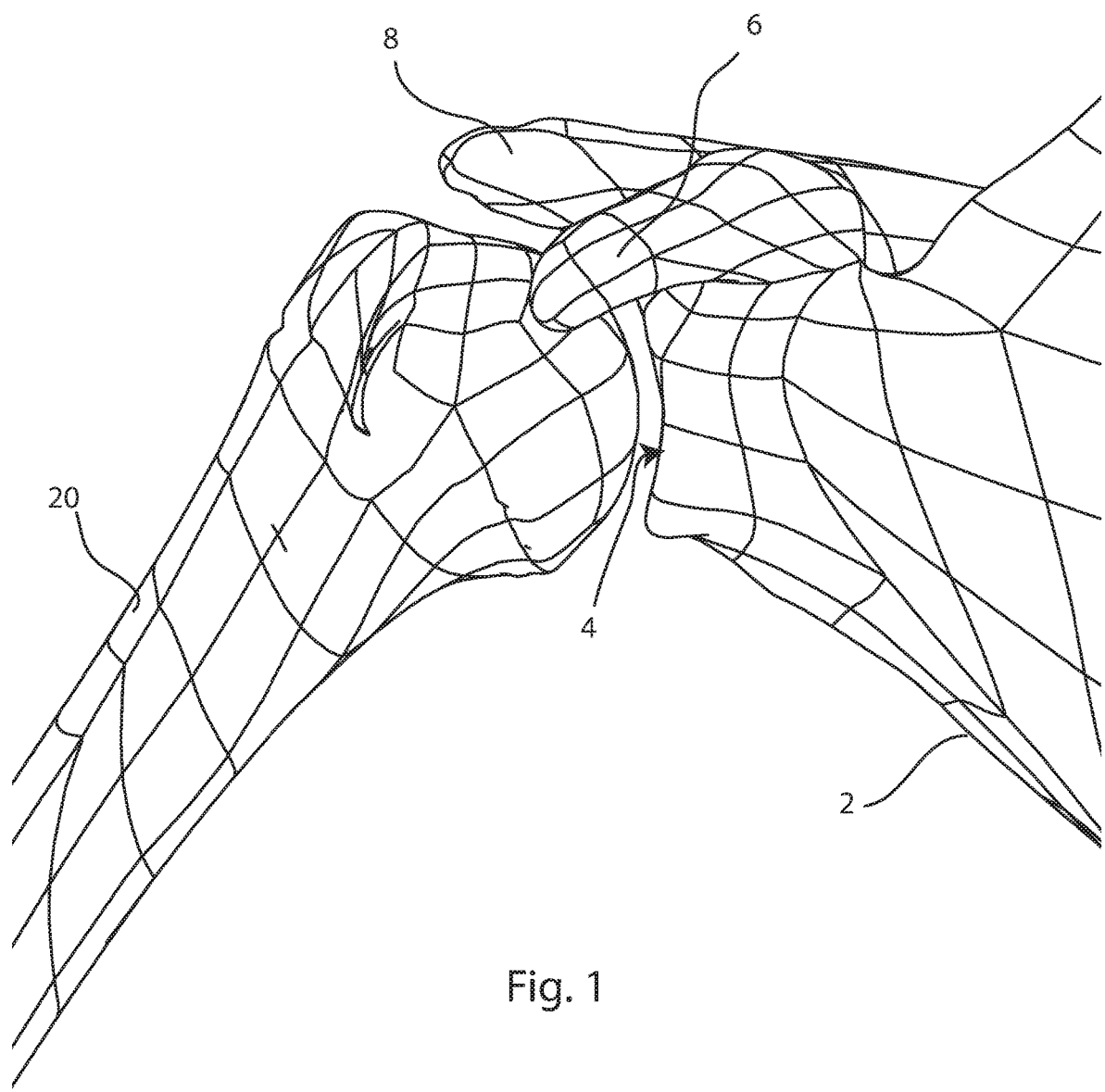
FIG. 1 is an anterior view of a right shoulder joint with a scapula and a humerus.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative exemplary of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

In this specification, an axis is a straight line which has infinite length, zero breadth, and zero thickness. An object may rotate about an axis or move along an axis. Two coplanar axes are collinear if they have more than one point in common; in fact, all of their points are in common. Two coplanar axes intersect if they have exactly one point in common. Two coplanar axes are parallel if they have zero points in common. Two non-coplanar axes are skew if they do not intersect and are not parallel; they also have zero points in common.

In this specification, polyaxial means movement which occurs about multiple axes. Polyaxial and multiaxial are synonymous. A ball-and-socket joint is one example of a joint which provides polyaxial movement about a point, a center point of rotation. The range of motion of a polyaxial joint may be conical, wherein the vertex of the cone lies at the center point of rotation of the polyaxial joint. The range of motion of a polyaxial joint may be expressed as the included angle of the cone, or as the half-angle of the cone. The skeleton includes polyaxial joints, such as the shoulder joint and the hip joint.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Standard shoulder anatomical terms are employed with their ordinary and customary meanings.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Coatings may be present. Different materials may be used within a single part. Any component disclosed herein may be colored, coded or otherwise marked to make it easier for a user to identify the type and size of the component, the setting, the function(s) of the component, and the like.

Figure 2:
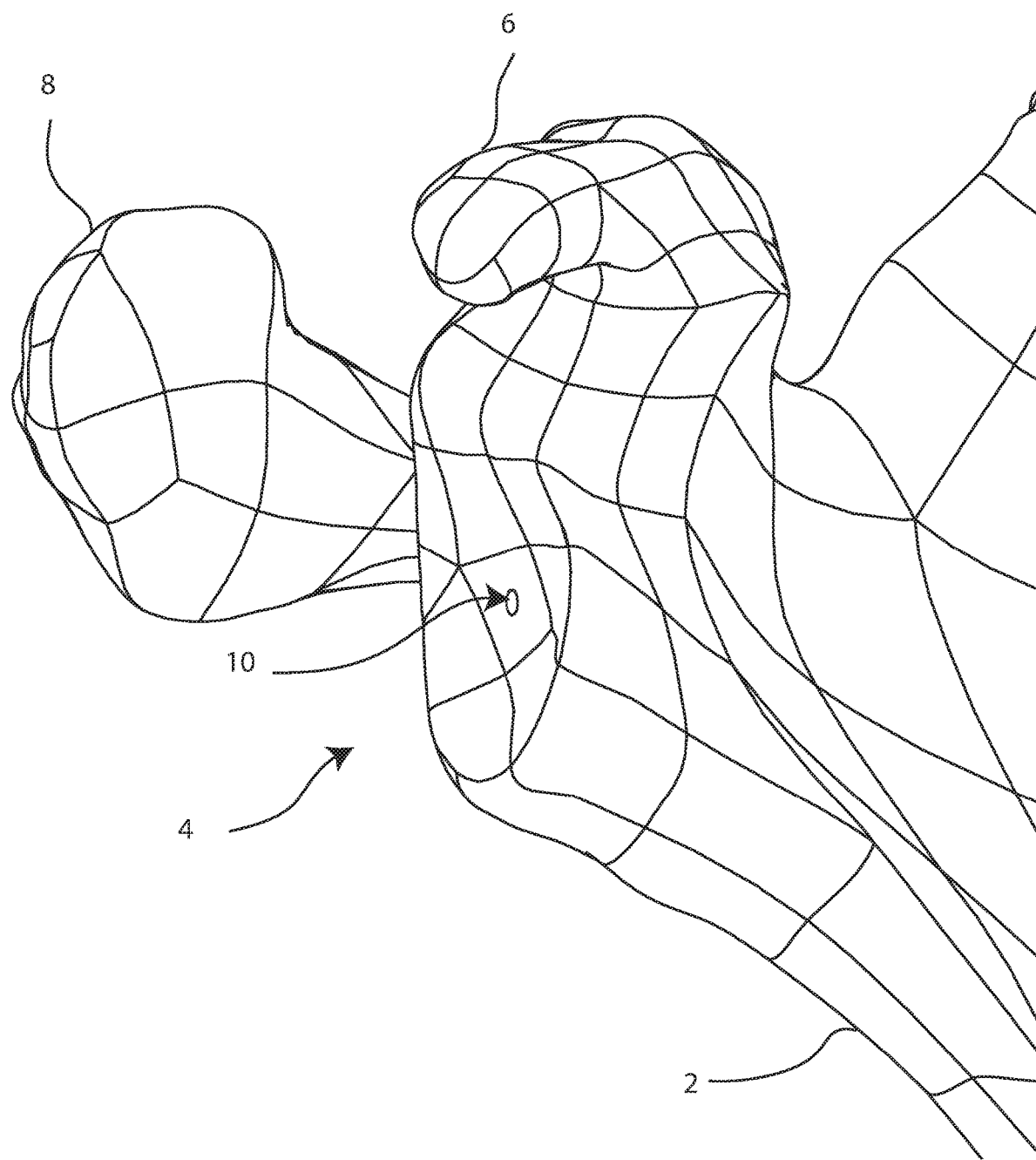
FIG. 2 is an isometric view of the scapula of FIG. 1 after sizing and forming a pilot hole in the glenoid fossa.
Figure 3:
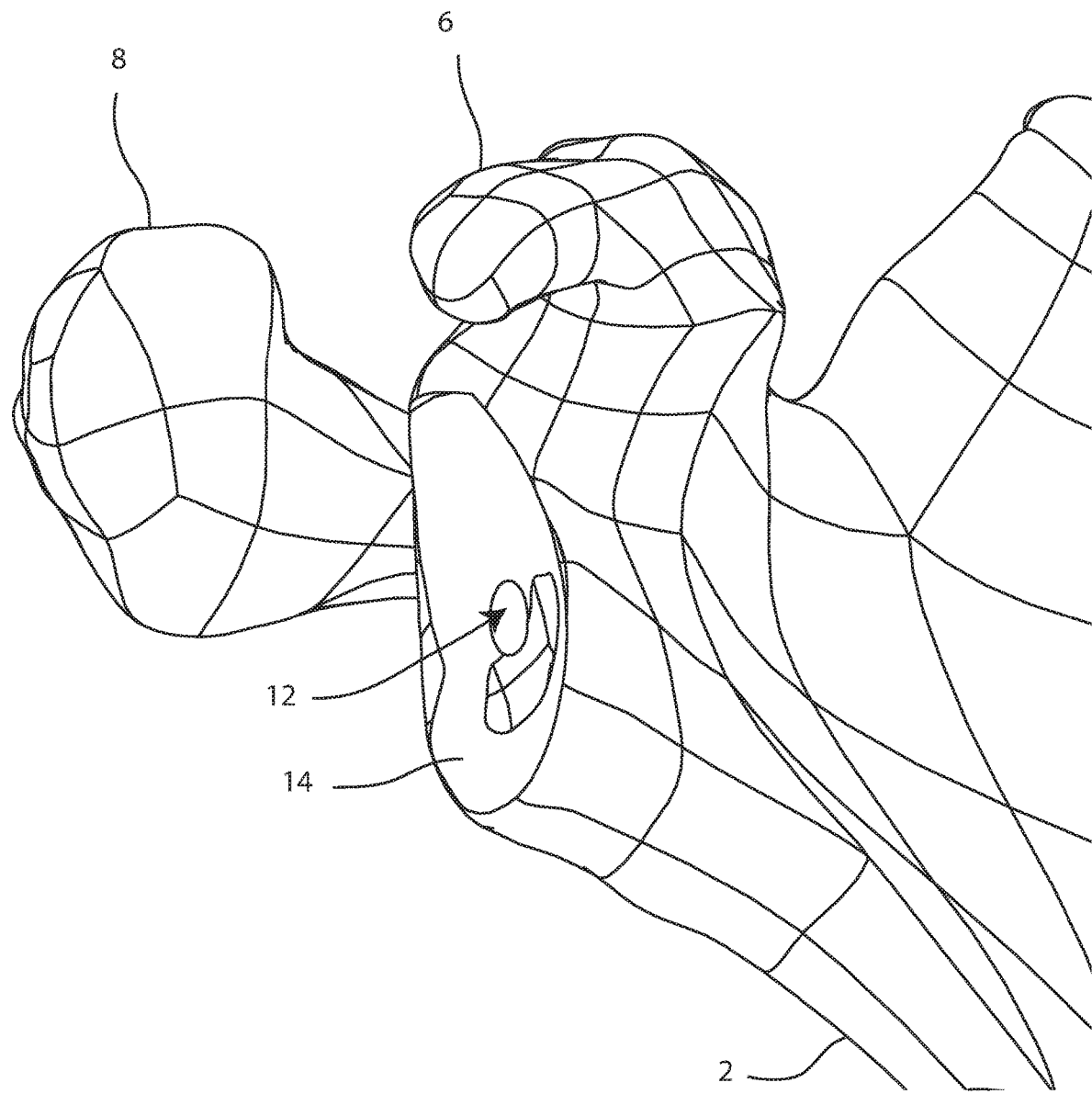
FIG. 3 is an isometric view of the scapula of FIG. 2 after reaming.

FIGS. 1-3, and the corresponding description below, come from U.S. patent application Ser. No. 14/042,258, which is incorporated herein by reference in its entirety.

Referring to FIGS. 1-3, a method of using a reamer to prepare an implantation site for a glenoid component will be described. One of skill in the art will appreciate that there are many methods for preparing a glenoid to receive a glenoid component, and that the method shown below represent an example of the methods available. Other methods contemplated may include the use of a saw, such as a reciprocating or oscillating saw; a burr, which may be motorized; a punch; an osteotome; and/or a curette, used alone or in combination with one or more drills, guides, and/or cutting jigs. These tools may be used to prepare the glenoid to receive a glenoid component.

FIG. 1 illustrates a normal intact right shoulder joint including a scapula 2 and a humerus 20 in an anterior view. The scapula 2 includes a glenoid fossa 4, a coracoid process 6, and an acromion process 8.

FIG. 2 shows the scapula 2 after the step of forming a pilot hole 10 in the glenoid fossa 4. A small drill or reamer (not shown) may be used to form the pilot hole 10.

FIG. 3 shows the scapula 2 after the step of reaming the glenoid fossa 4 with a reamer. Any of the reamers disclosed herein may be used to ream the glenoid fossa 4. The pilot hole 10 may be enlarged during this step to form hole 12. The glenoid fossa 4 is shown with a reamed surface 14.

The reamers disclosed herein may be used to prepare a bone bed to receive or support an arthroplasty implant. The prepared bone bed may be smooth. The reamers may engage a central pilot hole; the pilot hole may also be used to locate subsequent bone preparation guides and/or tools. The reamers may be designed with various offset shaft arrangements, such as the following examples, to adapt the reamers for use in tight joint spaces where a conventionally designed reamer would meet with interference from body structures. In one example, the disclosed reamers may be used for glenoid preparation in shoulder arthroplasty. In this example, one interfering structure is the humeral head. Of course, the disclosed reamers may also be used in other arthroplasty procedures for other skeletal joints.

Design objectives for the disclosed reamers include: prepare a smooth surface of revolution, where the axis of revolution of the surface may be perpendicular to the natural bony feature being reamed; minimize contact with surrounding body structures, such as the opposing bone of the joint, so that the reamer is not used as a pry bar to distract the joint; and ease of use equivalent to a conventional straight reamer. Any of the disclosed reamers may prepare the glenoid fossa 4 of the scapula 2 as shown in FIG. 3.

Offset reamers 2100 and 2200 were disclosed in U.S. patent application Ser. No. 14/592,837, which is incorporated herein by reference in its entirety.

Figure 4:
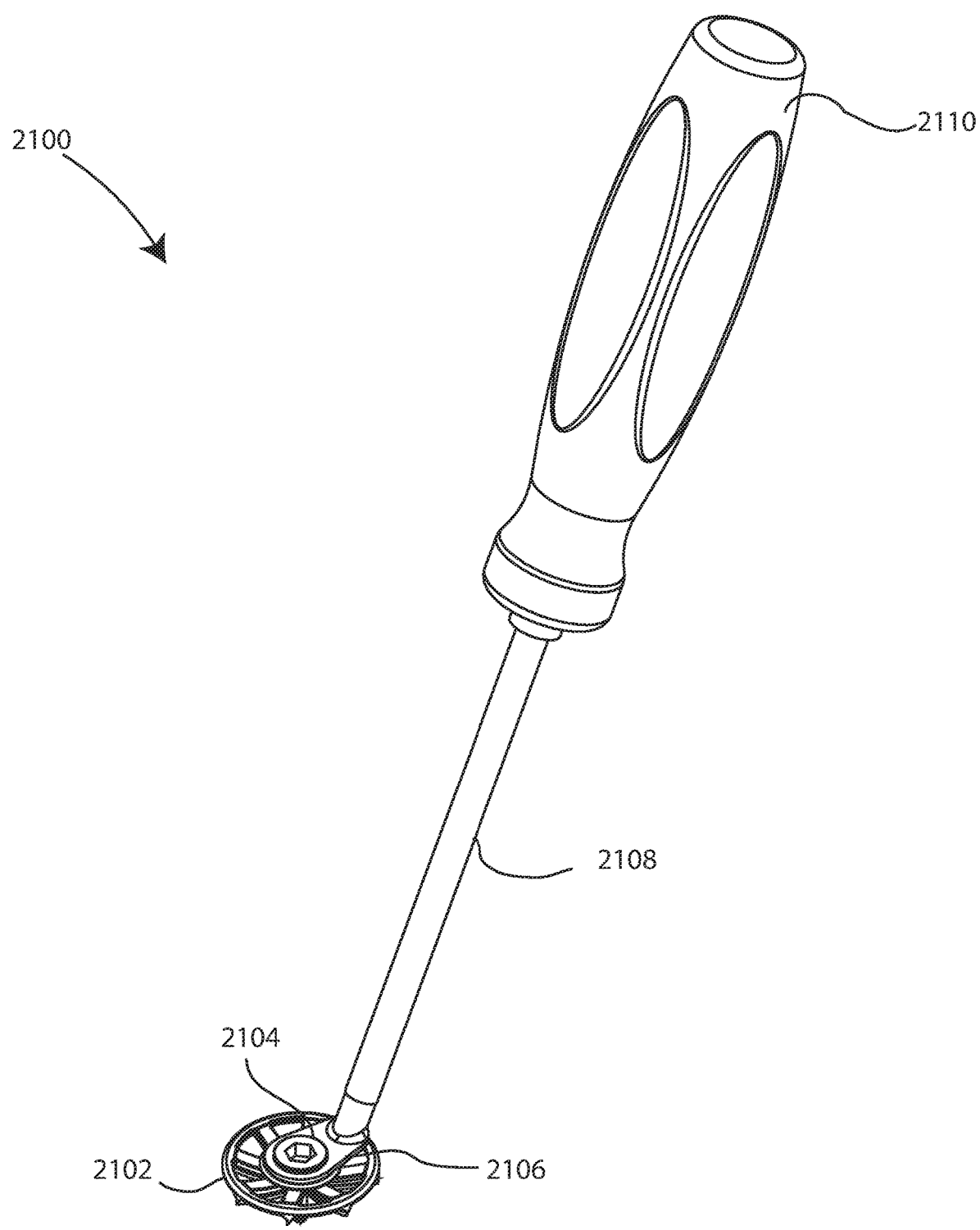
FIG. 4 is an isometric view of an offset reamer.

Referring to FIG. 4, an offset reamer 2100 includes a reamer head 2102, a reamer coupler 2104, a working tip 2106, a shaft 2108, and a handle 2110. FIGS. 4-10 show various views of offset reamer 2100.

Figure 5:
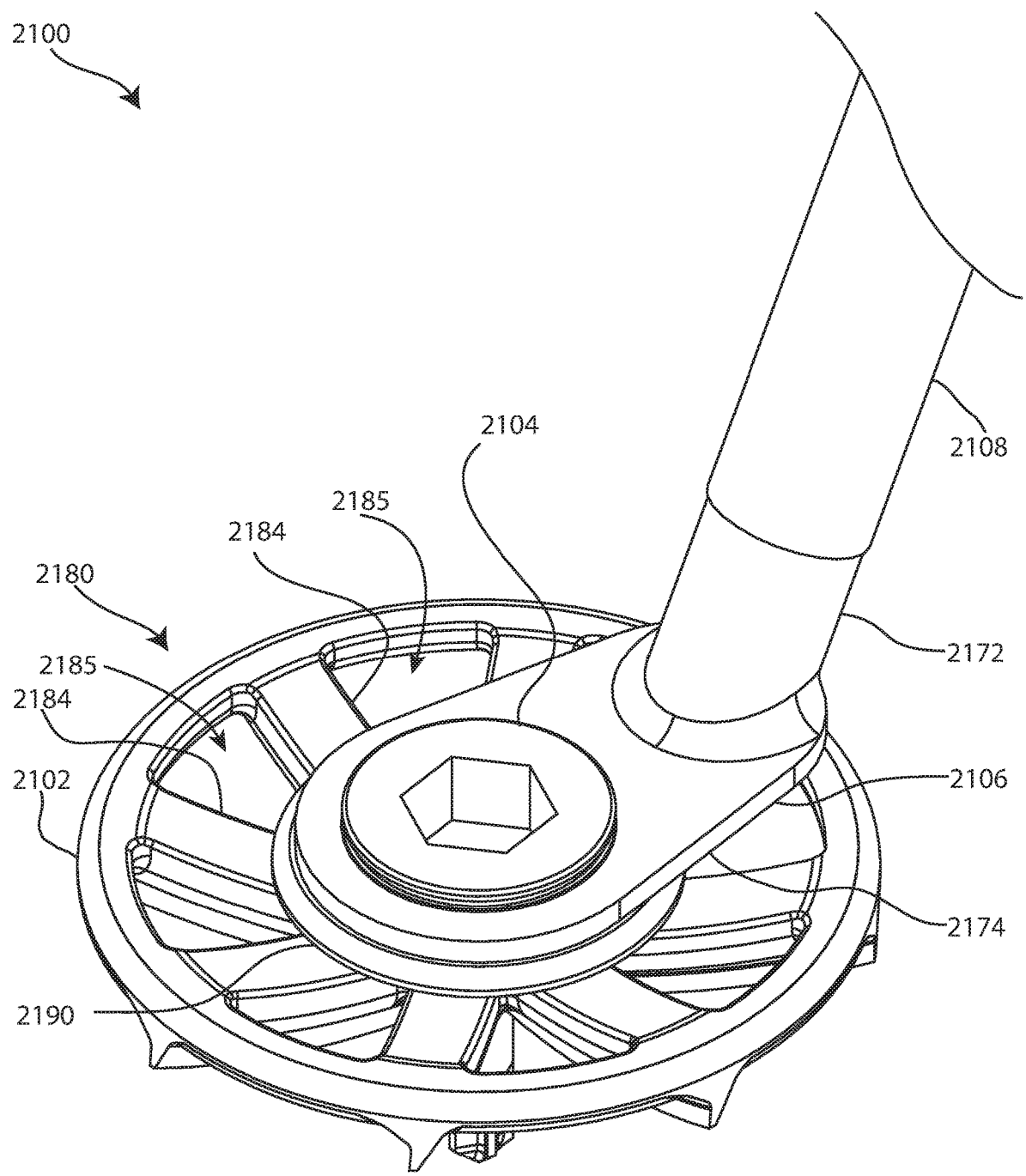
FIG. 5 is an isometric view of a portion of the offset reamer of FIG. 4.
Figure 6:
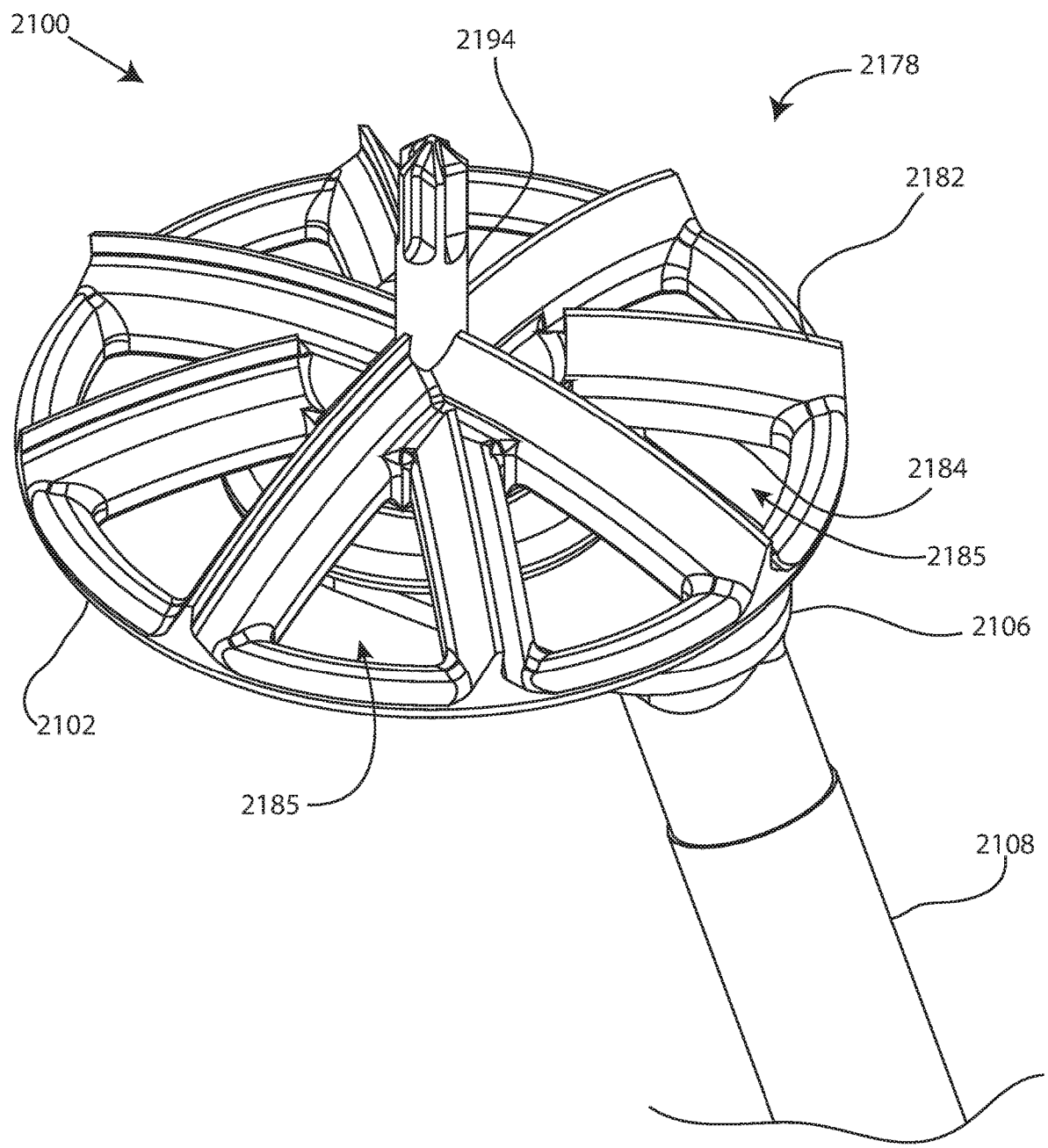
FIG. 6 is an isometric view of a portion of the offset reamer of FIG. 4 from a second viewpoint.
Figure 7:
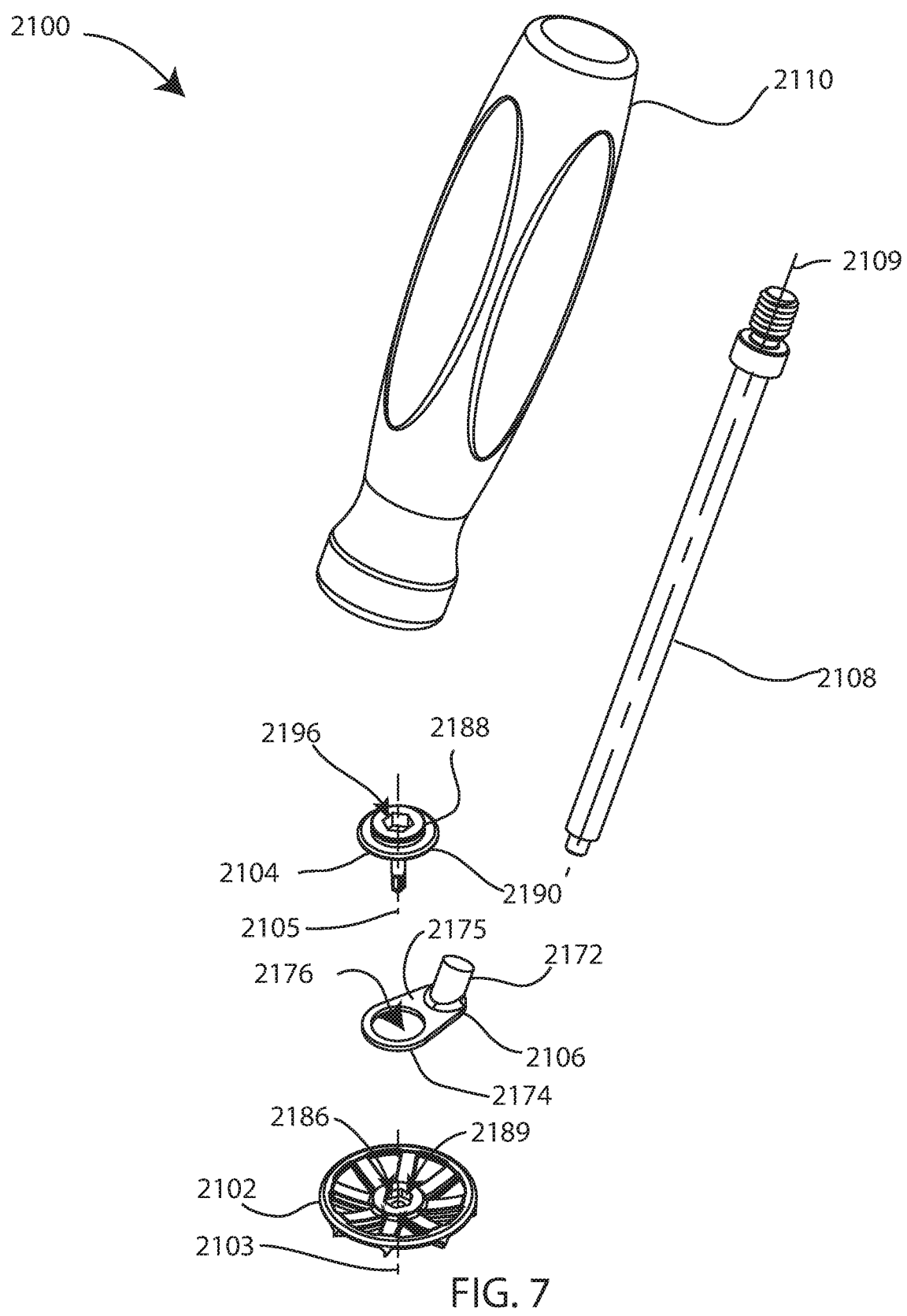
FIG. 7 is an isometric exploded view of the offset reamer of FIG. 4.

The reamer head 2102 is a round part with a central longitudinal rotational axis 2103, a convex obverse side 2178, or bone-facing side or cutting side (FIG. 6), and a reverse side 2180 (FIG. 5). The obverse side 2178 may be flat or concave in other examples devoted to other joints around the body. The obverse side 2178 includes bone removal features 2182, which may be teeth, serrations, ridges and grooves, knurling, a sandpaper texture, or the like. In the example shown, the bone removal features 2182 are sharpened edges on radial arms 2184 of the reamer head 2102. Eight arms 2184 are shown in the example, although any number of arms may be provided. The arms 2184 in the example are separated by windows 2185 or apertures. The reamer head 2102 includes a central aperture 2186 (FIGS. 7-8), which may include a drive portion 2189 adjacent to the reverse side 2180 and a circular portion adjacent to the obverse side 2178. The drive portion 2189 may be a hex socket, as illustrated in FIG. 7, or another configuration for torque transmission in at least one rotational direction. The drive portion 2189 may be referred to as a torque input feature for torque transmission to the reamer head 2102.

Figure 8:
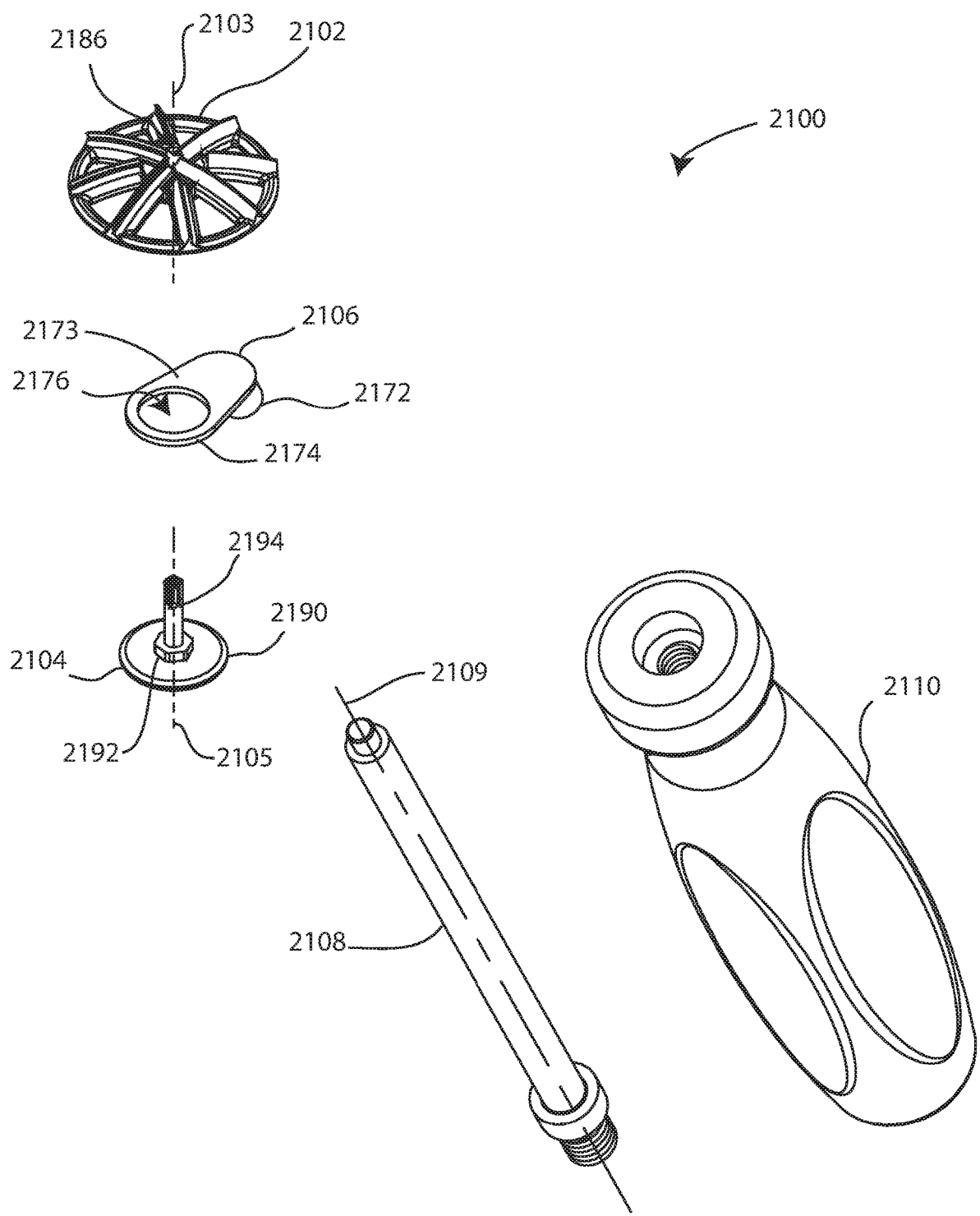
FIG. 8 is an isometric exploded view of the offset reamer of FIG. 4 from a second viewpoint.
Figure 9:
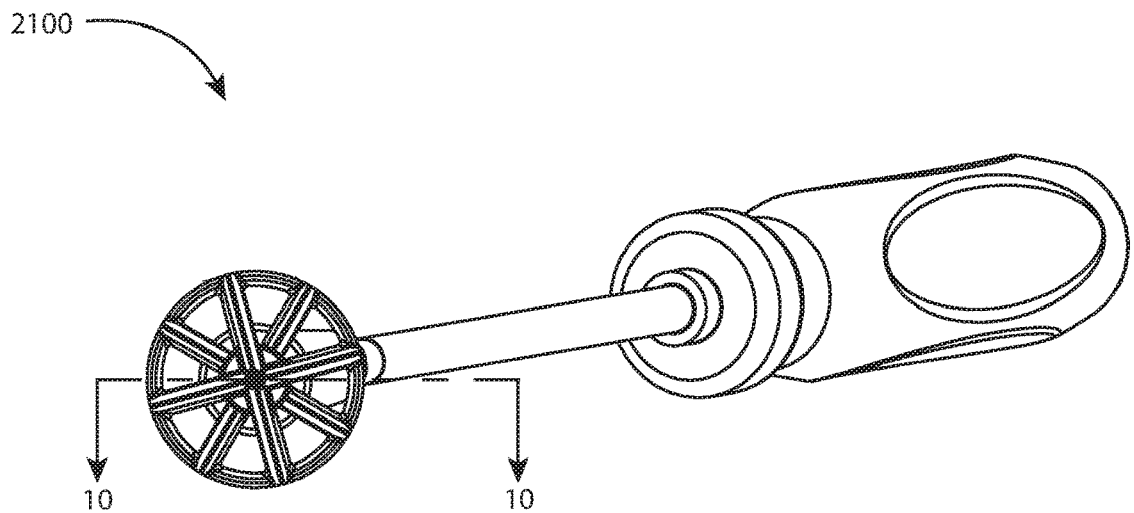
FIG. 9 is a bottom view of the offset reamer of FIG. 4.

Referring to FIGS. 7-8, the reamer coupler 2104 includes a central longitudinal rotational axis 2105, a head 2188, a flange 2190 under the head, a drive feature 2192 under the flange, and a shaft 2194 under the drive feature. The reamer coupler 2104 may be referred to as a coupling which connects the offset reamer 2100 to a prime mover or torque source such as a power driver or T-handle so that the reamer head 2102 may be rotated or spun about the axis 2103. The head 2188 may include a drive portion 2196, which may be a hex socket, as illustrated in FIG. 7, or another configuration for torque transmission in at least one rotational direction. The drive portion 2196 may be referred to as a torque input feature for torque transmission to the reamer coupler 2104. The depth of the drive portion 2196, or its height if it is a positive feature, is a matter of design choice balancing the polyaxial range of motion with the stability of the corresponding driver. The drive feature 2192 may be a hex key, as illustrated in FIG. 8, or another configuration for cooperation with the drive portion 2189 of the aperture 2186 of the reamer head 2102 for torque transmission in at least one rotational direction. The drive feature 2192 may be referred to as a torque output feature for torque transmission to the reamer head 2102. The shaft 2194 may include cutting flutes at least along the leading tip, and may therefore be called a drill tip. FIGS. 6 and 8 illustrate this configuration. The reamer coupler 2104 may include a cannulation extending along the axis 2105 through the shaft 2194 or, in other examples, instead of the shaft 2194. The cannulation, if present, receives a k-wire, guide wire, bone pin, or the like so that the reaming surface can be fixed to a particular location, orientation, or trajectory in the glenoid or, in the case of a biconcave glenoid, so that the reaming surface can sequentially be fixed to multiple locations, orientations, or trajectories. The shaft 2194 may be spring loaded, and may be biased to be normally extended or normally retracted. In the latter situation, the shaft 2194 may only extend outwardly when a driver (discussed below) is engaged with the drive portion 2196.

The working tip 2106 may be coupled to one end of the shaft 2108 and the handle 2110 may be coupled to the other end of the shaft 2108 to form a handle assembly. The working tip 2106, the shaft 2108, and the handle 2110 may be permanently or temporarily coupled together. For example, the working tip 2106 and/or handle 2110 may be permanently welded to the shaft 2108. Alternatively, the working tip 2106 and/or handle 2110 may be temporarily threaded or snapped to the shaft 2108. The working tip 2106 includes a shaft portion 2172 for connection to the shaft 2108 and a plate portion 2174 that extends obliquely from the shaft portion. The shaft 2108 includes a central longitudinal axis 2109, with which the shaft portion 2172 aligns when the shaft 2108 and the shaft portion 2172 are connected. While the illustrated shaft 2108 is straight, in other examples the shaft may be curved or bent to be more functional or ergonomic according to the particular surgical site in which it will be used. The shaft portion 2172 and the shaft 2108 may include a cannulation extending along the axis 2109. The cannulation, if present, receives a k-wire, guide wire, bone pin, or the like so that the reaming surface can be fixed to a particular location, orientation, or trajectory in the glenoid or, in the case of a biconcave glenoid, so that the reaming surface can sequentially be fixed to multiple locations, orientations, or trajectories. The plate portion 2174 includes an obverse side 2173, or bone-facing side, and a reverse side 2175 opposite the bone-facing side. The plate portion is pierced by an aperture 2176 or hole which may extend through the obverse side 2173 and the reverse side 2175.

Figure 10:
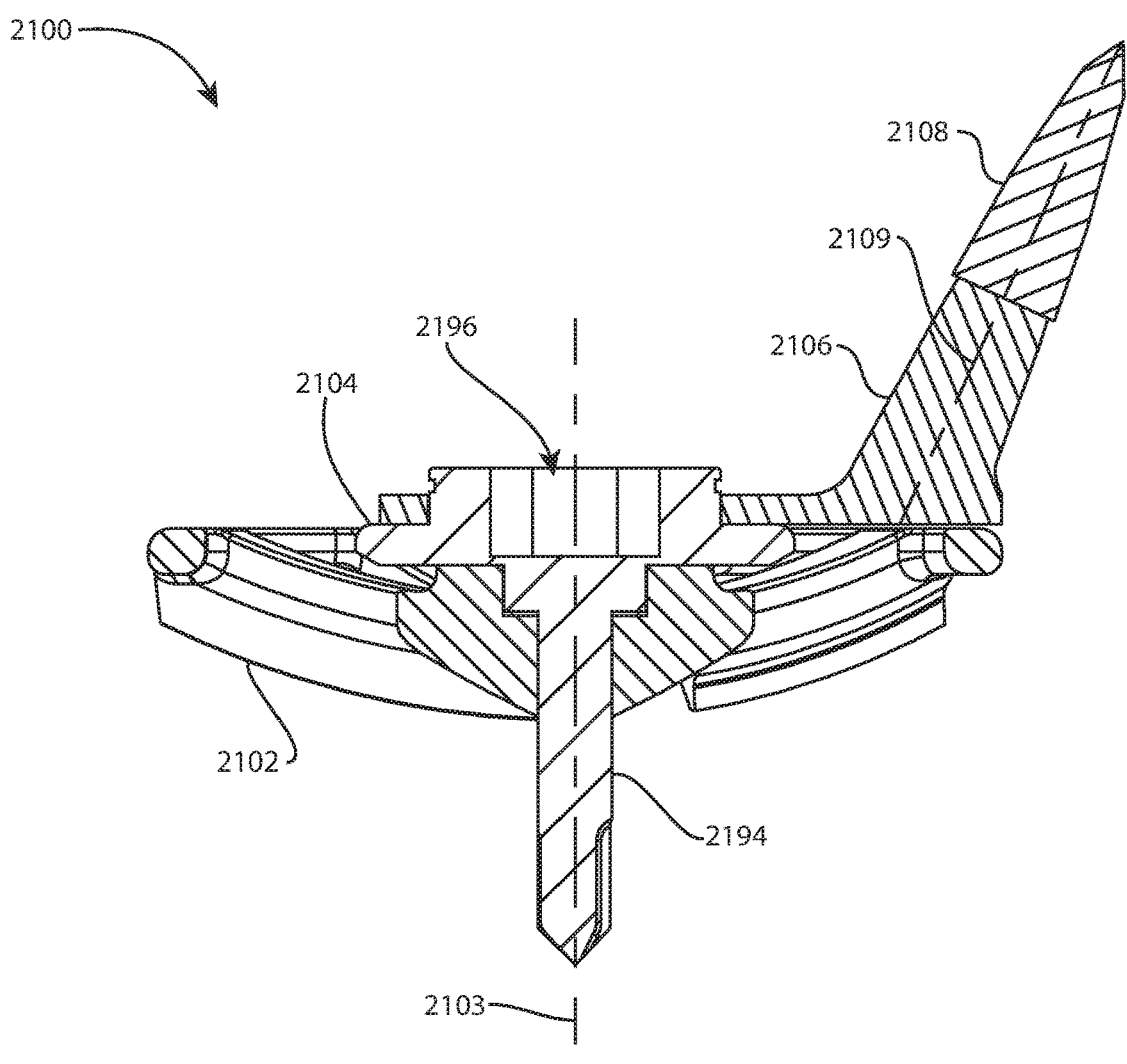
FIG. 10 is a cross sectional view through a portion of the offset reamer of FIG. 4, taken along line 10-10 of FIG. 9.

Referring to FIG. 10, the reamer head 2102, the reamer coupler 2104, and the working tip 2106 are operatively assembled by inserting the head 2188 through the aperture 2176 so that the flange 2190 contacts the bone-facing side 2173 of the plate portion 2174, and inserting the shaft 2194 through the circular portion of the aperture 2186 of the reamer head 2102 so that the drive feature 2192 engages the drive portion of the aperture 2186 of the reamer head 2102; in the illustrated example, this involves inserting the hex key 2192 into the hex socket drive portion 2189 of aperture 2186. The working tip 2106 may be said to carry the reamer coupler 2104 and the reamer head 2102. The head 2188, the plate portion 2174, the shaft 2194, the drive feature 2192, and/or the aperture 2186 may include a retention element, such as a ball detent, clip, retaining ring, groove, taper, twist, or the like, to keep the head 2188, the plate portion 2174, the shaft 2194, the drive feature 2192, and/or the aperture 2186 coupled together until intentionally disassembled. The operative assembly of the reamer head 2102, the reamer coupler 2104, and the working tip 2106 may be referred to as a working portion of the offset reamer 2100.

When the reamer head 2102, the reamer coupler 2104, and the working tip 2106 are operatively assembled, at least the reamer head 2102 and the reamer coupler 2104 may be rotationally coupled or fixed together with axes 2103, 2105 collinear. Together, the reamer head 2102 and the reamer coupler 2104 may rotate freely relative to the working tip 2106 about axis 2103. The handle assembly of the working tip 2106, the shaft 2108, and the handle 2110 may be manipulated by a user to control the location and orientation of the reamer axis 2103.

A driver, such as the reamer driver 2216 shown in FIGS. 11-17, may include a Hudson connector or torque bit which couples to a prime mover or torque source, such as a power driver or a T-handle. The tip of the driver may be directly engaged with the reamer coupler 2104, and the driver may be rotated by the prime mover about a central longitudinal rotational axis of the driver, or driver axis, to turn the reamer coupler 2104 and the reamer head 2102 about axis 2103. In other words, the driver may be rotationally coupled to the reamer coupler 2104 and the reamer head 2102. For example, the driver may have a straight hex key drive tip to engage the hex socket drive portion 2196 so that the driver axis is in line with, or coaxial with, the axis 2103. The driver may alternatively have a ball drive tip, such as the ball hex key drive tip 2220 shown in FIGS. 11-17, which permits the driver axis to be polyaxially obliquely angled, or polyaxially angularly offset, relative to the rotational axis 2103 of the reamer head 2102 in the manner discussed below for offset reamer 2200. In this example with the ball hex key drive tip, the driver axis may be described as being angularly offset from, or noncollinear with, the rotational axis 2103 of the reamer head 2102, so that the driver axis and the axis 2103 have no more than a single mathematical point in common, and that only if the driver axis and the axis 2103 intersect.

Therefore, the driver may be referred to as an offset driver or an offset drive shaft due to the unconstrained angular offset between the driver axis and the rotational axis 2103 of the reamer head 2102. The driver may alternatively include other adaptations to permit the driver to be obliquely angled, or angularly offset, relative to the rotational axis 2103 of the reamer head 2102, such as a universal joint, a flexible shaft portion, a bevel gear acting against the reamer head 2102 and/or the reamer coupler 2104, a ball Torx drive (hexalobular), a ball star drive, or various other ball polygonal or polylobular design. More specifically, the driver may have a ball drive tip with five or more corners or points, which may provide a smooth feel with less turbulence or kicking during actuation. While the ball hex key drive tip is an example which provides polyaxial angular offset, other examples may provide a fixed angular offset. In use, the driver may be angularly repositioned relative to the axis 2103 at any time the user desires, whether or not the driver is being actuated or rotated. The driver may be repositioned independently of any manipulation of the reamer head axis 2103 or the handle assembly, so that the angular offset between the axis 2103 and the driver axis is continuously variable.

Figure 11:
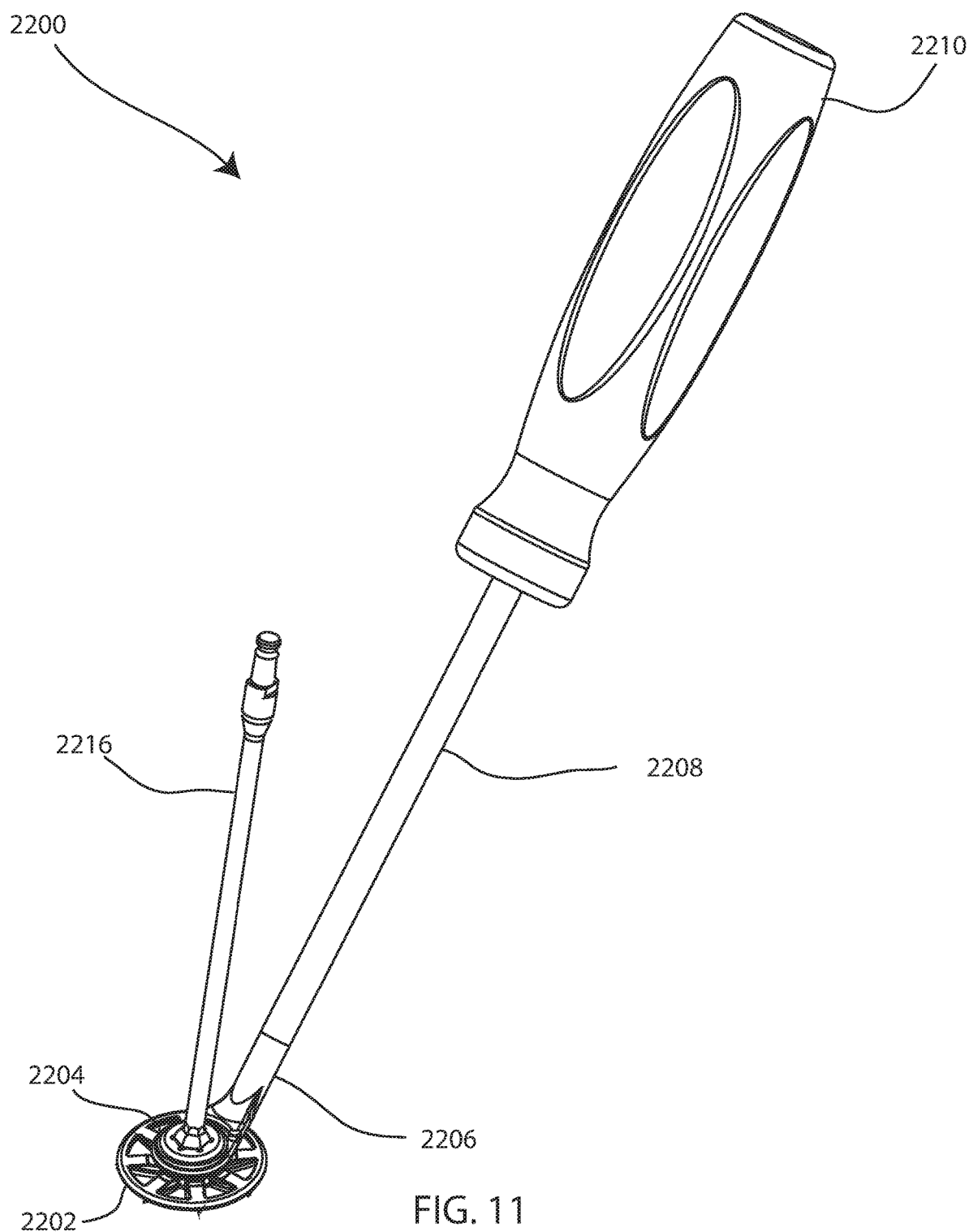
FIG. 11 is an isometric view of another offset reamer.

Referring to FIG. 11, another offset reamer 2200 includes a reamer head 2202, a reamer coupler 2204, a working tip 2206, a shaft 2208, and a handle 2210. FIGS. 11-17 show various views of offset reamer 2200. Offset reamer 2200 also includes a first bushing 2212 and a second bushing 2214, which are seen best in FIGS. 14, 15, and 17. Offset reamer 2200 is shown with a reamer driver 2216, which may be used interchangeably with offset reamers 2100, 2200, 2300, 2400.

Figure 12:
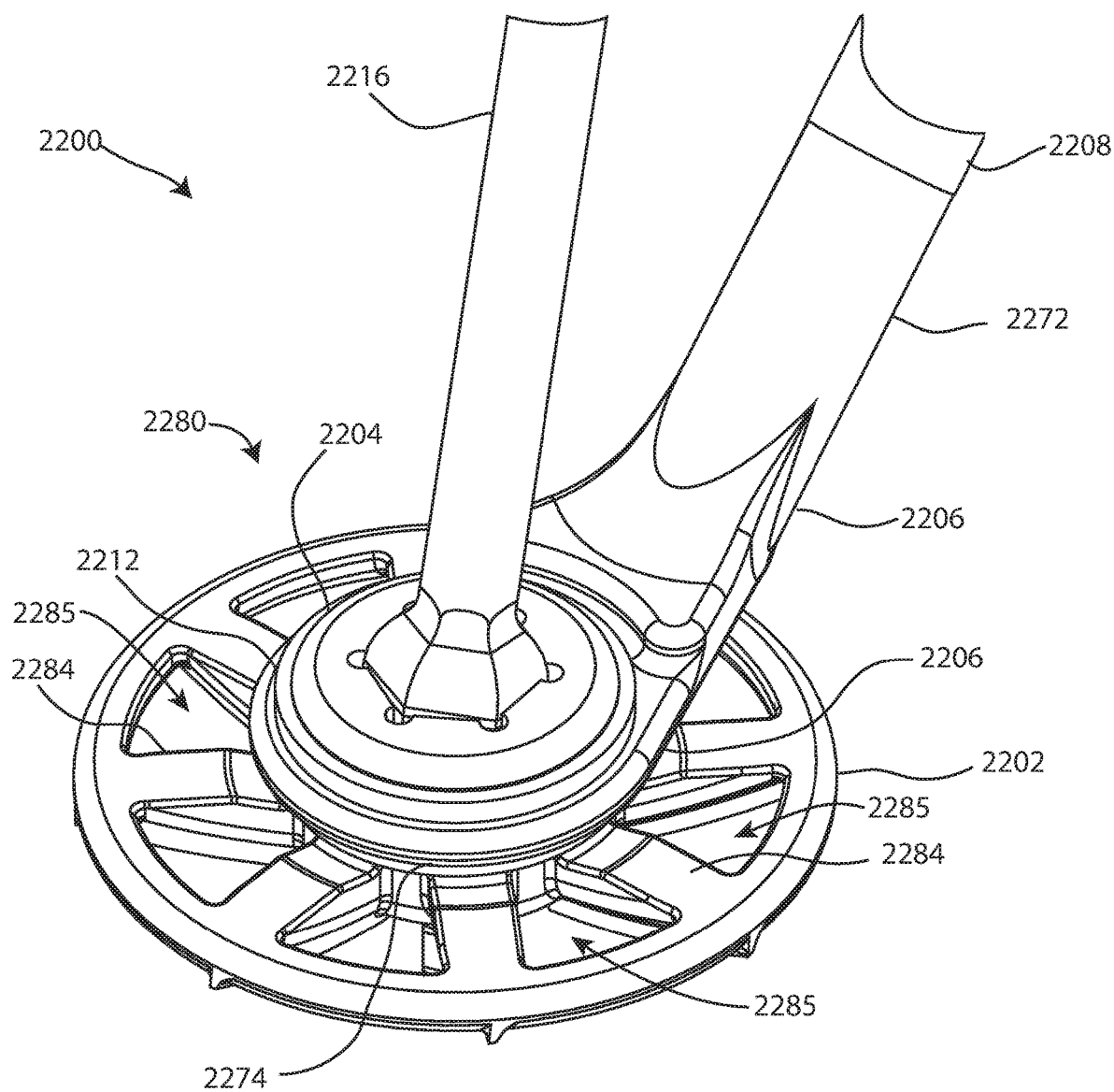
FIG. 12 is an isometric view of a portion of the offset reamer of FIG. 11.
Figure 13:
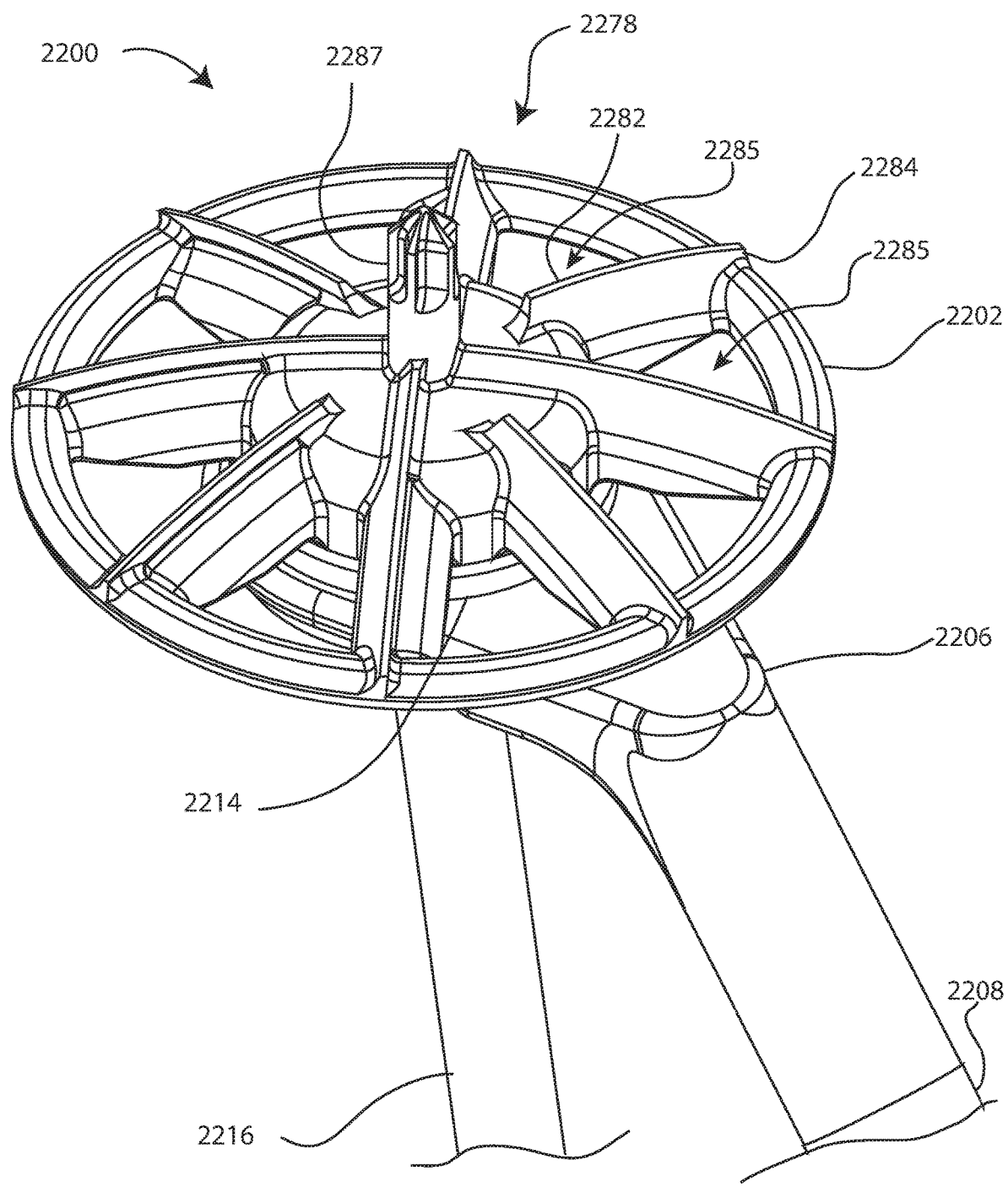
FIG. 13 is an isometric view of a portion of the offset reamer of FIG. 11 from a second viewpoint.
Figure 14:
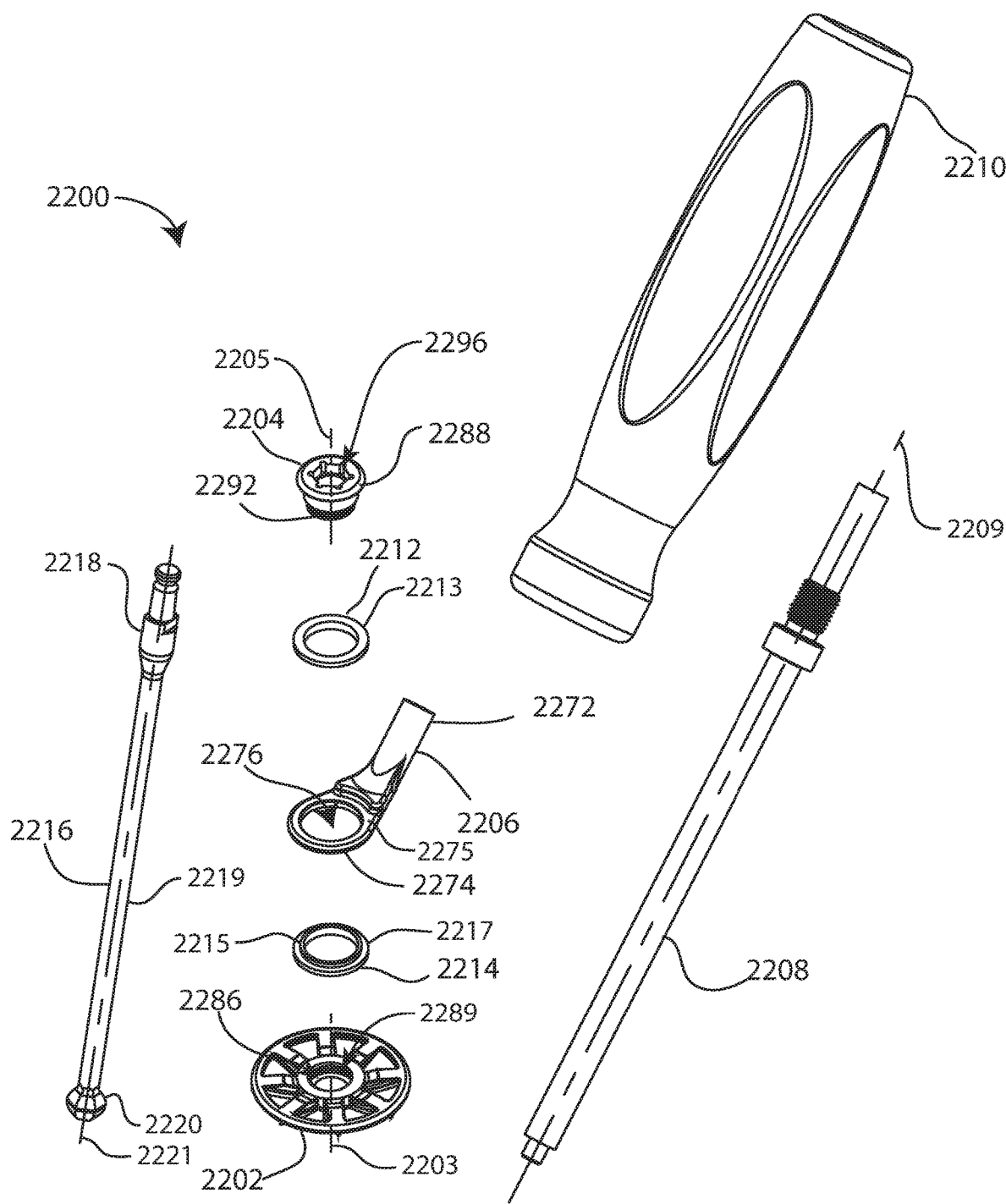
FIG. 14 is an isometric exploded view of the offset reamer of FIG. 11.
Figure 15:
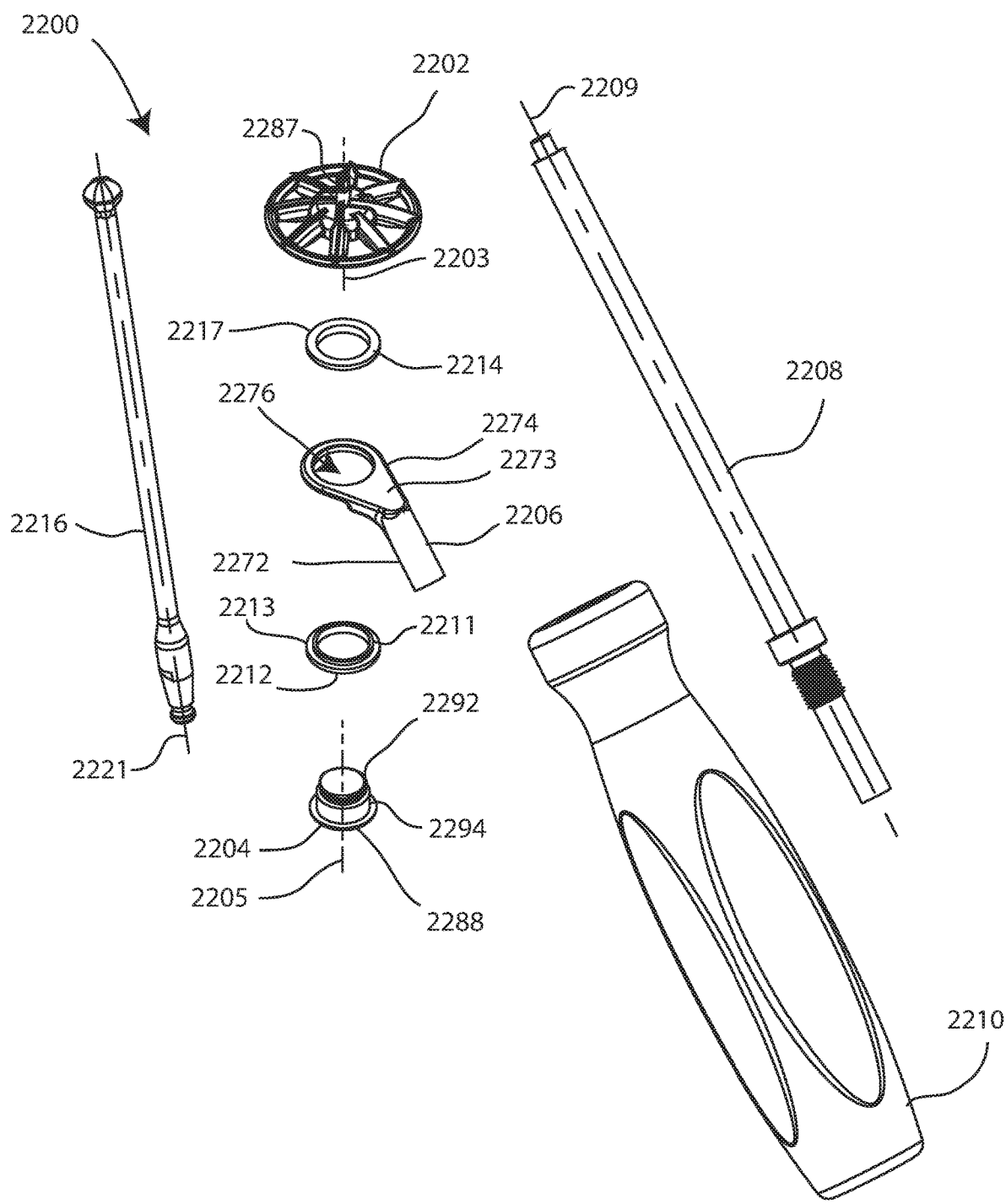
FIG. 15 is an isometric exploded view of the offset reamer of FIG. 11 from a second viewpoint.
Figure 16:
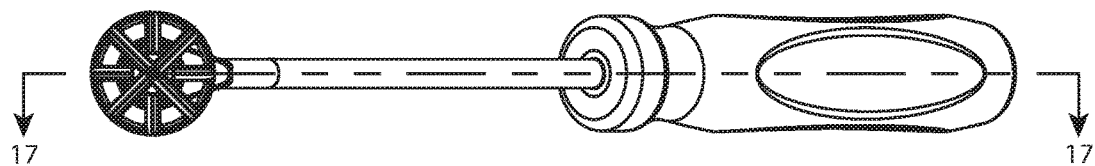
FIG. 16 is a bottom view of the offset reamer of FIG. 11.
Figure 17:
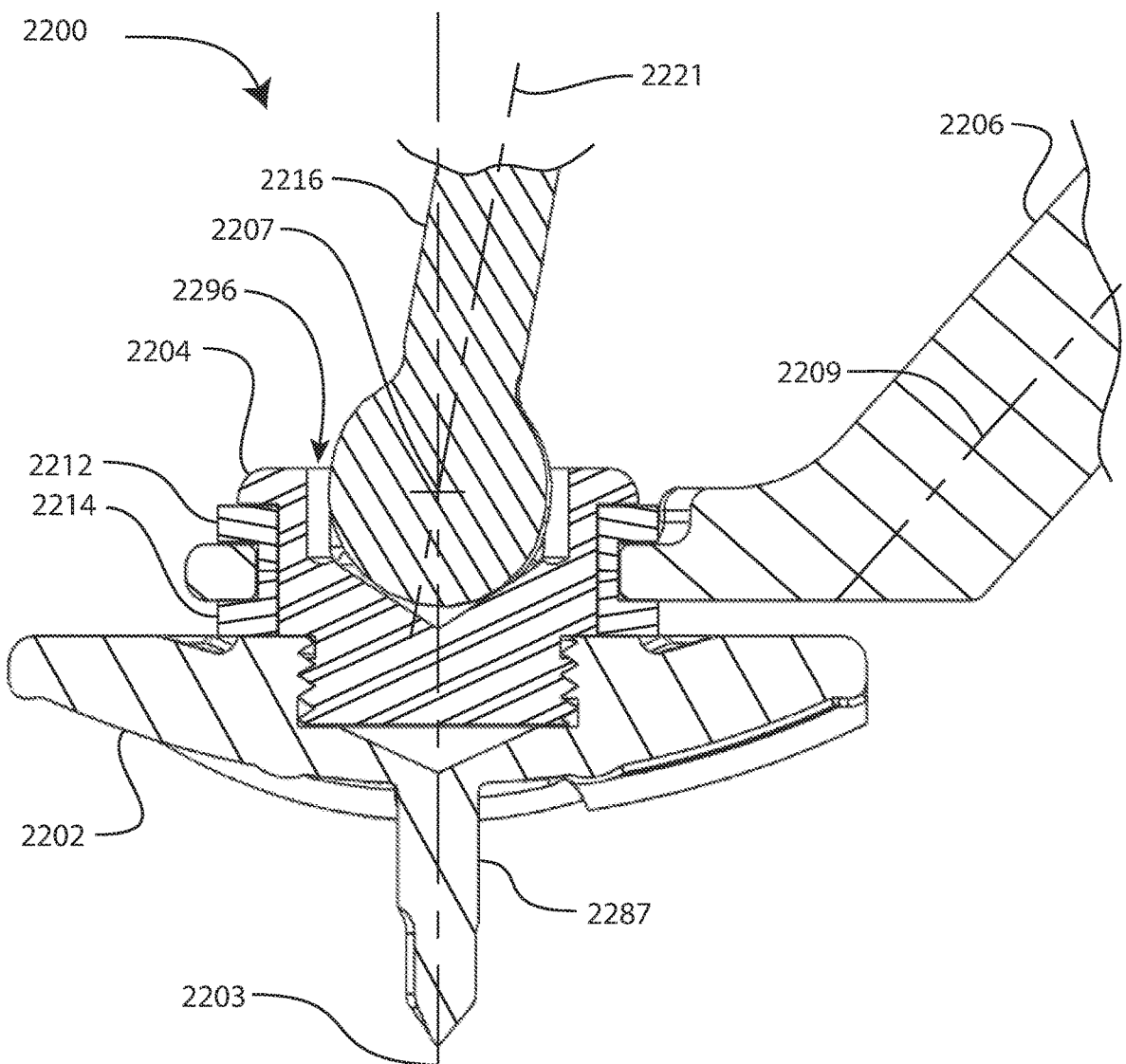
FIG. 17 is a cross sectional view through a portion of the offset reamer of FIG. 11, taken along line 17-17 of FIG. 16.

The reamer head 2202 is a round part with a central longitudinal rotational axis 2203, a convex obverse side 2278, or bone-facing side or cutting side (FIG. 13), and a reverse side 2280 (FIG. 12). The obverse side 2278 may be flat or concave in other examples devoted to other joints around the body. The obverse side 2278 includes bone removal features 2282, which may be teeth, serrations, ridges and grooves, knurling, a sandpaper texture, or the like. In the example shown, the bone removal features 2282 are sharpened edges on radial arms 2284 of the reamer head 2202. Eight arms 2284 are shown in the example, although any number of arms may be provided. The arms 2284 in the example are separated by windows 2285 or apertures. The reamer head 2202 includes a central socket 2286 in the reverse side 2280 (FIG. 14). The central socket 2286 may include a drive portion 2289 adjacent to the reverse side 2280, and may include a circular portion adjacent to the obverse side 2278. The drive portion 2289 may be a threaded socket, as illustrated in FIGS. 14 and 17, or another configuration for torque transmission in at least one rotational direction. The drive portion 2289 may be referred to as a torque input feature for torque transmission to the reamer head 2202. The reamer head 2202 is illustrated with a central shaft 2287 protruding from the obverse side 2278. In this example, the shaft 2287 is integral with the reamer head 2202. Alternately, the shaft may be separate from the reamer head 2202, and may be integral with the reamer coupler 2204, and may protrude through a circular portion of the central aperture 2286 in the manner described above for reamer head 2102 and reamer coupler 2104. The shaft 2287 may include cutting flutes at least along the leading tip, and may therefore be called a drill tip. FIGS. 13 and 15 illustrate this configuration. The reamer head 2202 may include a cannulation extending along the axis 2203 through the shaft 2287 or, in other examples, instead of the shaft 2287. The cannulation, if present, receives a k-wire, guide wire, bone pin, or the like so that the reaming surface can be fixed to a particular location, orientation, or trajectory in the glenoid or, in the case of a biconcave glenoid, so that the reaming surface can sequentially be fixed to multiple locations, orientations, or trajectories. The shaft 2287 may be spring loaded, and may be biased to be normally extended or normally retracted. In the latter situation, the shaft 2287 may only extend outwardly when a driver (discussed below) is engaged with the reamer coupler 2204.

Referring to FIGS. 14-15, the reamer coupler 2204 includes a central longitudinal rotational axis 2205, a head 2288, a drive feature 2292 under the head, and a shaft 2294 between the head 2288 and the drive feature 2292. The reamer coupler 2204 may be referred to as a coupling which connects the offset reamer 2200 to a prime mover or torque source such as a power driver or T-handle so that the reamer head 2202 may be rotated or spun about the axis 2203. The head 2288 may include a drive portion 2296, which may be a hex socket, as illustrated in FIG. 14, a hexalobular socket, or another configuration for torque transmission in at least one rotational direction. The drive portion 2296 may be referred to as a torque input feature for torque transmission to the reamer coupler 2204. The depth of the drive portion 2296, or its height if it is a positive feature, is a matter of design choice balancing the polyaxial range of motion with the stability of the corresponding driver. The drive feature 2292 may be a threaded shaft, as illustrated in FIG. 15, or another configuration for cooperation with the drive portion 2289 of the socket 2286 of the reamer head 2202 for torque transmission in at least one rotational direction. The drive feature 2292 may be referred to as a torque output feature for torque transmission to the reamer head 2202. The reamer coupler 2104 may include a cannulation extending along the axis 2205. The cannulation, if present, receives a k-wire, guide wire, bone pin, or the like.

The first bushing 2212 includes a tubular body, or tube 2211. A flange 2213 projects circumferentially outwardly around one end of the tube 2211.

The second bushing 2214 includes a tubular body, or tube 2215. A flange 2217 projects circumferentially outwardly around one end of the tube 2215.

The working tip 2206 may be coupled to one end of the shaft 2208 and the handle 2210 may be coupled to the other end of the shaft 2208 to form a handle assembly. The working tip 2206, the shaft 2208, and the handle 2210 may be permanently or temporarily coupled together. For example, the working tip 2206 and/or handle 2210 may be permanently welded to the shaft 2208. Alternatively, the working tip 2206 and/or handle 2210 may be temporarily threaded or snapped to the shaft 2208. The working tip 2206 includes a shaft portion 2272 for connection to the shaft 2208 and a plate portion 2274 that extends obliquely from the shaft portion. The shaft 2208 includes a central longitudinal axis 2209 with which the shaft portion 2272 aligns when the shaft 2208 and the shaft portion 2272 are connected. While the illustrated shaft 2208 is straight, in other examples the shaft may be curved or bent to be more functional or ergonomic according to the particular surgical site in which it will be used. The shaft portion 2272 and the shaft 2208 may include a cannulation extending along the axis 2209. The cannulation, if present, receives a k-wire, guide wire, bone pin, or the like so that the reaming surface can be fixed to a particular location, orientation, or trajectory in the glenoid or, in the case of a biconcave glenoid, so that the reaming surface can sequentially be fixed to multiple locations, orientations, or trajectories. The plate portion 2274 includes an obverse side 2273, or bone facing side, and a reverse side 2275 opposite the bone-facing side. The plate portion 2274 is pierced by an aperture 2276 or hole which may extend through the obverse side 2273 and the reverse side 2275.

Referring to FIG. 17, the reamer head 2202, the first bushing 2212, the working tip 2206, the second bushing 2214, and the reamer coupler 2204 are operatively assembled by inserting the tube 2211 of the first bushing 2212 into the aperture 2276 of the working tip 2206 so that the flange 2213 rests against the reverse side 2275; inserting the tube 2215 of the second bushing 2214 into the aperture 2276 of the working tip 2206 so that the flange 2217 rests against the obverse side 2273; inserting the reamer coupler 2204 into the tubes 2211, 2215 so that the head 2288 rests against the flange 2213 and the drive feature 2292 extends beyond the flange 2217; and coupling the drive feature 2292 to the drive portion 2289 of the central socket 2286 of the reamer head, for example by threading the drive feature 2292 into the drive portion 2289. The working tip 2206 may be said to carry the reamer coupler 2204 and the reamer head 2202, as well as the first bushing 2212 and the second bushing 2214. The reamer head 2202, the first bushing 2212, the working tip 2206, the second bushing 2214, and/or the reamer coupler 2204 may include a retention element, such as a ball detent, clip, retaining ring, groove, taper, twist, or the like, to keep the reamer head 2202, the first bushing 2212, the working tip 2206, the second bushing 2214, and/or the reamer coupler 2204 coupled together until intentionally disassembled. The operative assembly of the reamer head 2202, the first bushing 2212, the working tip 2206, the second bushing 2214, and the reamer coupler 2204 may be referred to as a working portion of the offset reamer 2200.

When the reamer head 2202, the first bushing 2212, the working tip 2206, the second bushing 2214, and the reamer coupler 2204 are operatively assembled, at least the reamer head 2202 and the reamer coupler 2204 may be rotationally coupled or fixed together with axes 2203, 2205 collinear. Together, the reamer head 2202 and the reamer coupler 2204 may rotate freely relative to the working tip 2206 about axis 2203; the bushings 2212, 2214 may also rotate freely relative to the reamer coupler 2204 and/or the working tip 2206, or they may be rotationally coupled or fixed to the reamer coupler 2204 or the working tip 2206. The handle assembly of the working tip 2206, the shaft 2208, and the handle 2210 may be manipulated by a user to control the location and orientation of the reamer axis 2203.

The reamer driver 2216, shown in FIGS. 11-17, may be used interchangeably with offset reamers 2100, 2200, 2300, 2400. The reamer driver 2216 includes a Hudson connector 2218 or torque bit, a shaft 2219, a drive tip 2220 opposite the torque bit, and a central longitudinal rotational axis 2221. The Hudson connector 2218 of the reamer driver 2216 may couple to a prime mover or torque source, such as a power driver or a T-handle. The drive tip 2220 may be directly engaged with the reamer coupler 2204, and rotated by the prime mover about the axis 2221 to turn the reamer coupler 2204 and the reamer head 2202 about axis 2203. In other words, the reamer driver 2216 may be rotationally coupled to the reamer coupler 2204 and the reamer head 2202. For example, the reamer driver 2216 may have a straight hex key drive tip to engage the hex socket drive portion 2296 so that axis 2221 is in line with, or coaxial with, the axis 2203. The reamer driver 2216 may alternatively have a ball drive tip 2220 as shown, which permits the rotational axis 2221 of the reamer driver 2216 to be polyaxially obliquely angled, or polyaxially angularly offset, relative to the rotational axis 2203 of the reamer head 2202. FIG. 17 illustrates an example in which the axis 2221 is obliquely angled, or angularly offset, relative to the axis 2203. In this example with the ball drive tip, the driver axis 2221 may be described as being angularly offset from, or noncollinear with, the rotational axis 2203 of the reamer head 2202, so that the driver axis 2221 and the axis 2203 have no more than a single mathematical point in common, and that only if the driver axis 2221 and the axis 2203 intersect. Therefore, the reamer driver 2216 may be referred to as an offset driver or an offset drive shaft due to the unconstrained angular offset between the axis 2221 and the axis 2203. The reamer driver 2216 may alternatively include other adaptations to permit the reamer driver 2216 to be obliquely angled, or angularly offset, relative to the rotational axis 2203 of the reamer head 2202, such as a universal joint, a flexible shaft portion, a bevel gear acting against the reamer head 2202 and/or the reamer coupler 2204, a ball Torx drive (hexalobular), a ball star drive, or the like. Various ball drive tips may be substituted for the ball hex drive tip 2220 shown, such as Torx, hexalobular, star, or various other polygonal or polylobular shapes. More specifically, the reamer driver 2216 may have a ball drive tip 2220 with five or more corners or points, which may provide a smooth feel with less turbulence or kicking during actuation. While the ball hex key drive tip is an example which provides polyaxial angular offset, other examples may provide a fixed angular offset. In use, the reamer driver 2216 may be angularly repositioned relative to the axis 2203 at any time the user desires, whether or not the driver is being actuated or rotated. The driver 2216 may be repositioned independently of any manipulation of the reamer head axis 2203 or the handle assembly, so that the angular offset between the axis 2203 and the driver axis 2221 is continuously variable.

With continued reference to FIG. 17, axis 2203 and axis 2221 may intersect at a point 2207. As explained above, in some instances axis 2203 and axis 2221 do intersect at a single mathematical point. In other examples, axis 2203 and axis 2221 may be skew, in which case point 2207 may be referred to as a virtual intersection point, or a point where axis 2203 and axis 2221 are closest together. In any case, axis 2221 may move relative to axis 2203 due to manipulation of the reamer driver 2216 while the point 2207 remains at a fixed distance or depth relative to the reamer head 2202 (particularly a fixed distance from the cutting side, measured along axis 2203) or the reamer coupler 2204 (particularly a fixed distance within the drive portion 2296, when the drive portion 2296 is a socket as shown).

Figure 18:
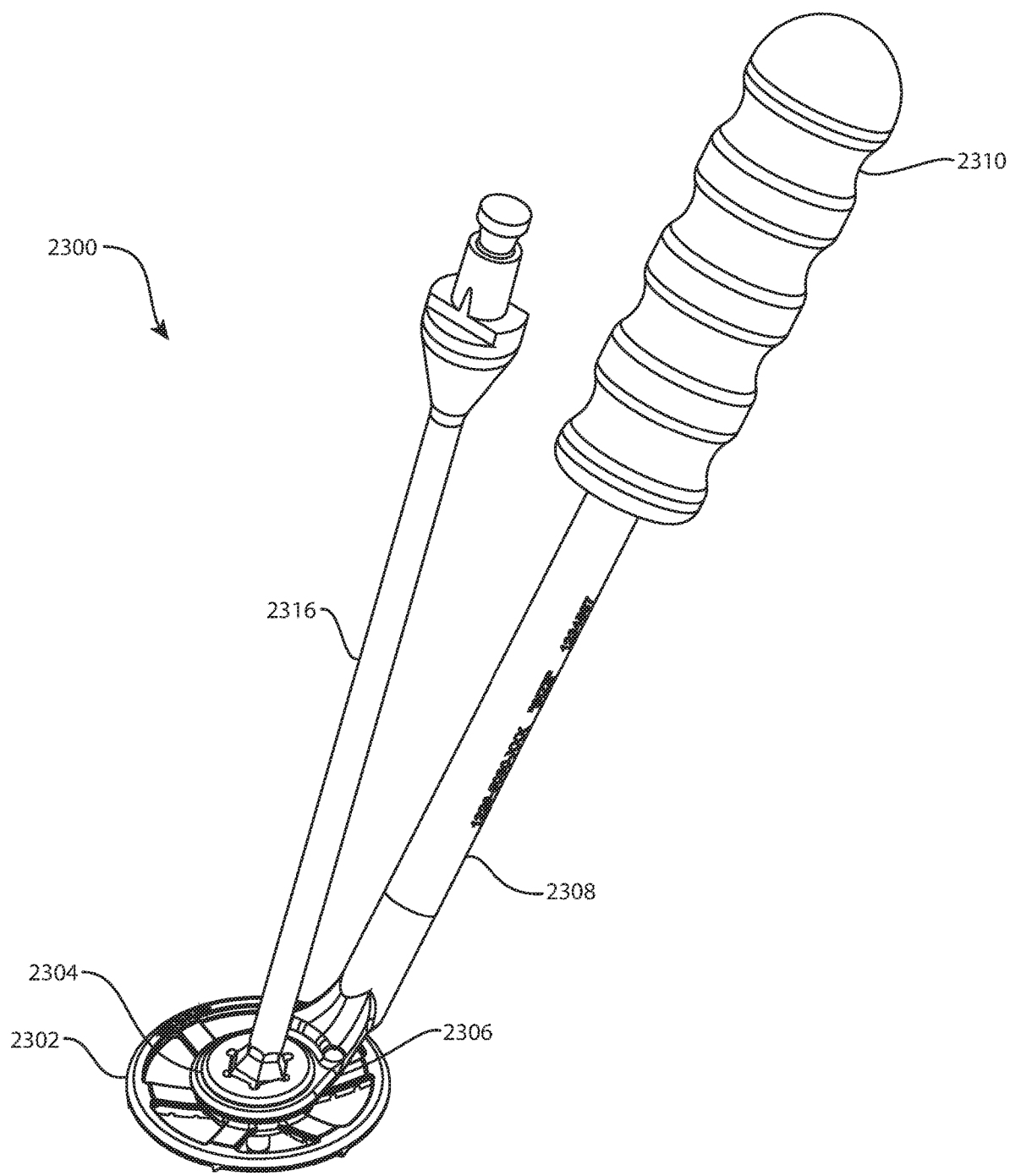
FIG. 18 is an isometric view of another offset reamer.

Referring to FIG. 18, another offset reamer 2300 includes a reamer head 2302, a reamer coupler 2304, a working tip 2306, a shaft 2308, and a handle 2310. FIGS. 18-24 show various views of offset reamer 2300. Offset reamer 2300 is shown with a reamer driver 2316, which may be used interchangeably with offset reamers 2100, 2200, 2300, 2400.

Figure 19:
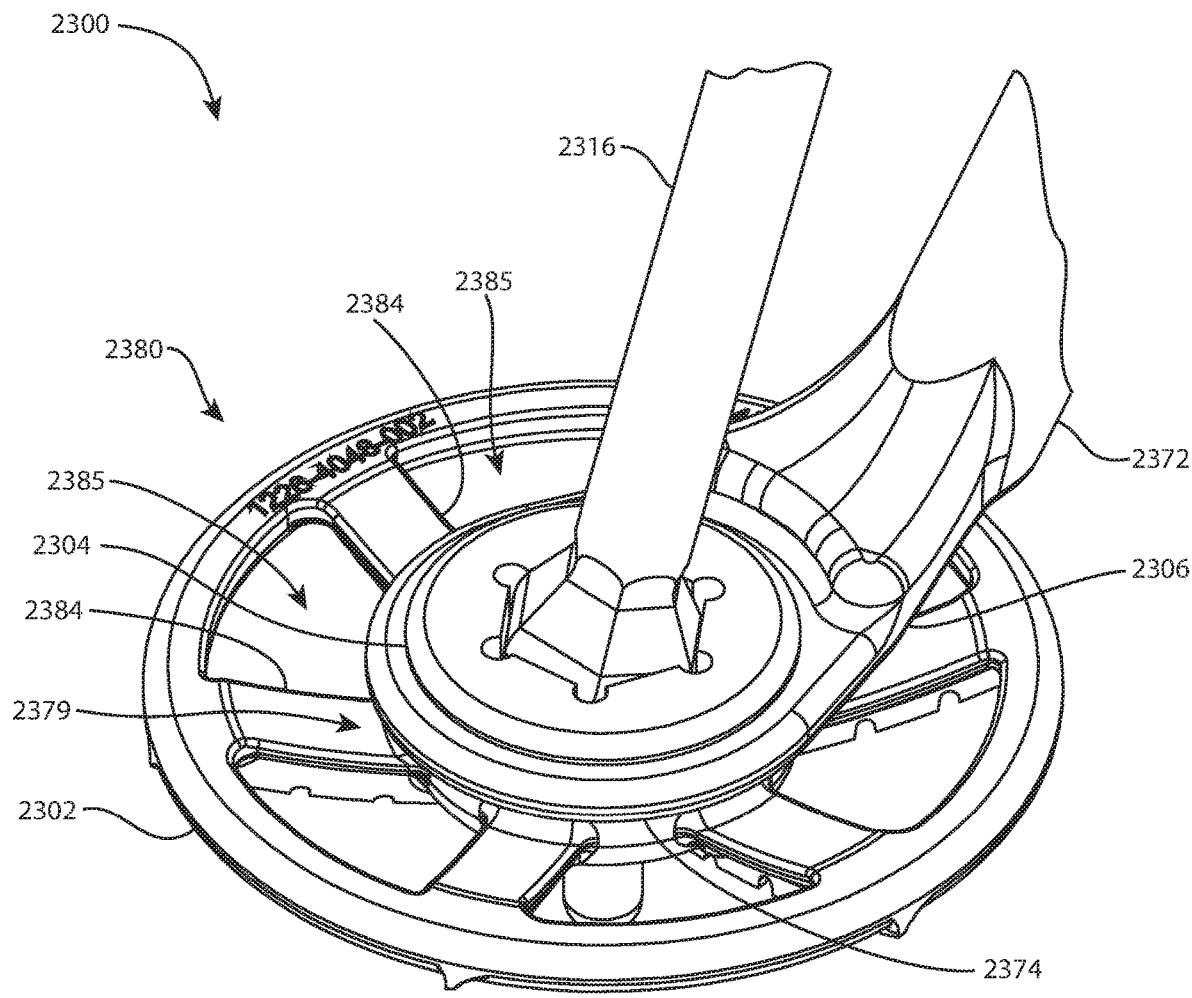
FIG. 19 is an isometric view of a portion of the offset reamer of FIG. 18.
Figure 20:
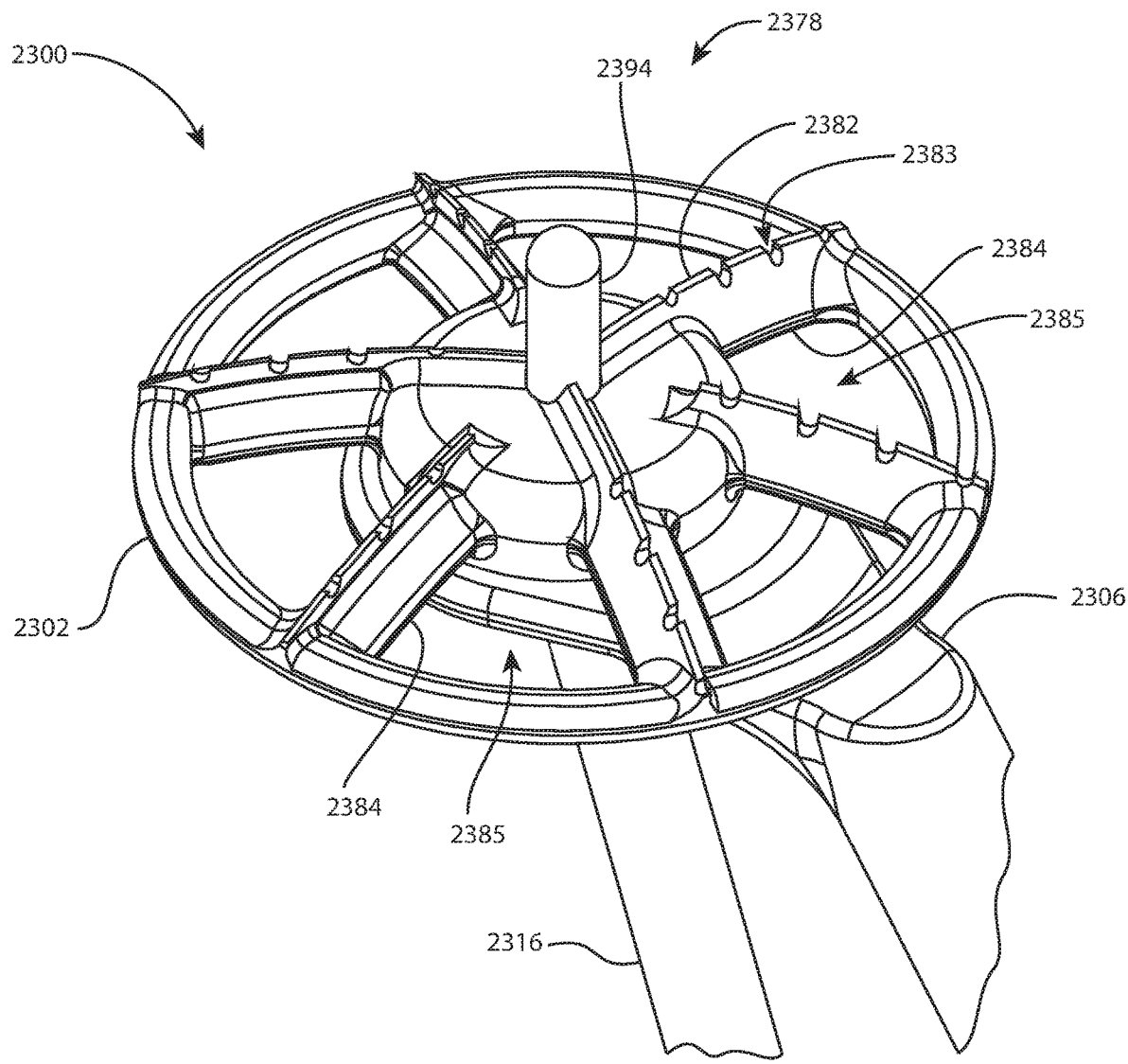
FIG. 20 is an isometric view of a portion of the offset reamer of FIG. 18 from a second viewpoint.
Figure 21:
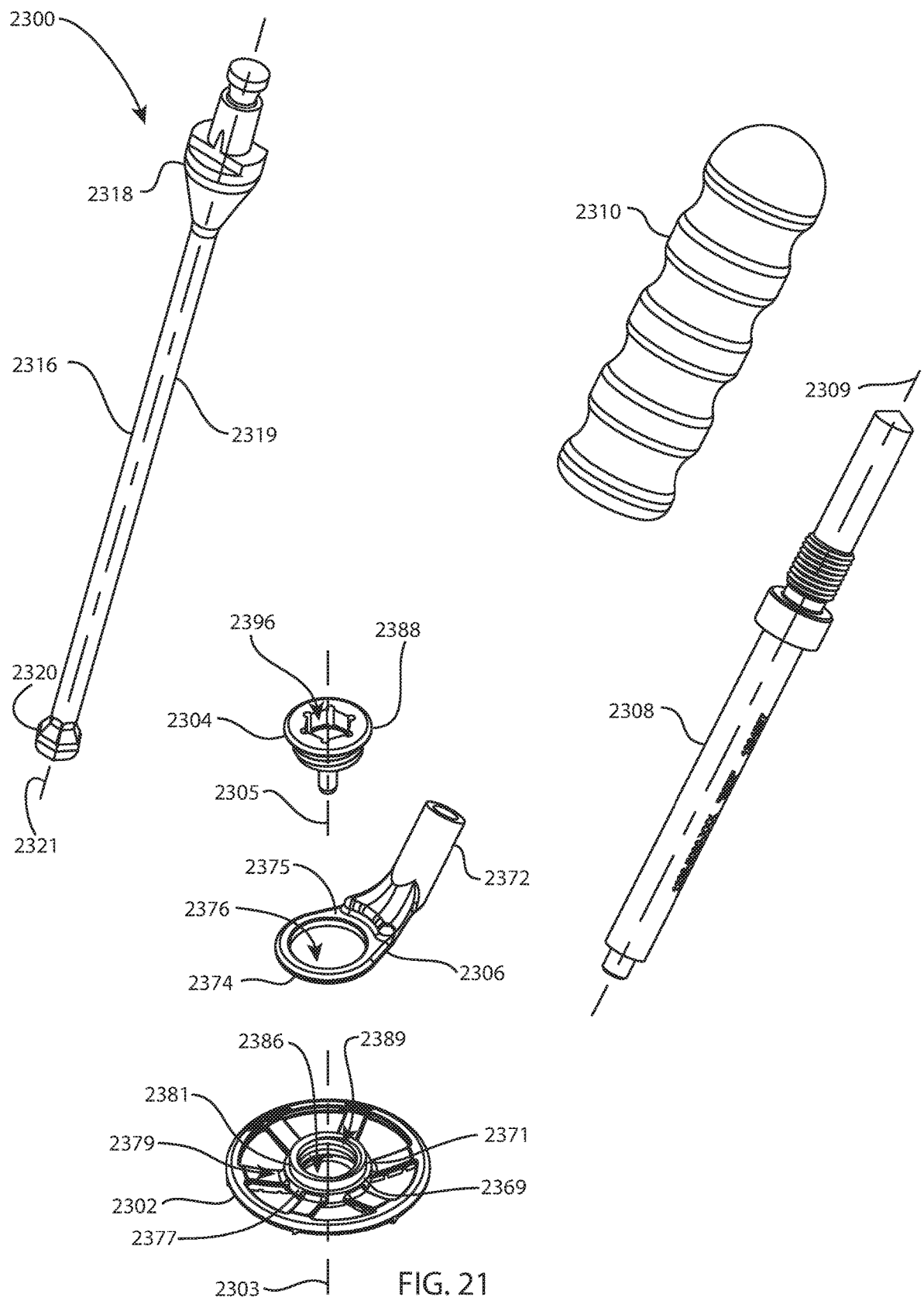
FIG. 21 is an isometric exploded view of the offset reamer of FIG. 18.
Figure 24:
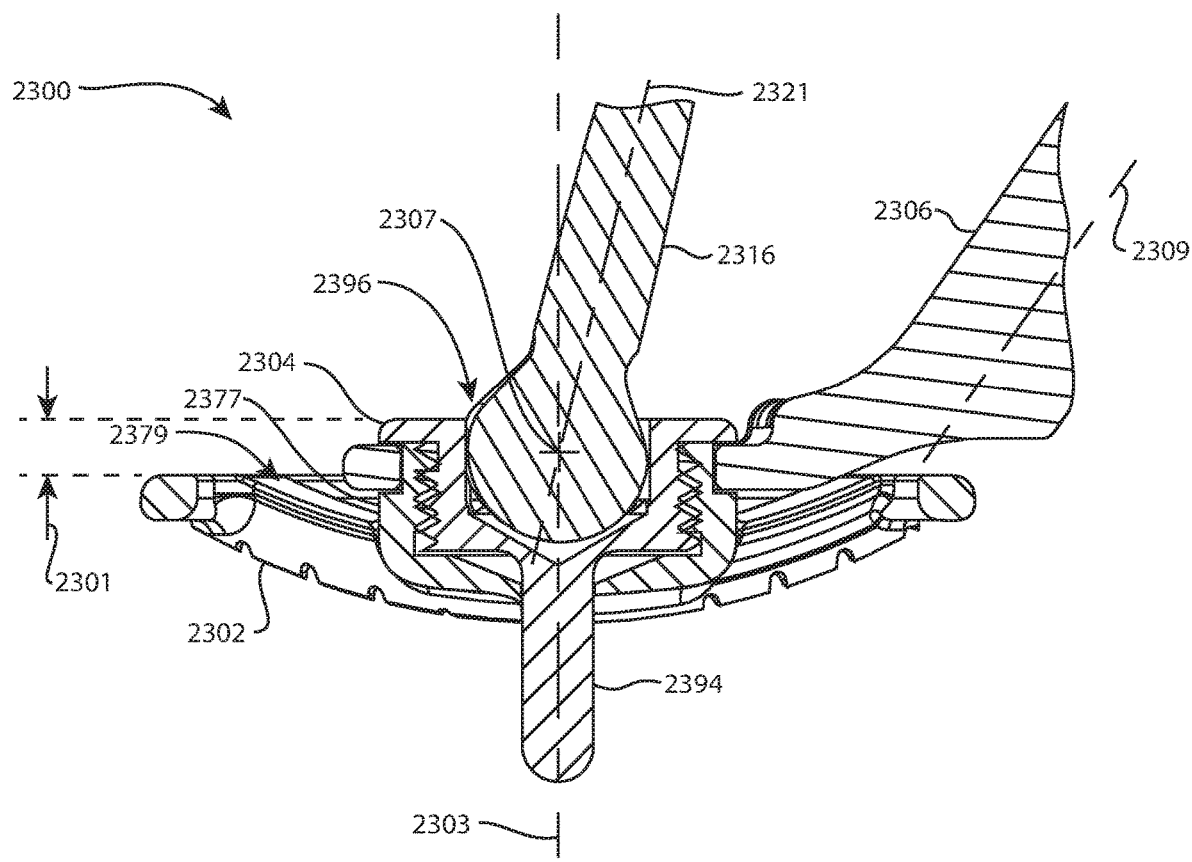
FIG. 24 is a cross sectional view through a portion of the offset reamer of FIG. 18, taken along line 24-24 of FIG. 23.

The reamer head 2302 is a round part with a central longitudinal rotational axis 2303, a convex obverse side 2378, or bone-facing side or cutting side (FIG. 20), and a reverse side 2380 (FIG. 19). The obverse side 2378 may be flat or concave in other examples devoted to other joints around the body. The obverse side 2378 includes bone removal features 2382, which may be teeth, serrations, ridges and grooves, knurling, a sandpaper texture, or the like. In the example shown, the bone removal features 2382 are sharpened edges on radial arms 2384 of the reamer head 2302. The bone removal features 2382 include several small notches 2383, also known as chip breakers, which improve cutting efficiency and reduce chatter, thereby improving the quality of the reamed surface 14 (FIG. 3). The chip breakers are arranged in a spiral pattern. Six arms 2384 are shown in the example, although any number of arms may be provided. The arms 2384 in the example are separated by windows 2385 or apertures. The reverse side 2380 of the reamer head 2302 includes a central shaft 2381 with an aperture 2386 (FIGS. 21-22), which may include a drive portion 2389 adjacent to the reverse side 2380 and a circular portion adjacent to the obverse side 2378. The drive portion 2389 may be a threaded socket, as illustrated in FIG. 21, or another configuration for torque transmission in at least one rotational direction. The drive portion 2389 may be referred to as a torque input feature for torque transmission to the reamer head 2302. Referring to FIGS. 19, 21, and 24, the shaft 2381 may be surrounded by an annular cavity 2379. Referring to FIGS. 21 and 24, the exterior of the shaft 2381 may include two portions, a first portion 2377 deep within the cavity 2379 closer to the obverse side 2378, and a second portion 2371 that extends from the first portion 2377 away from the obverse side, i.e., outwardly from the reverse side 2380. A shelf 2369 may be formed between the first and second portions 2377, 2371 due to a decrease in diameter from the first portion to the second portion.

Figure 22:
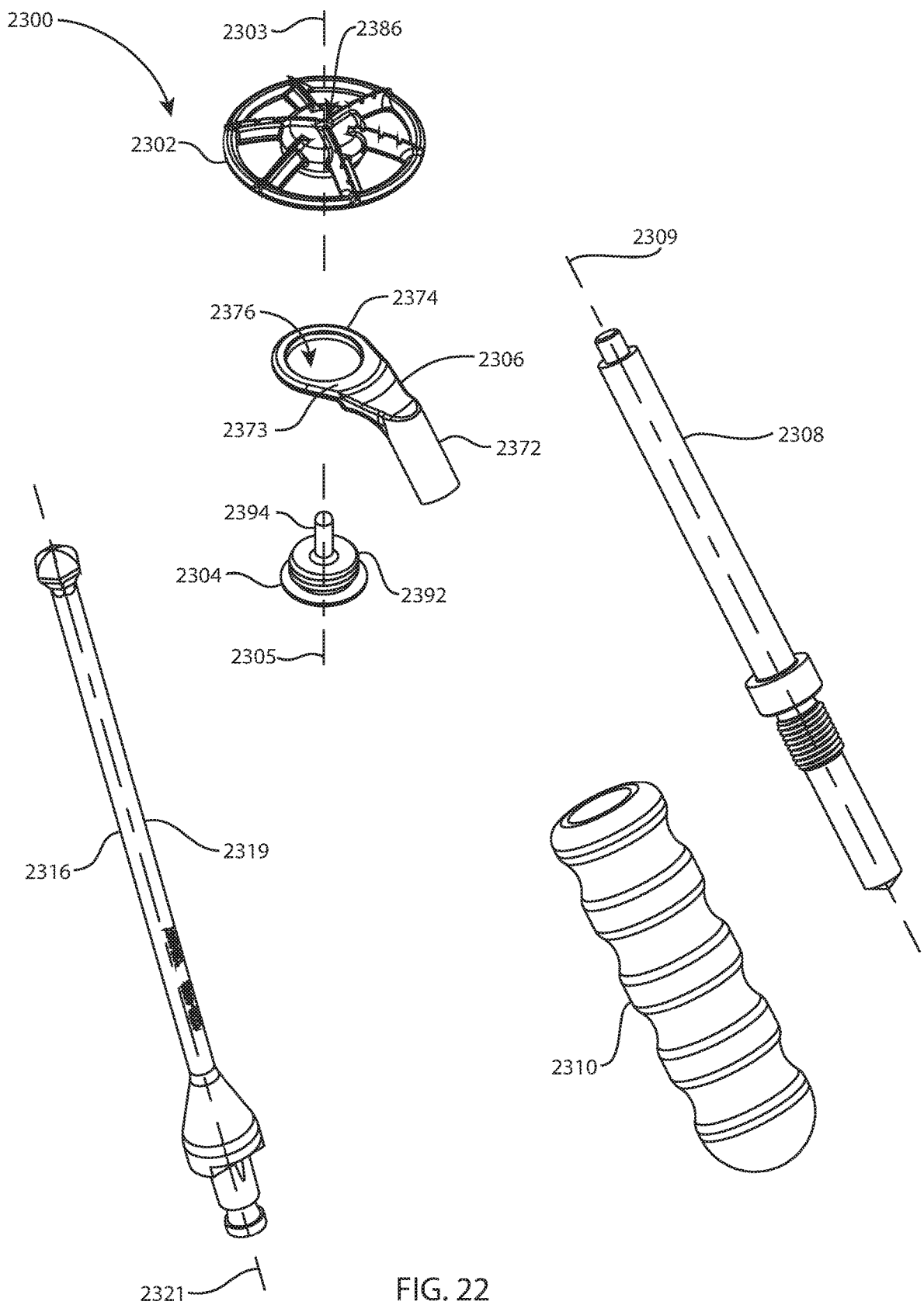
FIG. 22 is an isometric exploded view of the offset reamer of FIG. 18 from a second viewpoint.

Referring to FIGS. 21-22, the reamer coupler 2304 includes a central longitudinal rotational axis 2305, a head 2388, a drive feature 2392 under the head, and a shaft 2394 under the drive feature. The reamer coupler 2304 may be referred to as a coupling which connects the offset reamer 2300 to a prime mover or torque source such as a power driver or T-handle so that the reamer head 2302 may be rotated or spun about the axis 2303. The head 2388 may include a drive portion 2396, which may be a hex socket, as illustrated in FIG. 21, or another configuration for torque transmission in at least one rotational direction. The drive portion 2396 may be referred to as a torque input feature for torque transmission to the reamer coupler 2304. The depth of the drive portion 2396, or its height if it is a positive feature, is a matter of design choice balancing the polyaxial range of motion with the stability of the corresponding driver. The drive feature 2392 may be an externally threaded shaft, as illustrated in FIG. 22, or another configuration for cooperation with the drive portion 2389 of the aperture 2386 of the reamer head 2302 for torque transmission in at least one rotational direction. The drive feature 2392 may be referred to as a torque output feature for torque transmission to the reamer head 2302. The shaft 2394 may include cutting flutes at least along the leading tip, and may therefore be called a drill tip. However, FIGS. 22 and 24 illustrate an alternate configuration with a smooth shaft with a blunt tip. The reamer coupler 2304 may include a cannulation extending along the axis 2305 through the shaft 2394 or, in other examples, instead of the shaft 2394. The cannulation, if present, receives a k-wire, guide wire, bone pin, or the like so that the reaming surface can be fixed to a particular location, orientation, or trajectory in the glenoid or, in the case of a biconcave glenoid, so that the reaming surface can sequentially be fixed to multiple locations, orientations, or trajectories. The shaft 2394 may be spring loaded, and may be biased to be normally extended or normally retracted. In the latter situation, the shaft 2394 may only extend outwardly when a driver (discussed below) is engaged with the drive portion 2396.

The working tip 2306 may be coupled to one end of the shaft 2308 and the handle 2310 may be coupled to the other end of the shaft 2308 to form a handle assembly. The working tip 2306, the shaft 2308, and the handle 2310 may be permanently or temporarily coupled together. For example, the working tip 2306 and/or handle 2310 may be permanently welded to the shaft 2308. Alternatively, the working tip 2306 and/or handle 2310 may be temporarily threaded or snapped to the shaft 2308. The working tip 2306 includes a shaft portion 2372 for connection to the shaft 2308 and a plate portion 2374 that extends obliquely from the shaft portion. The shaft 2308 includes a central longitudinal axis 2309, with which the shaft portion 2372 aligns when the shaft 2308 and the shaft portion 2372 are connected. While the illustrated shaft 2308 is straight, in other examples the shaft may be curved or bent to be more functional or ergonomic according to the particular surgical site in which it will be used. The shaft portion 2372 and the shaft 2308 may include a cannulation extending along the axis 2309. The cannulation, if present, receives a k-wire, guide wire, bone pin, or the like so that the reaming surface can be fixed to a particular location, orientation, or trajectory in the glenoid or, in the case of a biconcave glenoid, so that the reaming surface can sequentially be fixed to multiple locations, orientations, or trajectories. The plate portion 2374 includes an obverse side 2373, or bone-facing side, and a reverse side 2375 opposite the bone-facing side. The plate portion is pierced by an aperture 2376 or hole which may extend through the obverse side 2373 and the reverse side 2375.

Referring to FIG. 24, the reamer head 2302, the reamer coupler 2304, and the working tip 2306 are operatively assembled by inserting the shaft 2381 through the aperture 2376 so that the reverse side 2380 faces the bone-facing side 2373 of the plate portion 2374, and inserting the shaft 2394 through the circular portion of the aperture 2386 of the reamer head 2302 so that the drive feature 2392 engages the drive portion 2389 of the aperture 2386 of the reamer head 2302; in the illustrated example, this involves threading the drive feature 2392 into the drive portion 2389. The working tip 2306 may be said to carry the reamer coupler 2304 and the reamer head 2302. The head 2388, the plate portion 2374, the shaft 2394, the drive feature 2392, and/or the aperture 2386 may include a retention element, such as a ball detent, clip, retaining ring, groove, taper, twist, or the like, to keep the head 2388, the plate portion 2374, the shaft 2394, the drive feature 2392, and/or the aperture 2386 coupled together until intentionally disassembled. The operative assembly of the reamer head 2302, the reamer coupler 2304, and the working tip 2306 may be referred to as a working portion of the offset reamer 2300.

When the reamer head 2302, the reamer coupler 2304, and the working tip 2306 are operatively assembled, at least the reamer head 2302 and the reamer coupler 2304 may be rotationally coupled or fixed together with axes 2303, 2305 collinear. Together, the reamer head 2302 and the reamer coupler 2304 may rotate freely relative to the working tip 2306 about axis 2303. The handle assembly of the working tip 2306, the shaft 2308, and the handle 2310 may be manipulated by a user to control the location and orientation of the reamer axis 2303.

Figure 23:
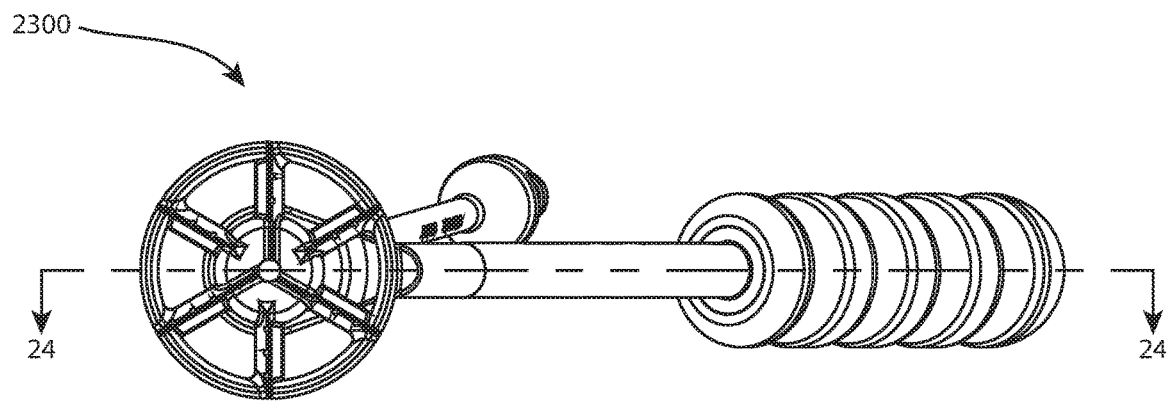
FIG. 23 is a bottom view of the offset reamer of FIG. 18.

The reamer driver 2316, shown in FIGS. 18-24, may be used interchangeably with offset reamers 2100, 2200, 2300, 2400. The reamer driver 2316 includes a Hudson connector 2318 or torque bit, a shaft 2319, a drive tip 2320 opposite the torque bit, and a central longitudinal rotational axis 2321. The Hudson connector 2318 of the reamer driver 2316 may couple to a prime mover or torque source, such as a power driver or a T-handle. The drive tip 2320 may be directly engaged with the reamer coupler 2304, and rotated by the prime mover about the axis 2321 to turn the reamer coupler 2304 and the reamer head 2302 about axis 2303. In other words, the reamer driver 2316 may be rotationally coupled to the reamer coupler 2304 and the reamer head 2302. For example, the reamer driver 2316 may have a straight hex key drive tip to engage the hex socket drive portion 2396 so that axis 2321 is in line with, or coaxial with, the axis 2303. The reamer driver 2316 may alternatively have a ball drive tip 2320 as shown, which permits the rotational axis 2321 of the reamer driver 2316 to be polyaxially obliquely angled, or polyaxially angularly offset, relative to the rotational axis 2303 of the reamer head 2302. FIGS. 23 and 24 illustrate an example in which the axis 2321 is obliquely angled, or angularly offset, relative to the axis 2303 in two planes. In this example with the ball drive tip, the driver axis 2321 may be described as being angularly offset from, or noncollinear with, the rotational axis 2303 of the reamer head 2302, so that the driver axis 2321 and the axis 2303 have no more than a single mathematical point in common, and that only if the driver axis 2321 and the axis 2303 intersect. Therefore, the reamer driver 2316 may be referred to as an offset driver or an offset drive shaft due to the unconstrained angular offset between the axis 2321 and the axis 2303. The reamer driver 2316 may alternatively include other adaptations to permit the reamer driver 2316 to be obliquely angled, or angularly offset, relative to the rotational axis 2303 of the reamer head 2302, such as a universal joint, a flexible shaft portion, a bevel gear acting against the reamer head 2302 and/or the reamer coupler 2304, a ball Torx drive (hexalobular), a ball star drive, or the like. Various ball drive tips may be substituted for the ball hex drive tip 2320 shown, such as Torx, hexalobular, star, or various other polygonal or polylobular shapes. More specifically, the reamer driver 2316 may have a ball drive tip 2320 with five or more corners or points, which may provide a smooth feel with less turbulence or kicking during actuation. While the ball hex key drive tip is an example which provides polyaxial angular offset, other examples may provide a fixed angular offset. In use, the reamer driver 2316 may be angularly repositioned relative to the axis 2303 at any time the user desires, whether or not the driver is being actuated or rotated. The driver 2316 may be repositioned independently of any manipulation of the reamer head axis 2303 or the handle assembly, so that the angular offset between the axis 2303 and the driver axis 2321 is continuously variable.

With continued reference to FIG. 24, axis 2303 and axis 2321 may intersect at a point 2307. As explained above, in some instances axis 2303 and axis 2321 do intersect at a single mathematical point. In other examples, axis 2303 and axis 2321 may be skew, in which case point 2307 may be referred to as a virtual intersection point, or a point where axis 2303 and axis 2321 are closest together. In any case, axis 2321 may move relative to axis 2303 due to manipulation of the reamer driver 2316 while the point 2307 remains at a fixed distance or depth relative to the reamer head 2302 (particularly a fixed distance from the cutting side, measured along axis 2303) or the reamer coupler 2304 (particularly a fixed distance within the drive portion 2396, when the drive portion 2396 is a socket as shown).

Figure 25:
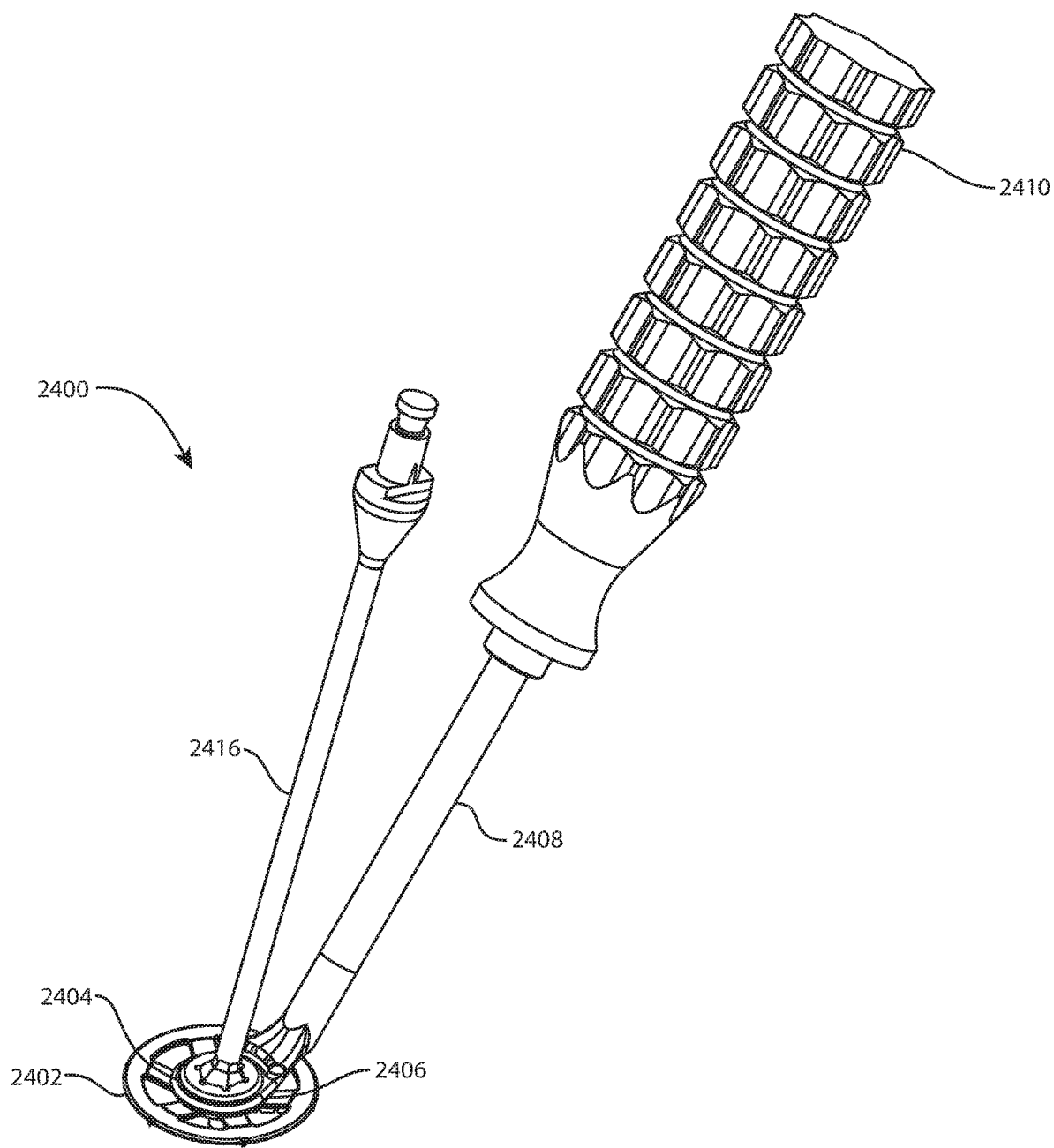
FIG. 25 is an isometric view of another offset reamer.

Referring to FIG. 25, another offset reamer 2400 includes a reamer head 2402, a reamer coupler 2404, a working tip 2406, a shaft 2408, and a handle 2410. FIGS. 25-31 show various views of offset reamer 2400. Offset reamer 2400 is shown with a reamer driver 2416, which may be used interchangeably with offset reamers 2100, 2200, 2300, 2400.

Figure 26:
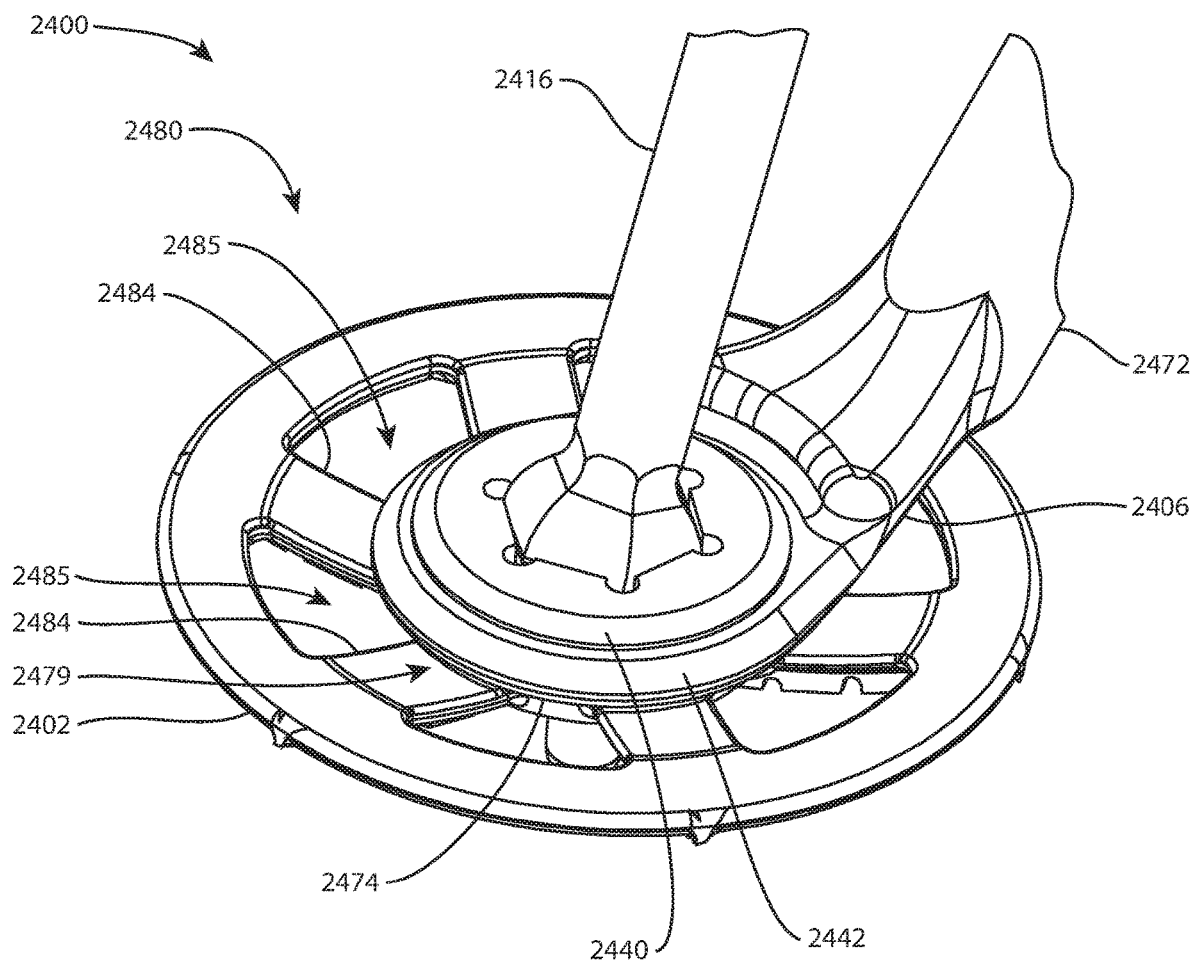
FIG. 26 is an isometric view of a portion of the offset reamer of FIG. 25.
Figure 27:
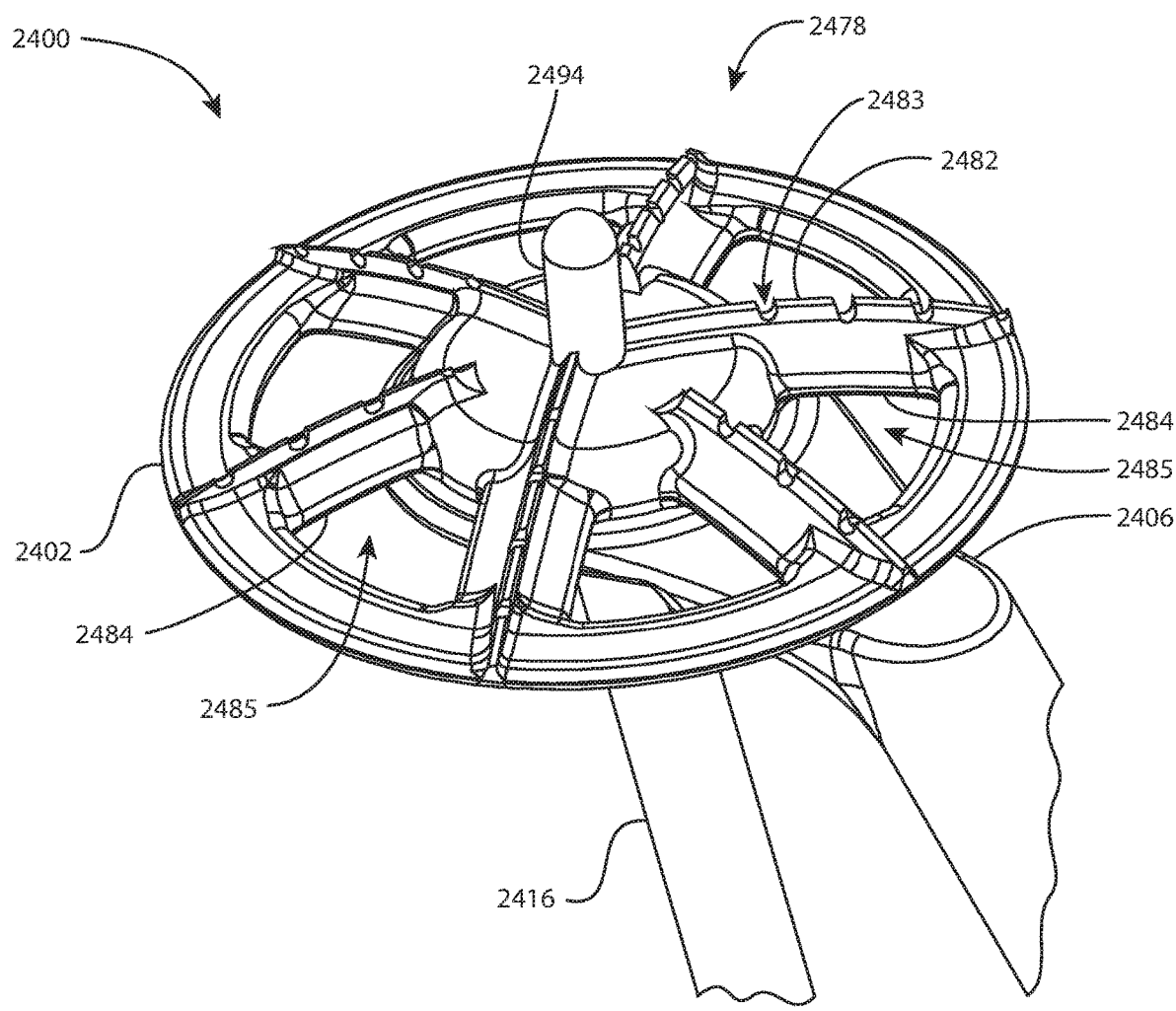
FIG. 27 is an isometric view of a portion of the offset reamer of FIG. 25 from a second viewpoint.
Figure 28:
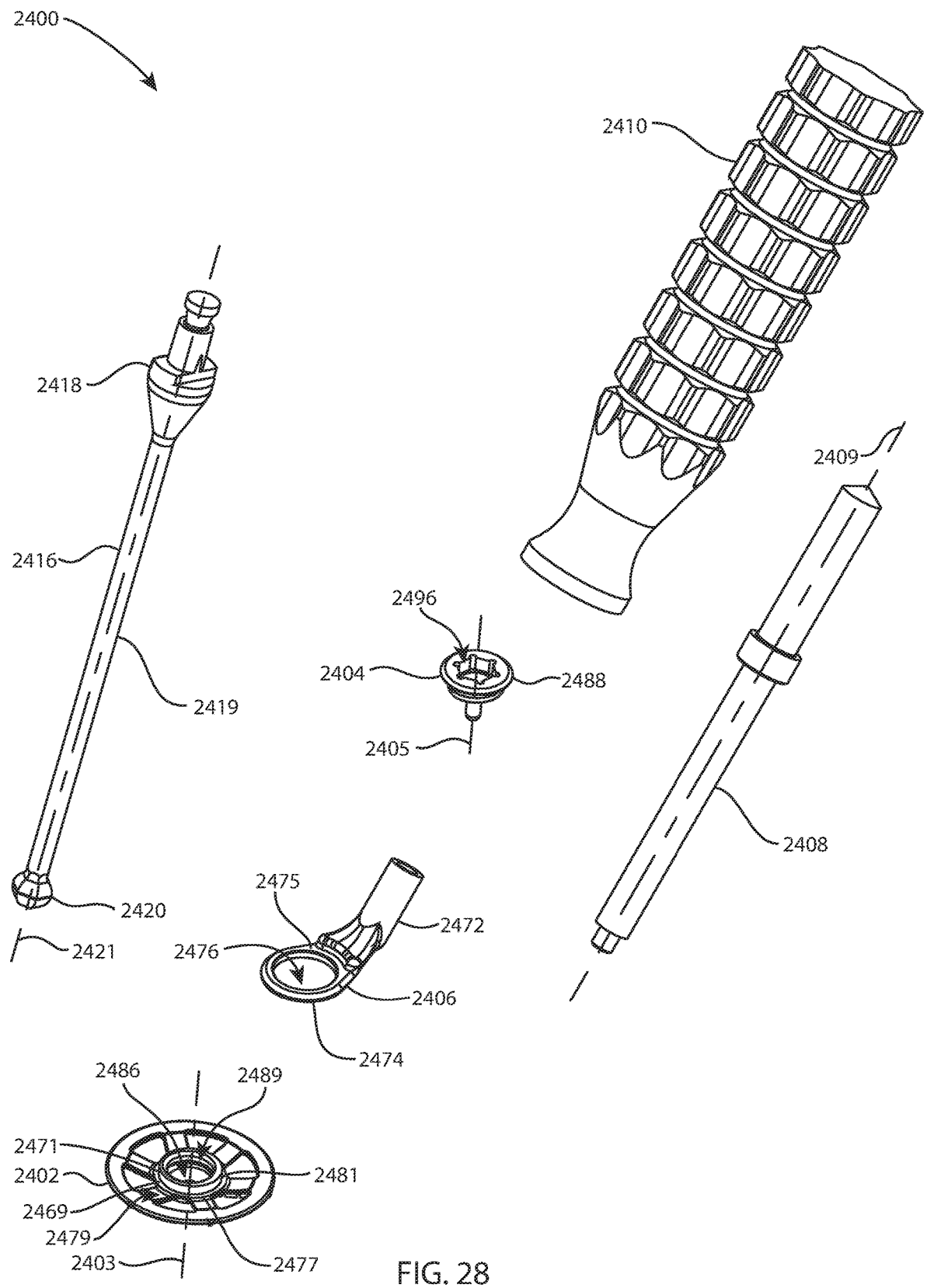
FIG. 28 is an isometric exploded view of the offset reamer of FIG. 25.
Figure 31:
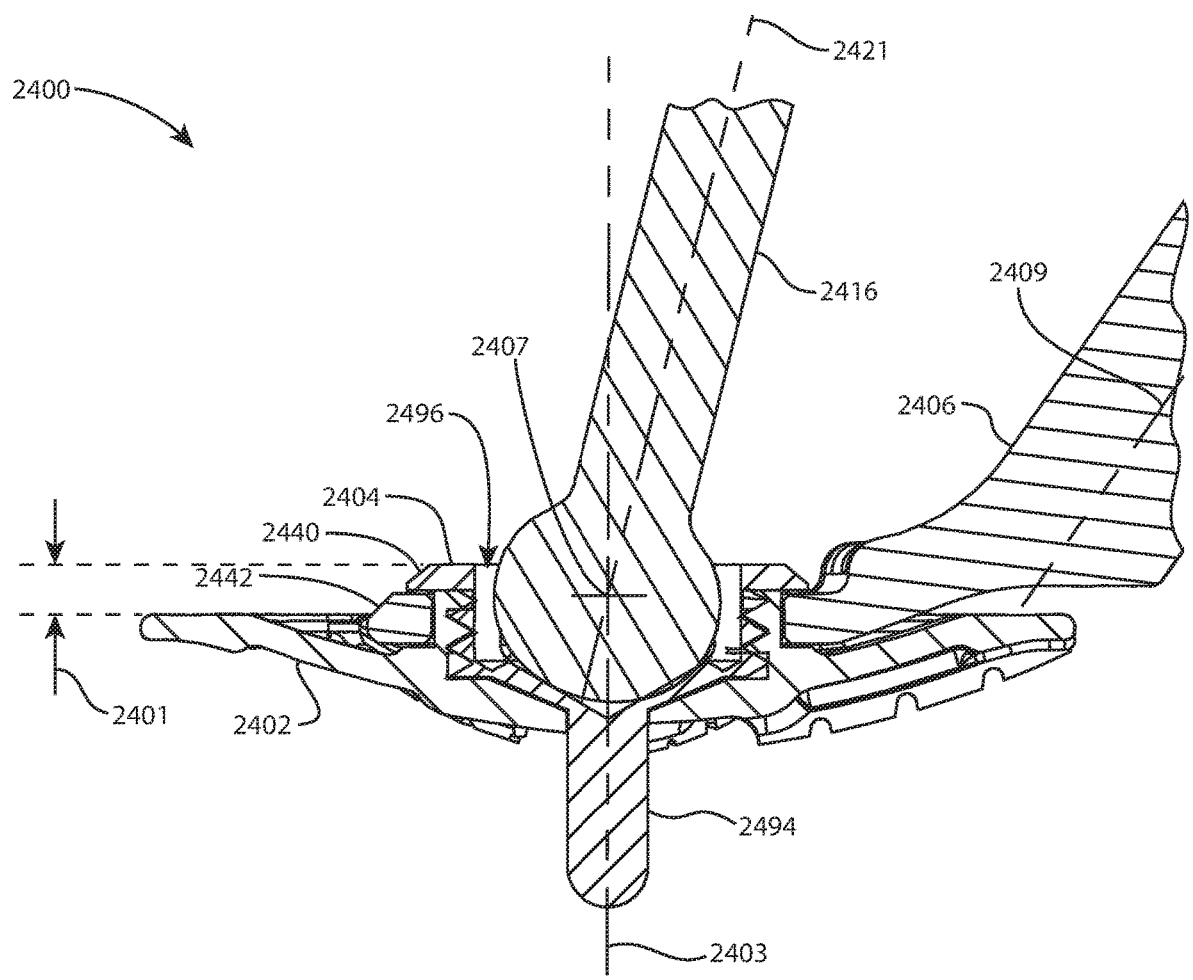
FIG. 31 is a cross sectional view through a portion of the offset reamer of FIG. 25, taken along line 31-31 of FIG. 30.

The reamer head 2402 is a round part with a central longitudinal rotational axis 2403, a convex obverse side 2478, or bone-facing side or cutting side (FIG. 27), and a reverse side 2480 (FIG. 26). The obverse side 2478 may be flat or concave in other examples devoted to other joints around the body. The obverse side 2478 includes bone removal features 2482, which may be teeth, serrations, ridges and grooves, knurling, a sandpaper texture, or the like. In the example shown, the bone removal features 2482 are sharpened edges on radial arms 2484 of the reamer head 2402. The bone removal features 2482 include several small notches 2483, also known as chip breakers, which improve cutting efficiency. Six arms 2484 are shown in the example, although any number of arms may be provided. The arms 2484 in the example are separated by windows 2485 or apertures. The reverse side 2480 of the reamer head 2402 includes a central shaft 2481 with an aperture 2486 (FIGS. 28-29), which may include a drive portion 2489 adjacent to the reverse side 2480 and a circular portion adjacent to the obverse side 2478. The drive portion 2489 may be a threaded socket, as illustrated in FIG. 28, or another configuration for torque transmission in at least one rotational direction. The drive portion 2489 may be referred to as a torque input feature for torque transmission to the reamer head 2402. Referring to FIGS. 26, 28, and 31, the shaft 2481 may be surrounded by an annular cavity 2479. Referring to FIGS. 28 and 31, the exterior of the shaft 2481 may include two portions, a first portion 2477 deep within the cavity 2479 closer to the obverse side 2478, and a second portion 2471 that extends from the first portion 2477 away from the obverse side, i.e., outwardly from the reverse side 2480. A shelf 2469 may be formed between the first and second portions 2477, 2471 due to a decrease in diameter from the first portion to the second portion.

Figure 29:
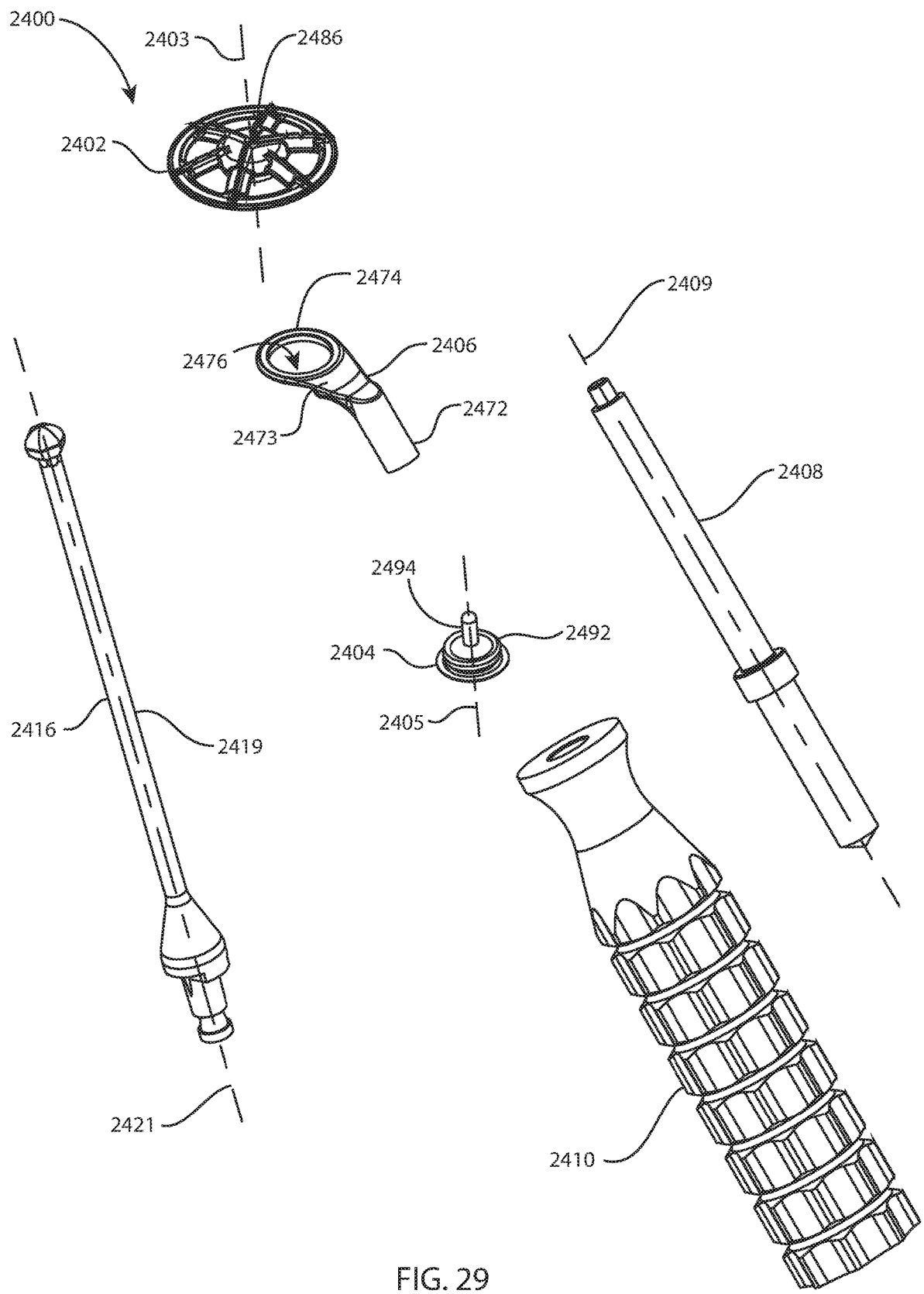
FIG. 29 is an isometric exploded view of the offset reamer of FIG. 25 from a second viewpoint.
Figure 30:
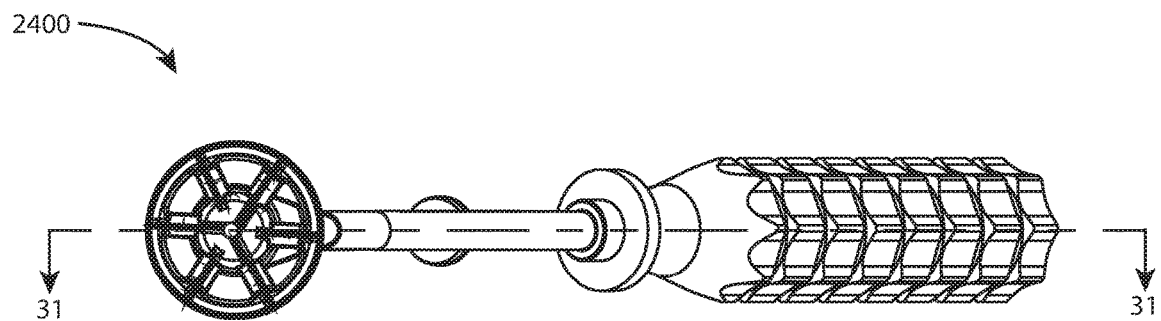
FIG. 30 is a bottom view of the offset reamer of FIG. 25.

Referring to FIGS. 28-29, the reamer coupler 2404 includes a central longitudinal rotational axis 2405, a head 2488, a drive feature 2492 under the head, and a shaft 2494 under the drive feature. The reamer coupler 2404 may be referred to as a coupling which connects the offset reamer 2400 to a prime mover or torque source such as a power driver or T-handle so that the reamer head 2402 may be rotated or spun about the axis 2403. The head 2488 in this example includes a chamfer 2440 around the top edge. The head 2488 may include a drive portion 2496, which may be a hex socket, as illustrated in FIG. 28, or another configuration for torque transmission in at least one rotational direction. The drive portion 2496 may be referred to as a torque input feature for torque transmission to the reamer coupler 2404. The depth of the drive portion 2496, or its height if it is a positive feature, is a matter of design choice balancing the polyaxial range of motion with the stability of the corresponding driver. The drive feature 2492 may be an externally threaded shaft, as illustrated in FIG. 29, or another configuration for cooperation with the drive portion 2489 of the aperture 2486 of the reamer head 2402 for torque transmission in at least one rotational direction. The drive feature 2492 may be referred to as a torque output feature for torque transmission to the reamer head 2402. The shaft 2494 may include cutting flutes at least along the leading tip, and may therefore be called a drill tip. However, FIGS. 29 and 31 illustrate an alternate configuration with a smooth shaft with a blunt tip. The reamer coupler 2404 may include a cannulation extending along the axis 2405 through the shaft 2494 or, in other examples, instead of the shaft 2494. The cannulation, if present, receives a k-wire, guide wire, bone pin, or the like so that the reaming surface can be fixed to a particular location, orientation, or trajectory in the glenoid or, in the case of a biconcave glenoid, so that the reaming surface can sequentially be fixed to multiple locations, orientations, or trajectories. The shaft 2494 may be spring loaded, and may be biased to be normally extended or normally retracted. In the latter situation, the shaft 2494 may only extend outwardly when a driver (discussed below) is engaged with the drive portion 2496.

The working tip 2406 may be coupled to one end of the shaft 2408 and the handle 2410 may be coupled to the other end of the shaft 2408 to form a handle assembly. The working tip 2406, the shaft 2408, and the handle 2410 may be permanently or temporarily coupled together. For example, the working tip 2406 and/or handle 2410 may be permanently welded to the shaft 2408. Alternatively, the working tip 2406 and/or handle 2410 may be temporarily threaded or snapped to the shaft 2408. The working tip 2406 includes a shaft portion 2472 for connection to the shaft 2408 and a plate portion 2474 that extends obliquely from the shaft portion. The shaft 2408 includes a central longitudinal axis 2409, with which the shaft portion 2472 aligns when the shaft 2408 and the shaft portion 2472 are connected. While the illustrated shaft 2408 is straight, in other examples the shaft may be curved or bent to be more functional or ergonomic according to the particular surgical site in which it will be used. The shaft portion 2472 and the shaft 2408 may include a cannulation extending along the axis 2409. The cannulation, if present, receives a k-wire, guide wire, bone pin, or the like so that the reaming surface can be fixed to a particular location, orientation, or trajectory in the glenoid or, in the case of a biconcave glenoid, so that the reaming surface can sequentially be fixed to multiple locations, orientations, or trajectories. The plate portion 2474 includes an obverse side 2473, or bone-facing side, and a reverse side 2475 opposite the bone-facing side. The plate portion in this example includes a chamfer around the outer edge of the obverse side 2473. The plate portion is pierced by an aperture 2476 or hole which may extend through the obverse side 2473 and the reverse side 2475.

Referring to FIG. 31, the reamer head 2402, the reamer coupler 2404, and the working tip 2406 are operatively assembled by inserting the shaft 2481 through the aperture 2476 so that the reverse side 2480 faces the bone-facing side 2473 of the plate portion 2474, and inserting the shaft 2494 through the circular portion of the aperture 2486 of the reamer head 2402 so that the drive feature 2492 engages the drive portion 2489 of the aperture 2486 of the reamer head 2402; in the illustrated example, this involves threading the drive feature 2492 into the drive portion 2489. The working tip 2406 may be said to carry the reamer coupler 2404 and the reamer head 2402. The head 2488, the plate portion 2474, the shaft 2494, the drive feature 2492, and/or the aperture 2486 may include a retention element, such as a ball detent, clip, retaining ring, groove, taper, twist, or the like, to keep the head 2488, the plate portion 2474, the shaft 2494, the drive feature 2492, and/or the aperture 2486 coupled together until intentionally disassembled. The operative assembly of the reamer head 2402, the reamer coupler 2404, and the working tip 2406 may be referred to as a working portion of the offset reamer 2400.

When the reamer head 2402, the reamer coupler 2404, and the working tip 2406 are operatively assembled, at least the reamer head 2402 and the reamer coupler 2404 may be rotationally coupled or fixed together with axes 2403, 2405 collinear. Together, the reamer head 2402 and the reamer coupler 2404 may rotate freely relative to the working tip 2406 about axis 2403. The handle assembly of the working tip 2406, the shaft 2408, and the handle 2410 may be manipulated by a user to control the location and orientation of the reamer axis 2403.

The reamer driver 2416, shown in FIGS. 25-31, may be used interchangeably with offset reamers 2100, 2200, 2300, 2400. The reamer driver 2416 includes a Hudson connector 2418 or torque bit, a shaft 2419, a drive tip 2420 opposite the torque bit, and a central longitudinal rotational axis 2421. The Hudson connector 2418 of the reamer driver 2416 may couple to a prime mover or torque source, such as a power driver or a T-handle. The drive tip 2420 may be directly engaged with the reamer coupler 2404, and rotated by the prime mover about the axis 2421 to turn the reamer coupler 2404 and the reamer head 2402 about axis 2403. In other words, the reamer driver 2416 may be rotationally coupled to the reamer coupler 2404 and the reamer head 2402. For example, the reamer driver 2416 may have a straight hex key drive tip to engage the hex socket drive portion 2496 so that axis 2421 is in line with, or coaxial with, the axis 2403. The reamer driver 2416 may alternatively have a ball drive tip 2420 as shown, which permits the rotational axis 2421 of the reamer driver 2416 to be polyaxially obliquely angled, or polyaxially angularly offset, relative to the rotational axis 2403 of the reamer head 2402. FIG. 31 illustrates an example in which the axis 2421 is obliquely angled, or angularly offset, relative to the axis 2403. In this example with the ball drive tip, the driver axis 2421 may be described as being angularly offset from, or noncollinear with, the rotational axis 2403 of the reamer head 2402, so that the driver axis 2421 and the axis 2403 have no more than a single mathematical point in common, and that only if the driver axis 2421 and the axis 2403 intersect. Therefore, the reamer driver 2416 may be referred to as an offset driver or an offset drive shaft due to the unconstrained angular offset between the axis 2421 and the axis 2403. The reamer driver 2416 may alternatively include other adaptations to permit the reamer driver 2416 to be obliquely angled, or angularly offset, relative to the rotational axis 2403 of the reamer head 2402, such as a universal joint, a flexible shaft portion, a bevel gear acting against the reamer head 2402 and/or the reamer coupler 2404, a ball Torx drive (hexalobular), a ball star drive, or the like. Various ball drive tips may be substituted for the ball hex drive tip 2420 shown, such as Torx, hexalobular, star, or various other polygonal or polylobular shapes. More specifically, the reamer driver 2416 may have a ball drive tip 2420 with five or more corners or points, which may provide a smooth feel with less turbulence or kicking during actuation. While the ball hex key drive tip is an example which provides polyaxial angular offset, other examples may provide a fixed angular offset. In use, the reamer driver 2416 may be angularly repositioned relative to the axis 2403 at any time the user desires, whether or not the driver is being actuated or rotated. The driver 2416 may be repositioned independently of any manipulation of the reamer head axis 2403 or the handle assembly, so that the angular offset between the axis 2403 and the driver axis 2421 is continuously variable.

With continued reference to FIG. 31, axis 2403 and axis 2421 may intersect at a point 2407. As explained above, in some instances axis 2403 and axis 2421 do intersect at a single mathematical point. In other examples, axis 2403 and axis 2421 may be skew, in which case point 2407 may be referred to as a virtual intersection point, or a point where axis 2403 and axis 2421 are closest together. In any case, axis 2421 may move relative to axis 2403 due to manipulation of the reamer driver 2416 while the point 2407 remains at a fixed distance or depth relative to the reamer head 2402 (particularly a fixed distance from the cutting side, measured along axis 2403) or the reamer coupler 2404 (particularly a fixed distance within the drive portion 2496, when the drive portion 2496 is a socket as shown).

Figure 32A:
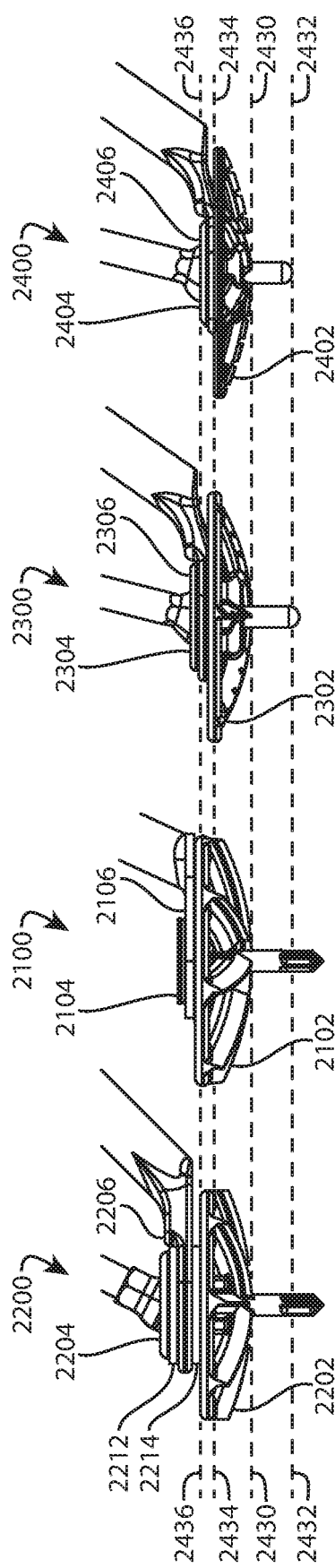
FIG. 32A is a front view of a portion of the offset reamer of FIG. 11, a portion of the offset reamer of FIG. 4, a portion of the offset reamer of FIG. 18, and a portion of the offset reamer of FIG. 25, all at the same scale.
Figure 32B:
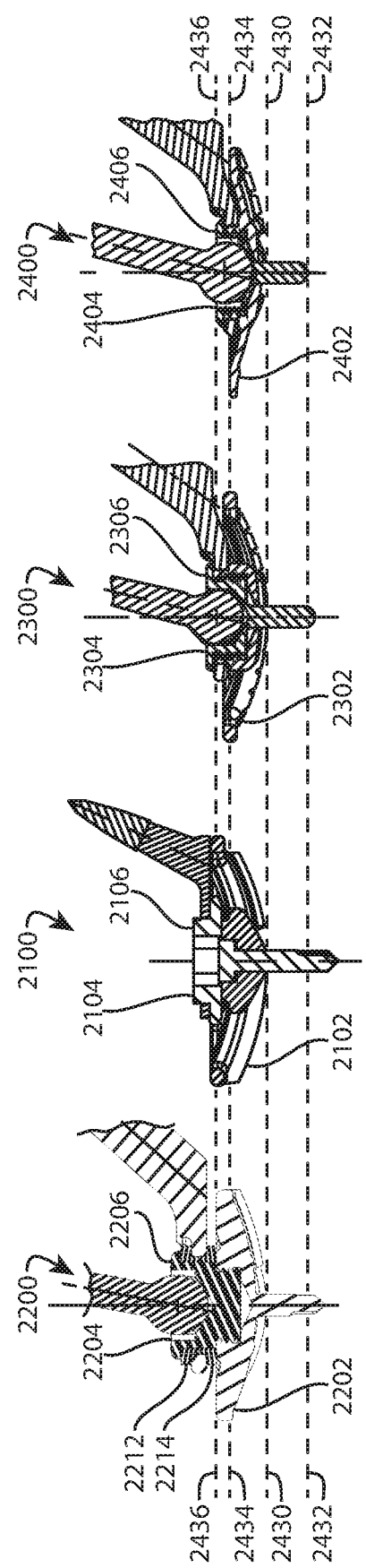
FIG. 32B is the cross-sectional view of FIG. 17, the cross-sectional view of FIG. 10, the cross-sectional view of FIG. 24, and the cross-sectional view of FIG. 31, all at the same scale as FIG. 32A.

Referring to FIGS. 32A-32B, the working portions of reamers 2100, 2200, 2300, 2400 are shown together, all at the same scale, and aligned so that the obverse side of the reamer head is tangent to line 2430. In this arrangement, the progressive reduction in overall height of the working portions can be seen, from the tallest working portion of reamer 2200 on the left to the shortest working portion of reamer 2400 on the right. Overall height is taken from the top of the reamer coupler to the central tangency at the bottom of the obverse side of the reamer head, if the shaft 2194, 2287, 2394, 2494 is retractable, or to the bottom of the shaft, if the shaft is not retractable. Line 2432 is tangent to the bottom of the shaft 2494. The shaft 2287 is 1.94 times as tall as the shaft 2494 is from line 2430. Line 2434 lies along the top of the reverse side 2480 of the reamer head 2402. The reamer head 2202 is 1.49 times as tall as the reamer head 2402 is from line 2430. Line 2436 lies along the top of the reamer coupler 2404. The reamer coupler 2204 protrudes 1.96 times higher than the reamer coupler 2404 does from line 2430. Thus the overall height of the working portion of reamer 2200, from the top of the reamer coupler to the central tangency at the bottom of the obverse side of the reamer head, is 1.96 times the overall height of the working portion of reamer 2400, and the overall height of the working portion of reamer 2200, from the top of the reamer coupler to the bottom of the shaft, is 1.95 times the overall height of the working portion of reamer 2400.

The reduction in overall height of the working portions is shown as a progression from the tallest working portion of reamer 2200 on the left to the shortest working portion of reamer 2400 on the right. Referring to FIGS. 10, 17, and 32, the reduction in overall height of the working portion from reamer 2200 to reamer 2100 was achieved by eliminating the first and second bushings 2212, 2214, with corresponding reduction in the overall height of the reamer coupler 2104; reducing the thickness of the head 2188 and the plate portion 2174; and reducing the height of the shaft 2187 from line 2430 (FIG. 32A-B). Referring to FIGS. 10, 24, and 32, the reduction in overall height of the working portion from reamer 2100 to reamer 2300 was achieved by partially recessing the plate portion 2374 below the top surface of the reverse side 2380 of the reamer head 2302, partially recessing the interconnection between the drive feature 2392 and the drive portion 2389 within the aperture 2376, reducing the overall height of the reamer head 2302, and reducing the overall height of the shaft 2387. Note that the plate portions 2174, 2274 of reamers 2100, 2200 are entirely outside the reamer heads 2102, 2202. The interconnection between the drive feature 2392 and the drive portion 2389 is surrounded and supported by the plate portion 2374 to maintain strength despite reducing the wall thickness of the drive feature 2392 and the drive portion 2389. The overall height of the arms 2384 was decreased and their width increased to maintain strength. Referring to FIGS. 24, 31, and 32, the reduction in overall height of the working portion from reamer 2300 to reamer 2400 was achieved by further recessing the plate portion 2474 below the top surface of the reverse side 2480 of the reamer head 2402, reducing the overall height of the interconnection between the drive feature 2492 and the drive portion 2489, reducing the depth of the drive portion 2496, further reducing the overall height of the reamer head 2402, and further reducing the overall height of the shaft 2487. The overall height of the arms 2384 was again decreased and their width again increased to maintain strength.

Figure 33:
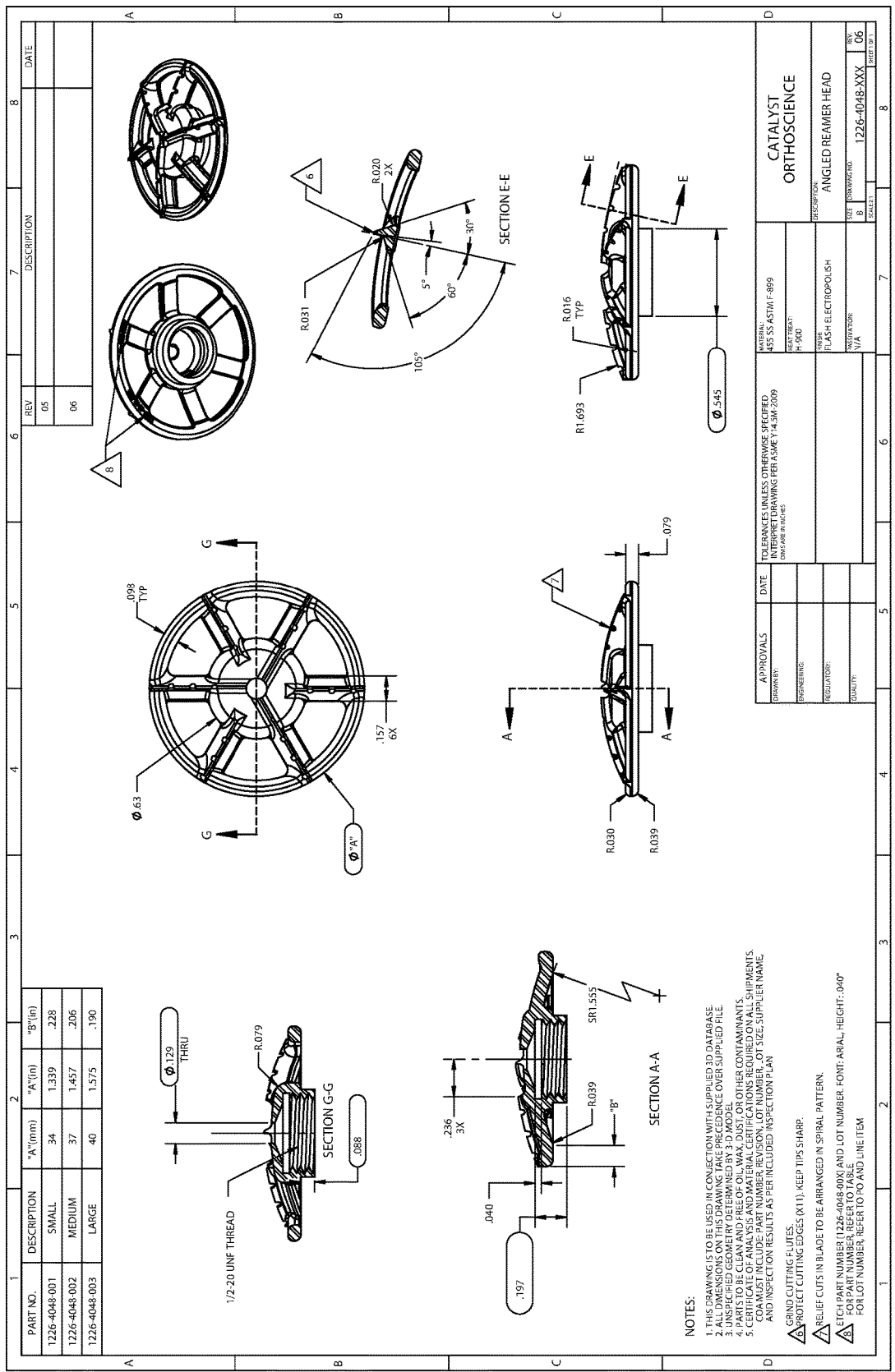
FIG. 33 is an engineering drawing of a reamer head of the offset reamer of FIG. 18.
Figure 34:
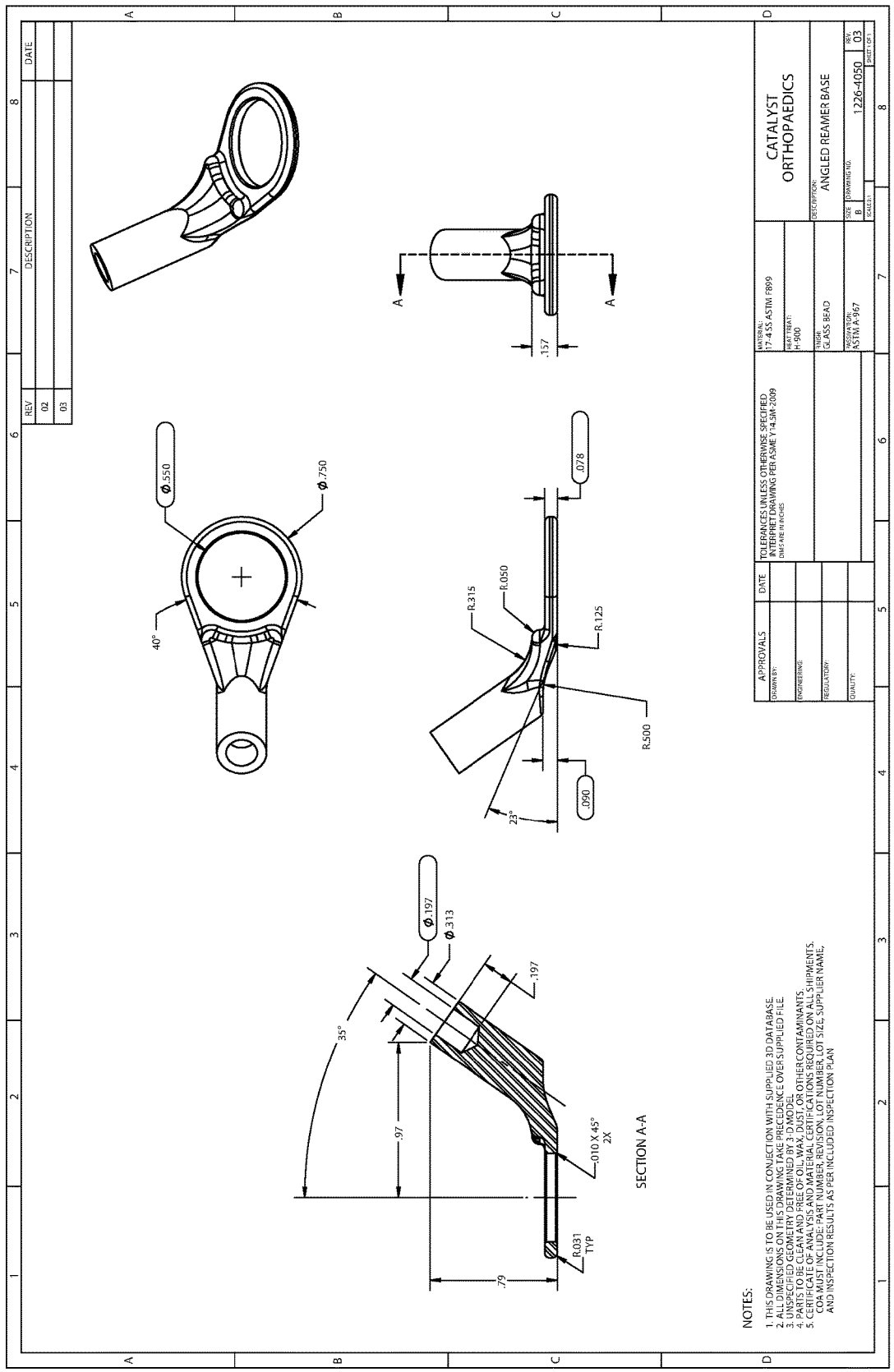
FIG. 34 is an engineering drawing of a working tip of the offset reamer of FIG. 18.
Figure 35:
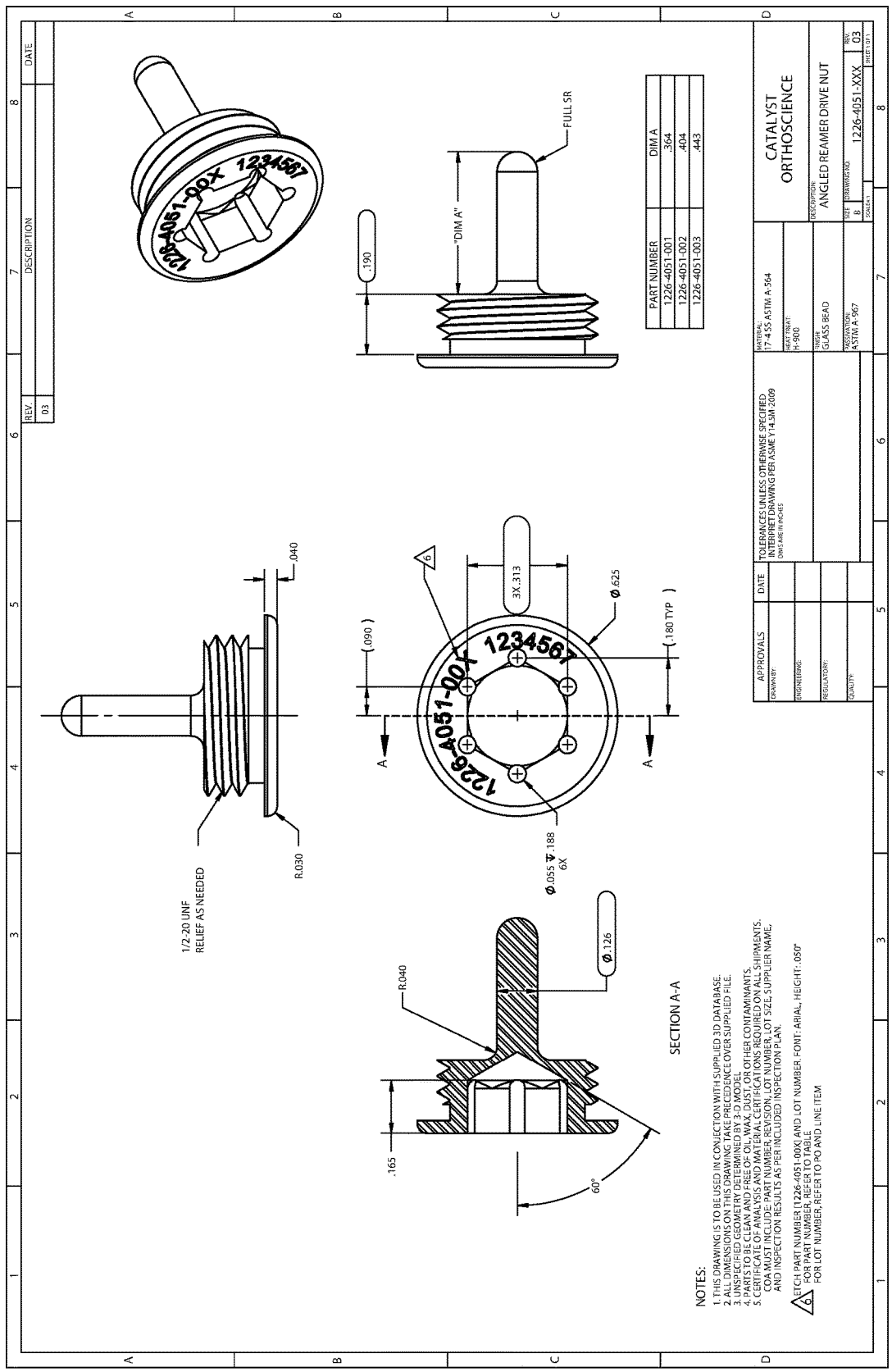
FIG. 35 is an engineering drawing of a reamer coupler of the offset reamer of FIG. 18.
Figure 36:
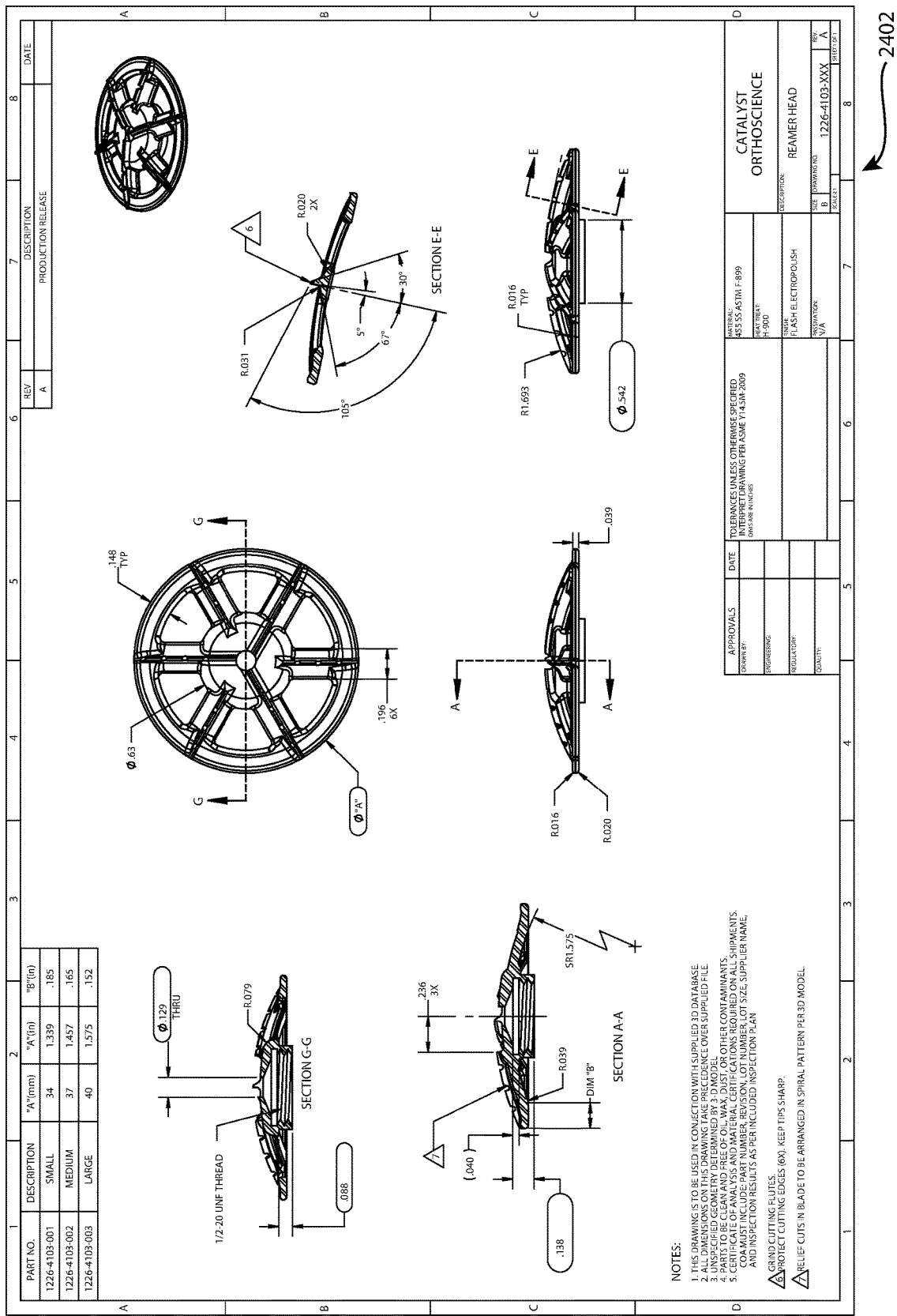
FIG. 36 is an engineering drawing of a reamer head of the offset reamer of FIG. 25.
Figure 37:
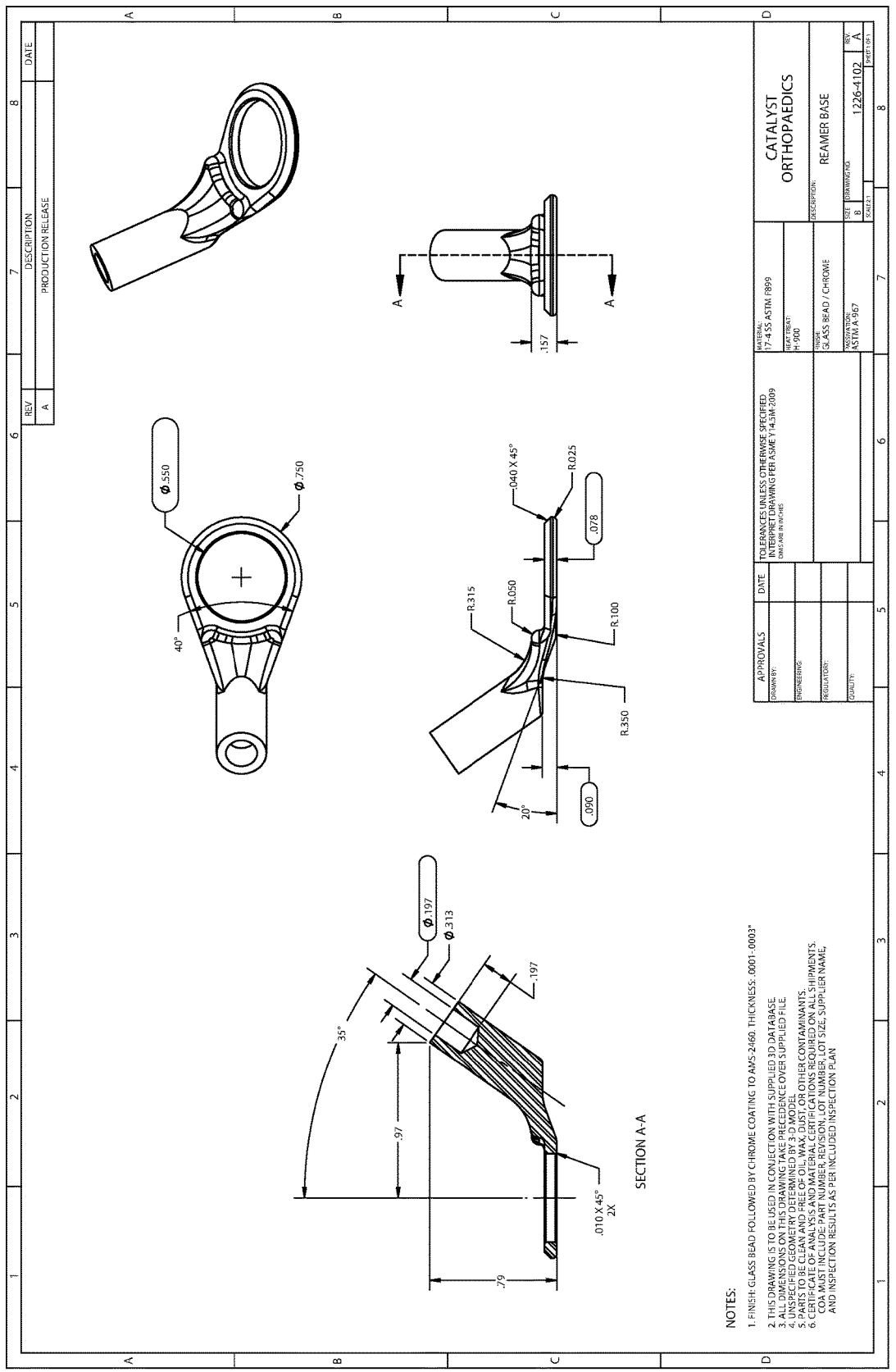
FIG. 37 is an engineering drawing of a working tip of the offset reamer of FIG. 25.
Figure 38:
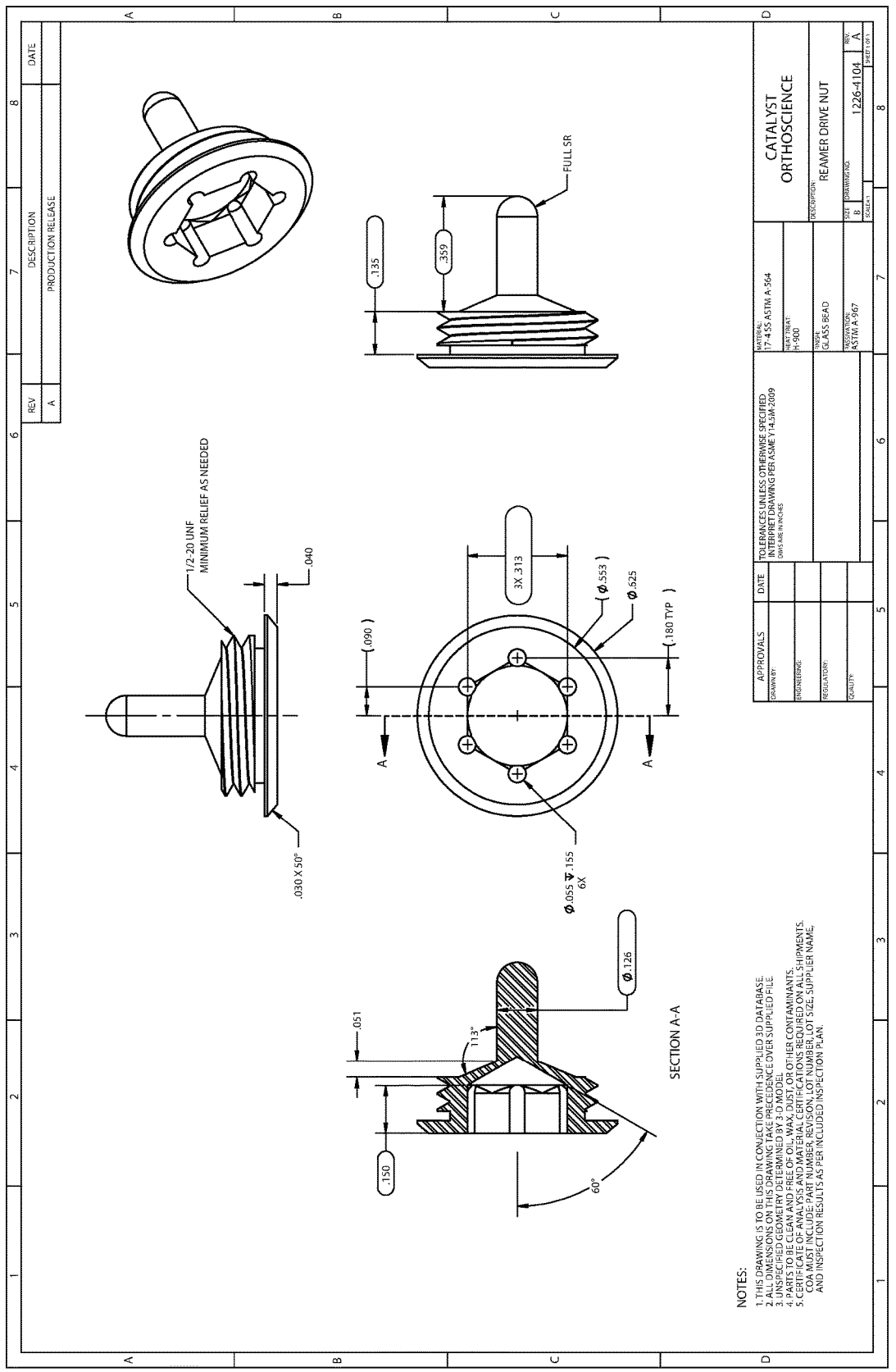
FIG. 38 is an engineering drawing of a reamer coupler of the offset reamer of FIG. 25.

The nominal overall height of the working portion of reamer 2300 from the top of the reamer coupler to the bottom of the shaft is 16.104 mm (0.634 in). Referring to FIG. 35, this example is part no. 1226-4051-002 with nominal "DIM A"=0.404. The nominal overall height of the working portion of reamer 2400 from the top of the reamer coupler to the bottom of the shaft is 13.564 mm (0.534 in) in the example shown, with reference to FIG. 38. The reduction in overall height of the working portion from reamer 2300 to reamer 2400 is thus 2.54 mm (0.100 in) in the examples shown. Referring to FIGS. 33 and 36, the reamer heads 2302, 2402 are provided in the same three outer diameters "A." The nominal medium diameter is 37 mm (1.457 in). The nominal ratio of overall height to outer diameter is thus (0.634 in/1.457 in)=0.44 for reamer 2300 and (0.534 in/1.457 in)=0.37 for reamer 2400. Referring to FIGS. 33 and 35 for reamer 2300, the nominal ratio of overall height to outer diameter is 0.38-0.50 for all combinations of reamer head sizes and reamer coupler sizes. Referring to FIGS. 36 and 38 for reamer 2400, the nominal ratio of overall height to outer diameter is 0.34-0.40 for all combinations of reamer head sizes with the single reamer coupler size.

Referring to FIGS. 24, 33, and 35, the top of the reamer coupler 2304 protrudes outwardly past the top of the reamer head 2302 a distance 2301. The nominal distance 2301 is 0.128 in. The nominal ratio of the distance 2301 to the outer diameter is 0.08-0.09 for all combinations of sizes. The nominal ratio of the distance 2301 to the overall height is 0.19-0.22 for all combinations of sizes. Referring to FIGS. 24, 31, 32A, and 32B, these nominal ratios are even less for reamer 2400 than for reamer 2300.

Offset reamers 2100, 2200, 2300, 2400 are mechanically simple designs. The reamer heads 2102, 2202, 2302, 2402 are captured at the end of angled shafts 2108, 2208, 2308, 2408 respectively. The shafts are used to position and stabilize the reamer heads. The reamer heads 2102, 2202 are driven, or turned, by a separate driver, such as reamer driver 2216, 2316, 2416 which directly engages drive portions 2196, 2296, 2396, 2496 on the reamer couplers 2104, 2204, 2304, 2404 respectively. The reamer drivers 2216, 2316, 2416 are shown with a ball hex feature on the distal end that allows the shaft 2219, 2319, 2419 to be misaligned, angularly offset, or obliquely oriented, relative to the reamer head axis 2103, 2203, 2303, 2403. The specific example shown provides up to 30 degrees of angular misalignment, although any amount of misalignment is contemplated as a matter of design choice. In other words, the magnitude of the angular offset or oblique angle may be greater than zero degrees and less than 180 degrees. The offset reamers 2100, 2200, 2300, 2400 may be driven by a prime mover or torque source such as a power instrument, or manually using a T-handle. The prime mover may couple directly to a fitting such as a Hudson connector or torque bit of the driver.

The reamer coupler 2104 includes a shaft 2194 which may be a drill tip, and which may protrude through the obverse of the reamer head 2102; and the reamer head 2202 includes a central shaft 2287 which may also be a drill tip; both features may eliminate a separate step to drill a pilot hole. The drill tips may be face cutting only, lacking any cutting edges along their long axis. This feature may prevent the drill tips from skiving laterally under load. The reamer couplers 2304, 2404 include shafts 2394, 2494 which are smooth with blunt tips. This design may significantly reduce the effort necessary to slide the working portions of reamers 2300, 2400 into a shoulder joint along a trajectory that is aligned with or parallel to the glenoid articular surface (i.e., in a substantially anterior-posterior direction), because the blunt tips slide much more easily across the glenoid articular surface than a pointed tip would. The chamfers 2440, 2442 of reamer 2400 (FIG. 31) similarly reduce the insertion effort because the angled (or beveled) edges slide much more easily across the humeral head and push the humeral head out of the way more effectively than a "sharp" 90 degree corner or even a rounded corner with a fillet radius.

Offset reamers 2100, 2200, 2300, 2400 provide easy clearance around interfering structures, due to the angled shafts 2108, 2208, 2308, 2408 and handles 2110, 2210, 2310, 2410 relative to the reamer heads 2102, 2202, 2302, 2402. The operation of offset reamers 2100, 2200, 2300, 2400 is stable because the stabilizing action of the handles 2110, 2210, 2310, 2410 and the torque drive loads are structurally separated. Offset reamers 2100, 2200, 2300, 2400 may provide effective cutting action due to the direct loading of the cutting head through a separate drive shaft, such as shafts 2219, 2319, 2419. The drive shafts 2219, 2319, 2419 need only be angled sufficiently to avoid contact with the interfering structures, such as the humeral head. The construction of the offset reamers 2100, 2200, 2300, 2400 is simple and cost effective to manufacture.

A method of using the offset reamer 2100 to prepare an implantation site for the glenoid components will now be described. The method may include the steps of providing the offset reamer 2100, with the handle 2110, the shaft 2108, and a working portion including the working tip 2106, the reamer head 2102, and the reamer coupler 2104; inserting the working portion into a shoulder joint (FIG. 1) along a first trajectory so that the shaft 2194 is in the pilot hole 10; providing the reamer driver 2216, with the shaft 2219, the Hudson connector 2218 or torque bit at one end of the shaft 2219, and the drive tip 2220 at an opposite end of the shaft 2219 from the Hudson connector 2218 or torque bit; coupling the Hudson connector 2218 or torque bit to a prime mover; engaging the drive tip 2220 of the reamer driver 2216 with the drive portion 2196 of the reamer coupler 2104 along a second trajectory which is angularly offset from the first trajectory; actuating the prime mover to rotate the reamer driver 2216 about the axis 2221 to turn the reamer coupler 2204 and the reamer head 2202 about the axis 2203, thereby preparing a reamed surface 14 in the glenoid fossa 4 (FIG. 3); and removing the working portion and the reamer driver 2216.

The step of providing the offset reamer 2100 may include the steps of coupling the handle 2110, shaft 2108, and working tip 2106 together to form a handle assembly; and assembling the reamer head 2102, reamer coupler 2104, and working tip 2106 to form a working portion, wherein the reamer head 2102 and the reamer coupler 2104 are rotationally coupled or fixed together and free to rotate relative to the working tip 2106 about axis 2103.

The step of inserting the working portion into a shoulder joint may include manipulating the handle 2110 to orient or re-orient the working portion. The first trajectory may be between the humeral head and the glenoid fossa 4 (FIG. 1), and aligned with or parallel to the glenoid articular surface (or joint line). One can appreciate that in the shoulder joint, the first trajectory may be from an anterior or an anterolateral approach to the joint so that the working portion presents its thinnest profile as it enters the joint. Referring to FIG. 10, the thinnest profile of the working portion is the overall height from the top of the reamer coupler 2104 to the bottom of the obverse side 2178 of the reamer head 2102 (if the shaft 2194 is retractable) or to the bottom of the shaft 2194 if the shaft 2194 is not retractable. The second trajectory may be tangent to the humeral head and aimed at the drive portion 2196 of the reamer coupler 2104 (which is already in the shoulder joint). The second trajectory may be from an anterolateral or lateralized approach to the joint so that the drive tip 2220 presents its smallest profile as it enters the joint. Referring to FIGS. 14 and 15, the thinnest profile of the drive tip 2220 (and of the drive shaft 2216) is when viewed along axis 2221 in an end view. Because the working portion and the reamer driver 2216 are separate items, introduced into the joint separately or one at a time, and engaged together in the joint, each item may be introduced into the joint along a trajectory that offers the least resistance to insertion or the least amount of joint distraction or dissection. An integral or non-separable design, by contrast, may have a larger insertion profile which may dictate an insertion trajectory which results in relatively more resistance, joint distraction, and/or dissection.

The step of actuating the prime mover may be preceded by, or performed simultaneously with, a step of reorienting the reamer driver 2216 to lie along a third trajectory which is angularly offset from the first trajectory and the second trajectory. Reorienting the reamer driver 2216 may involve polyaxial rotation of the reamer driver 2216 about the drive tip 2220. The third trajectory may thus be non-coplanar with the first trajectory and the second trajectory.

The preceding method applies equally to the offset reamer 2200. The step of providing the offset reamer 2200 may include the steps of coupling the handle 2210, shaft 2208, and working tip 2206 together to form a handle assembly; and assembling the reamer head 2202, first bushing 2212, second bushing 2214, reamer coupler 2204, and working tip 2206 to form a working portion, wherein the reamer head 2202 and the reamer coupler 2204 are rotationally coupled or fixed together and free to rotate relative to the working tip 2206 about axis 2203.

The preceding method applies equally to the offset reamer 2300. The step of inserting the working portion into the shoulder joint along the first trajectory may include the step of sliding the blunt tip of the shaft 2394 across the natural glenoid articular surface to the pilot hole 10.

The preceding method applies equally to the offset reamer 2400. The step of inserting the working portion into the shoulder joint along the first trajectory may include the steps of sliding the blunt tip of the shaft 2494 across the natural glenoid articular surface to the pilot hole 10 and pushing the chamfers 2440, 2442 against the humeral head.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the examples of the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A reamer system comprising:
   a reamer head comprising a first side, a second side opposite the first side, and a first central longitudinal rotational axis, wherein the second side comprises cutting features;
   a reamer coupler that comprises a polyaxial drive portion for torque transmission to the reamer coupler;
   wherein the reamer coupler transmits torque from the polyaxial drive portion to the reamer head and wherein a shaft protrudes outwardly from the second side of the reamer head along a second central longitudinal rotational axis, wherein the second central longitudinal rotational axis of the shaft is constrained to remain coaxial with the first central longitudinal rotational axis of the reamer head during rotation.

2. The reamer system of claim 1, wherein the reamer head comprises an outer diameter that encircles the second side, wherein the reamer coupler extends between a first end and a second end opposite the first end, wherein the reamer coupler comprises an overall height measured between the first and second ends, wherein a ratio of the overall height of the reamer coupler to the outer diameter of the reamer head is less than or equal to 0.50.

3. The reamer system of claim 1, comprising:
   a working tip comprising a plate portion and a shaft portion, wherein the plate portion comprises a first surface, a second surface opposite the first surface, and a hole that extends through the plate portion between the first and second surfaces, wherein the shaft portion extends obliquely outwardly from an outer periphery of the first surface;
   wherein the reamer head comprises an annular cavity that extends into the reamer head through the first side;
   wherein the reamer head, reamer coupler, and working tip are coupled together so that the first side of the reamer head and the first surface of the plate portion face the same way, the reamer coupler extends through the hole of the plate portion, and at least a portion of the plate portion is received within the annular cavity.

4. The reamer system of claim 3, wherein the reamer head comprises a reamer head shaft that protrudes from the first side of the reamer head and is encircled by the annular cavity, the reamer head shaft comprising a first portion deep within the annular cavity closer to the second side of the reamer head, and a second portion that extends from the first portion away from the second side of the reamer head;
   wherein the reamer head and working tip are coupled together so that the reamer head shaft extends through the hole of the plate portion.

5. The reamer system of claim 1 further comprising:
   a reamer driver configured to removably couple with the polyaxial drive portion of the reamer coupler for torque transmission to the reamer coupler, wherein the reamer driver is configured to couple with the polyaxial drive portion of the reamer coupler while the reamer head and reamer coupler are inserted into a joint of a patient.

6. The reamer system of claim 5, wherein the reamer driver is movable relative to the reamer coupler when the reamer driver is coupled with the polyaxial drive portion of the reamer coupler.

7. The reamer system of claim 6, wherein the reamer head, the reamer coupler, and the shaft rotate about the first central longitudinal rotational axis of the reamer head in response to torque transmitted from the reamer driver to the reamer coupler, wherein the reamer driver is movable relative to the reamer coupler to form an angle between a rotational axis of the reamer driver and the first central longitudinal rotational axis of the reamer head.

8. The reamer system of claim 7, wherein the reamer driver is polyaxially movable relative to the reamer coupler to form the angle between the rotational axis of the reamer driver and the first central longitudinal rotational axis of the reamer head.

9. The reamer system of claim 1, wherein the reamer coupler is separate from the reamer head.

10. A reamer system comprising:
a working portion comprising:
a bone-facing side comprising cutting features and a first central longitudinal rotational axis;
a polyaxial drive portion for torque transmission to the bone-facing side; and
a shaft that protrudes outwardly from the bone-facing side along the first central longitudinal rotational axis;
wherein the bone-facing side, the polyaxial drive portion, and the shaft rotate about the first central longitudinal rotational axis when torque is transmitted from the polyaxial drive portion to the bone-facing side; and
a reamer driver comprising:
a reamer driver shaft comprising:
a proximal end;
a distal end; and
a second central longitudinal rotational axis; and
a polylobular ball-shaped drive tip coupled to the distal end of the reamer driver shaft;
wherein a cross-section of the polylobular ball-shaped drive tip taken perpendicular to the second central longitudinal rotational axis is non-circular; and
wherein the polylobular ball-shaped drive tip is configured to engage the polyaxial drive portion to transmit torque from the polylobular ball-shaped drive tip to the polyaxial drive portion.

11. The reamer system of claim 10, comprising:
a working tip comprising a plate portion and a shaft portion, wherein the plate portion comprises a first surface, a second surface opposite the first surface, and a hole that extends through the plate portion between the first and second surfaces, wherein the shaft portion extends obliquely outwardly from an outer periphery of the first surface;
a reamer head comprising the bone-facing side and a first side opposite the bone-facing side,
wherein the reamer head comprises an annular cavity that extends into the reamer head through the first side; and
a reamer coupler comprising the polyaxial drive portion;
wherein the reamer head, reamer coupler, and working tip are coupled together so that the first side of the reamer head and the first surface of the plate portion face the same way, the reamer coupler extends through the hole of the plate portion, and at least a portion of the plate portion is received within the annular cavity.

12. The reamer system of claim 11, wherein the reamer head comprises a reamer head shaft that protrudes from the first side of the reamer head and is encircled by the annular cavity, the reamer head shaft comprising a first portion deep within the annular cavity closer to a second side of the reamer head, and a second portion that extends from the first portion away from the second side of the reamer head;
wherein the reamer head and working tip are coupled together so that the reamer head shaft extends through the hole of the plate portion.

13. The reamer system of claim 10 wherein:
the polylobular ball-shaped drive tip is configured to removably couple with the polyaxial drive portion for torque transmission to the polyaxial drive portion, and wherein the polylobular ball-shaped drive tip is configured to couple with the polyaxial drive portion while the bone-facing side and the polyaxial drive portion are inserted into a joint of a patient.

14. The reamer system of claim 13, wherein the reamer driver shaft is movable relative to the polyaxial drive portion when the polylobular ball-shaped drive tip is coupled with the polyaxial drive portion.

15. The reamer system of claim 14, wherein the reamer driver shaft is movable relative to the polyaxial drive portion to form an angle between the second central longitudinal rotational axis of the reamer driver shaft and the first central longitudinal rotational axis.

16. The reamer system of claim 15, wherein the reamer driver shaft is polyaxially movable relative to the polyaxial drive portion to form the angle between the second central longitudinal rotational axis of the reamer driver shaft and the first central longitudinal rotational axis.

17. The reamer system of claim 10, wherein the polylobular ball-shaped drive tip comprises a hexalobular ball shape.

18. The reamer system of claim 10, wherein the polyaxial drive portion comprises a polyaxial socket configured to receive the polylobular ball-shaped drive tip therein for torque transmission from the polylobular ball-shaped drive tip to the polyaxial socket.

19. A reamer system comprising:
a working portion comprising:
a first side comprising a polyaxial torque input feature; and
a second side opposite the first side, wherein the second side comprises cutting features;
wherein the first side of the working portion transmits torque to the second side of the working portion; and
a reamer driver comprising:
a reamer driver shaft comprising:
a proximal end;
a distal end; and
a central longitudinal rotational axis; and
a drive tip coupled to the distal end of the reamer driver shaft, the drive tip comprising a generally spherical shape with a plurality of curved facets arranged about the central longitudinal rotational axis;
wherein the drive tip is configured to engage the polyaxial torque input feature to transmit torque from the drive tip to the polyaxial torque input feature.

20. The reamer system of claim 19, wherein the working portion further comprises:
a working tip comprising a plate portion and a shaft portion, wherein the plate portion comprises a first surface, a second surface opposite the first surface, and a hole that extends through the plate portion between the first and second surfaces, wherein the shaft portion extends obliquely outwardly from an outer periphery of the first surface;
wherein the second side of the working portion comprises a reamer head, and the first side of the working portion comprises a reamer coupler, and wherein the reamer head, the reamer coupler, and the working tip are coupled together so that the first side of the reamer head and the first surface of the plate portion face the same way, the reamer coupler extends through the hole of the plate portion, and at least a portion of the plate portion is received within an annular cavity of the reamer head.

21. The reamer system of claim 20, wherein the reamer head comprises a reamer head shaft that protrudes from the first side of the reamer head and is encircled by the annular cavity, the reamer head shaft comprising a first portion deep within the annular cavity closer to the second side of the reamer head, and a second portion that extends from the first portion away from the second side of the reamer head;
  wherein the reamer head and working tip are coupled together so that the reamer head shaft extends through the hole of the plate portion.

22. The reamer system of claim 19 wherein:
  the drive tip is configured to removably couple with the polyaxial torque input feature of the first side of the working portion for torque transmission to the polyaxial torque input feature while the working portion is inserted into a joint of a patient.

23. The reamer system of claim 22, wherein the polyaxial torque input feature and the cutting features rotate about a central longitudinal rotational axis of the working portion in response to torque transmission from the drive tip to the polyaxial torque input feature, wherein the drive tip is polyaxially movable relative to the polyaxial torque input feature to form an angle between the central longitudinal rotational axis of the reamer driver shaft and the central longitudinal rotational axis of the working portion when the drive tip is coupled with the polyaxial torque input feature of the first side of the working portion.

24. The reamer system of claim 19, wherein the polyaxial torque input feature comprises a polyaxial socket configured to receive the drive tip therein for torque transmission from the drive tip to the polyaxial socket.

25. The reamer system of claim 19, wherein the plurality of curved facets comprise a plurality of arcuate facets.

* * * * *

UNITED STATES PATENT AND TRADEMARK OFFICE
CERTIFICATE OF CORRECTION

PATENT NO. : 11,007,063 B2  
APPLICATION NO. : 15/918088  
DATED : May 18, 2021  
INVENTOR(S) : Steven S. Goldberg et al.

Page 1 of 1

It is certified that error appears in the above-identified patent and that said Letters Patent is hereby corrected as shown below:

On the Title Page

Item (72) Inventors:
Steven S. Goldberg, Naples, FL (US); Stephen M. Herrington, Naples, FL (US); Ephraim Akyuz, Salt Lake City, UT (US)
Should read:
-- Steven S. Goldberg, Naples, FL (US); Stephen M. Herrington, Naples, FL (US); Ephraim Akyuz, Salt Lake City, UT (US); Daniel Triplett, Huntsville, UT (US); Daniel F. Justin, Orlando, FL (US) --

Signed and Sealed this
Thirtieth Day of September, 2025

John A. Squires
*Director of the United States Patent and Trademark Office*